(12) United States Patent
Korber et al.

(10) Patent No.: US 9,174,967 B2
(45) Date of Patent: Nov. 3, 2015

(54) SUBSTITUTED PYRAZOLE-CONTAINING COMPOUNDS AND THEIR USE AS PESTICIDES

(71) Applicant: BASF SE, Ludwigshafen (DE)

(72) Inventors: Karsten Korber, Eppelheim (DE); Florian Kaiser, Mannheim (DE); Gemma Veitch, Basel (CH); Wolfgang Von Deyn, Neustadt (DE); Nina Gertrud Bandur, Ludwigshafen (DE); Joachim Dickhaut, Heidelberg (DE); Arun Narine, Mannheim (DE); Deborah L. Culbertson, Fuquay Varina, NC (US); Paul Neese, Apex, NC (US); Koshi Gunjima, Toyohashi (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/398,239

(22) PCT Filed: Apr. 29, 2013

(86) PCT No.: PCT/EP2013/058845
§ 371 (c)(1),
(2) Date: Oct. 31, 2014

(87) PCT Pub. No.: WO2013/164295
PCT Pub. Date: Nov. 7, 2013

(65) Prior Publication Data
US 2015/0087509 A1    Mar. 26, 2015

Related U.S. Application Data

(60) Provisional application No. 61/642,469, filed on May 4, 2012.

(51) Int. Cl.
| C07D 403/04 | (2006.01) |
| C07D 403/14 | (2006.01) |
| A01N 43/56 | (2006.01) |
| A01N 47/36 | (2006.01) |
| A01N 57/32 | (2006.01) |
| C07F 9/24 | (2006.01) |
| A01N 47/34 | (2006.01) |
| A01N 57/24 | (2006.01) |
| A61K 31/506 | (2006.01) |
| A61K 31/675 | (2006.01) |

(Continued)

(52) U.S. Cl.
CPC .............. *C07D 403/04* (2013.01); *A01N 43/56* (2013.01); *A01N 47/34* (2013.01); *A01N 47/36* (2013.01); *A01N 57/24* (2013.01); *A01N 57/32* (2013.01); *A61K 31/506* (2013.01); *A61K 31/675* (2013.01); *A61K 45/06* (2013.01); *C07D 403/14* (2013.01); *C07D 405/14* (2013.01); *C07D 409/14* (2013.01); *C07F 9/247* (2013.01); *C07F 9/65583* (2013.01)

(58) Field of Classification Search
CPC ...... C07D 403/03; C07D 403/14; A01N 43/56
USPC ............................ 544/330, 331, 332; 514/275
See application file for complete search history.

(56) References Cited

U.S. PATENT DOCUMENTS

| 8,513,260 B2 | 8/2013 | Schwarz et al. |
| 8,629,273 B2 | 1/2014 | Schwarz et al. |
| 2010/0144672 A1 | 6/2010 | Frackenpohl et al. |
| 2011/0190365 A1 | 8/2011 | Werner et al. |

FOREIGN PATENT DOCUMENTS

| DE | 102007003036 | 6/2008 |
| WO | WO 2008/077483 | 7/2008 |

(Continued)

OTHER PUBLICATIONS

International Search Report, PCT/EP2013/058845, filed Apr. 29, 2013, search completed Jun. 12, 2013.

(Continued)

*Primary Examiner* — Deepak Rao
(74) *Attorney, Agent, or Firm* — Brinks Gilson & Lione

(57) ABSTRACT

The present invention relates to substituted pyrazole-containing compounds of formula (I), and the stereoisomers and salts thereof,

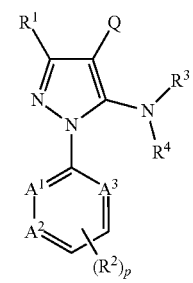

(I)

wherein the substituents are as defined in the description.

The present invention further relates to a method for combating or controlling invertebrate pests, to a method for protecting plant propagation material and/or the plants which grow therefrom, to plant propagation material comprising at least one compound according to the present invention, to a method for treating or protecting an animal from infestation or infection by parasites, to a process for the preparation of a composition for treating infested or infected animals and/or for protecting animals against infestation or infection by parasites, and to a compound according to the invention for use as a medicament.

26 Claims, No Drawings

(51) Int. Cl.
    *A61K 45/06*     (2006.01)
    *C07D 405/14*     (2006.01)
    *C07D 409/14*     (2006.01)
    *C07F 9/6558*     (2006.01)

(56) References Cited

FOREIGN PATENT DOCUMENTS

| | | |
|---|---|---|
| WO | WO 2009/156090 | 12/2009 |
| WO | WO 2010/017902 | 2/2010 |
| WO | WO 2010/136145 | 12/2010 |
| WO | WO 2011/057984 | 5/2011 |

OTHER PUBLICATIONS

International Preliminary Report on Patentability, PCT/EP2013/058845, filed Apr. 29, 2013, report issued Nov. 4, 2014.

Aggarwal et al., "Synthesis and antibacterial activity of some new 1-heteroaryl-5-amino-3*Hl*methyl-4-phenylpyrazoles", Bioorganic & Medicinal Chemistry, vol. 14, 2006, pp. 1785-1791.

Dymek et al., "Synthesa I Badania Pochodnych Pirazolu", Acta Poloniae Pharamaceutica, vol. 25, No. 4, Jan. 1, 1968, pp. 375-382, compounds XXVII and XXVIII on p. 381, Search Report.

Winters et al., "Synthesis of Fused Isoquinolinones by Thermal Cyclization of Beta-Phenyl-Alpha-Substituted Amino Heterocyclic Compounds", Tetrahedron Letters, No. 44, Jan. 1, 1975, pp. 3877-3878, Search Report.

SUBSTITUTED PYRAZOLE-CONTAINING COMPOUNDS AND THEIR USE AS PESTICIDES

This application is a National Stage application of International Application No. PCT/EP2013/058845, filed Apr. 29, 2013, which claims the benefit of U.S. Provisional Application No. 61/642,469, filed May 4, 2012, the entire contents of which are hereby incorporated herein by reference.

The present invention relates to novel substituted pyrazole-containing compounds and the stereoisomers, N-oxides, tautomers and salts thereof and to compositions comprising the same. The invention also relates to the use of the N-thioanthranilamide compounds or of the compositions comprising such compounds for combating invertebrate pests. Furthermore, the invention relates to methods for controlling invertebrate pests by using these compounds or their compositions.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

It is an object of the present invention to provide further compounds having a high pesticidal activity against invertebrate pests, in particular against insect pest. The compounds should show a broad activity spectrum against a large number of different invertebrate pests, in particular against difficult to control insects, arachnids and nematodes.

It has been found that the above objectives can be achieved by substituted pyrazole-containing compounds of the general formula (I), as defined below, including their stereoisomers, N-oxides, tautomers and their salts, in particular their agriculturally or veterinarily acceptable salts.

Therefore, in a first aspect the present invention relates to substituted pyrazole-containing compounds of formula (I),

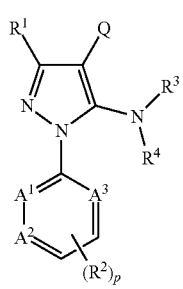
(I)

wherein
$A^1$ is N or C—$R^2$,
$A^2$ is N or C—$R^2$,
$A^3$ is N or C—$R^2$,
with the proviso that no more than two nitrogen are present in the ring that contains $A^1$, $A^2$, $A^3$;
Q is selected from phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

$R^1$ is selected from the group consisting of halogen; cyano; azido; nitro; —SCN; $SF_5$; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$; —Si($R^{14}$)$_2$$R^{13}$; —$OR^8$; —OS(O)$_n$$R^8$; —$SR^8$; —S(O)$_m$$R^8$; —S(O)$_n$N($R^{9a}$)$R^{9b}$; —N($R^{9a}$)$R^{9b}$; —N($R^{9a}$)C(=O)$R^7$; C(=O)$R^7$; —C(=O)$OR^8$; —C(=N$R^{9a}$)H; —C(=N$R^{9a}$)$R^7$; —C(=O)N($R^{9a}$)$R^{9b}$; C(=S)N($R^{9a}$)$R^{9b}$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

$R^2$ is selected from the group consisting of hydrogen, halogen, cyano, azido, nitro, —SCN, $SF_5$, $C_1$-$C_6$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —Si($R^{14}$)$_2$$R^{13}$, —$OR^8$, —OS(O)$_n$$R^8$, —$SR^8$, —S(O)$_m$$R^8$, —S(O)$_n$N($R^{9a}$)$R^{9b}$, —N($R^{9a}$)$R^{9b}$, N($R^{9a}$)C(=O)$R^7$, —C(=O)$R^7$, —C(=O)$OR^8$, —C(=S)$R^7$, —C(=S)$OR^8$, —C(=N$R^{9a}$)$R^7$, —C(=O)N($R^{9a}$)$R^{9n}$, —C(=S)N($R^{9a}$)$R^{9b}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

$R^3$ is selected from the group consisting of nitro, —N$R^{9a}$$R^{9b}$, —S(O)$_n$N($R^{9a}$)$R^{9b}$; —C(=O)N($R^{9a}$)$R^{9b}$; —C(=S)N($R^{9a}$)$R^{9b}$; —C(=N$R^{9a}$)—S(O)$_m$$R^8$, —P(O)$G_2$, —$PG_3$, —N=N—$R^{9a}$;

$R^4$ is selected from the group consisting of hydrogen, cyano, $C_1$-$C_6$-alkyl which may be partially or fully halogenated and/or may be substituted by one or more radicals $R^7$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^7$, $C_3$-$C_8$-cycloalkyl which may be partially or fully halogenated and/or may be substituted by one or more radicals $R^7$, $C_3$-$C_8$-cycloalkyl-$C_1$-$C_4$-alkyl where the cycloalkyl moiety may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —N($R^{9a}$)$R^{9b}$; —N($R^{9a}$)C(=O)$R^7$; —Si($R^{14}$)$_2$$R^{13}$; —$OR^8$; —$SR^8$; —S(O)$_m$$R^8$; —S(O)$_n$N($R^{9a}$)$R^{9b}$; —C(=O)$R^7$; —C(=O)$OR^8$; —C(=O)N($R^{9a}$)$R^{9b}$; —C(=S)$R^7$; —C(=S)$OR^8$; —C(=S)N($R^{9a}$)$R^{9b}$; —C(=N$R^{9a}$)—S(O)$_m$$R^8$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^3$ and $R^4$ form together with the nitrogen they are bound to a group of the formula A.1

(A.1)

or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

provided that $R^3$ and $R^4$ do not form together with the nitrogen atom they are bound a substituted or unsubstituted piperidine, pyrrolidine or morpholine G is selected independently from each other and independently of each occurrence from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylamino, $C_1$-$C_6$-dialkylamino, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

$R^5$ and $R^6$ each independently are $C_1$-$C_{12}$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_{12}$-alkenyl which may be partially or fully halogenated and/or may be substituted by one or more radicals $R^7$, $C_2$-$C_{12}$-alkynyl which may be partially or fully halogenated and/or may be substituted by one or more radicals $R^7$, —C(=O)$R^7$, —C(=NOR$^8$)$R^7$, —C(=NN(R$^{9a}$)R$^{9b}$)R$^7$, —C(=O)OR$^7$, —C(=O)N(R$^{9a}$)R$^{9B}$, —OC(=O)R$^7$, —OC(=O)OR$^8$, —NR$^{9a}$C(=O)R$^7$, —N[C(=O)R$^7$]$_2$, —NR$^7$C(=O)OR$^8$, —C(=O)N(R$^{9a}$)—N(R$^{9b}$)$_2$, —C(=O)NR$^{9a}$—NR$^{9b}$[C(=O)R$^7$], —NR$^{9a}$—C(=O)N(R$^{9b}$)$_2$, —NR$^{9a}$—NR$^{9b}$C(=O)R$^7$, —NR$^{9a}$—N[C(=O)R$^7$]$_2$, —N[(C=O)R$^7$]—N(R$^{9a}$)$_2$, —NR$^{9a}$—NR$^{9b}$[(C=O)OR$^8$], —NR$^{9a}$[(C=O)N(R$^{9b}$)$_2$], —NR$^{9a}$[C=NR$^{9b}$]R$^7$, —NR$^{9a}$(C=NR$^{9b}$)N(R$^{9b}$)$_2$, —O—N(R$^{9a}$)$_2$, —O—NR$^{9a}$(C=O)R$^7$, —SO$_2$NR$^{9a}$R$^{9b}$, —NR$^{9a}$SO$_2$R$^8$, —SO$_2$OR$^8$, —OSO$_2$R$^8$, —OR$^8$, —NR$^{9a}$R$^{9b}$, —SR$^8$, —Si(R$^{14}$)$_2$R$^{13}$, —PR$^{9a}$R$^{9b}$, —SOR$^8$, —SO$_2$R$^8$, or —P(=O)$_t$G$_2$, —P(=O)$_2$G$_2$;

or $R^5$ and $R^6$ together with the sulfur atom to which they are attached form a saturated, partially unsaturated or unsaturated 3- to 8-membered ring which optionally contains 1 to 4 further heteroatoms selected from oxygen, nitrogen, sulfur, which ring can be fused with one or two saturated, partially unsaturated or unsaturated 5- to 6-membered rings which may contain 1 to 4 heteroatoms selected from oxygen, nitrogen, sulfur, wherein all of the above rings are unsubstituted or substituted by any combination of 1 to 6 groups $R^{18}$;

each $R^7$ is independently selected from the group consisting of cyano, azido, nitro, —SCN, $SF_5$, $C_1$-$C_4$-alkyl, $C_3$-$C_8$-cycloalkyl, $C_3$-$C_8$-halocycloalkyl, —Si(R$^{14}$)$_2$R$^{13}$, —OR$^8$, —OSO$_2$R$^8$, —SR$^8$, —S(O)$_m$R$^8$, —S(O)$_n$N(R$^{9a}$)R$^{9b}$, —N(R$^{9a}$)R$^{9b}$, —C(=O)N(R$^{9a}$)R$^{9b}$, —C(=S)N(R$^{9a}$)R$^{9b}$, —C(=O)OR$^8$, —C(=O)R$^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

and, in case $R^7$ is bound to a cycloalkyl group or to a heterocyclic ring, $R^7$ may additionally be selected from the group consisting of $C_1$-$C_6$-alkyl, $C_1$-$C_6$-haloalkyl, $C_2$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

and in groups —C(=O)R$^7$, —C(=S)R$^7$, —C(=NR$^{9a}$)R$^7$ and —N(R$^{9a}$)C(=O)R$^7$, $R^7$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^7$ together form a group selected from =CR$^{11}$R$^{12}$, =S(O)$_m$R$^8$, =S(O)$_m$N(R$^{9a}$)R$^{9b}$, =NR$^{9a}$, =NOR$^8$ and =NNR$^{9a}$R$^{9b}$;

or two radicals $R^7$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^8$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si(R$^{14}$)$_2$R$^{13}$, —SR$^{20}$, —S(O)$_m$R$^{20}$, —S(O)$_n$N(R$^{9a}$)R$^{9b}$, —N(R$^{9a}$)R$^{9b}$, —N=CR$^{15}$R$^{16}$, —C(=O)R$^{17}$, —C(=O)N(R$^{9a}$)R$^{9b}$, —C(=S)N(R$^{9a}$)R$^{9b}$, —C(=O)OR$^{20}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; with the proviso that $R^8$ is not $C_1$-$C_6$-alkoxy or $C_1$-$C_6$-haloalkoxy if it is bound to an oxygen atom;

$R^{9a}$, $R^{9b}$ are, independently of each other and independently of each occurrence, selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —$N(R^{21})R^{22}$; —$N(R^{21})C(=O)R^{19}$; —$Si(R^{14})_2R^{13}$; —$OR^{20}$; —$SR^{20}$; —$S(O)_mR^{20}$; —$S(O)_nN(R^{21})R^{22}$; —$C(=O)R^{19}$; —$C(=O)OR^{20}$; —$C(=O)N(R^{21})R^{22}$; —$C(=S)R^{17}$; —$C(=S)OR^{20}$, —$C(=S)N(R^{21})R^{22}$; —$C(=NR^{21})R^{17}$—$S(O)_mR^{20}$, —$S(O)_nN(R^{21})R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^{9a}$ and $R^{9b}$ together form a group =$CR^{11}R^{12}$;

or $R^{9a}$ and $R^{9b}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$;

each $R^{10}$ is independently selected from the group consisting of halogen, cyano, azido, nitro, —SCN, $SF_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —$Si(R^{14})_2R^{13}$, —$OR^{20}$, —$OS(O)_nR^{20}$, —$SR^{20}$, —$S(O)_mR^{20}$, —$S(O)_nN(R^{21})R^{22}$, —$N(R^{21})R^{22}$, $C(=O)R^{19}$, —$C(=O)OR^{20}$, —$C(=NR^{21})R^{22}$, $C(=O)N(R^{21})R^{22}$, —$C(=S)N(R^{21})R^{22}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^{21}$—, —$CH_2CH$=N—, —CH=CH—$NR^{21}$—, —OCH=N— and —SCH=N—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy,
—$C(=O)R^{19}$, —$C(=O)OR^{20}$, —$C(=NR^{21})R^{22}$, —$C(=O)N(R^{21})R^{22}$, —$C(=S)N(R^{21})R^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^2$;

each $R^{19}$ is independently selected from the group consisting of cyano, azido, nitro, —SCN, $SF_5$, $C_3$-$C_8$-cycloalkyl, $C_3$-$C_8$-halocycloalkyl, —Si$(R^{14})_2R^{13}$, —$OR^{20}$, —$OSO_2R^{20}$, —$SR^{20}$, —S(O)$_m$$R^{20}$, —S(O)$_n$N$(R^{21})R^{22}$, —N$(R^{21})R^{22}$, —C(=O)N$(R^{21})R^{22}$, —C(=S)N$(R^{21})R^{22}$, —C(=O)$OR^{20}$, —C(=O)$R^{20}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl; and in groups —C(=O)$R^{19}$, $R^{19}$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from =$CR^{11}R^{12}$, =S(O)$_m$$R^{20}$, =S(O)$_m$N$(R^{21})R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si$(R^{14})_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3, 4 or 5;
t is 0 or 1;
and the stereoisomers, N-oxides, tautomers and agriculturally or veterinarily acceptable salts thereof.

In a further aspect, the present invention relates to substituted pyrazole-containing compounds of formula (I),

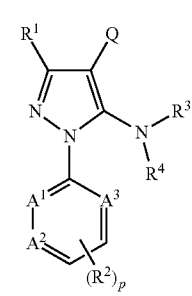

wherein
$A^1$ is N or C—$R^2$,
$A^2$ is N or C—$R^2$,
$A^3$ is N or C—$R^2$,
with the proviso that no more than two nitrogen are present in the ring that contains $A^1$, $A^2$, $A^3$;
Q is selected from phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

$R^1$ is selected from the group consisting of halogen; cyano; azido; nitro; —SCN; $SF_5$; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$; —Si$(R^{14})_2R^{13}$; —OR$^8$; —OS(O)$_n$R$^8$; —SR$^8$; —S(O)$_m$R$^8$; —S(O)$_n$N(R$^{9a}$)R$^{9b}$; —N(R$^{9a}$)R$^{9b}$; —N(R$^{9a}$)C(=O)R$^7$; C(=O)R$^7$; —C(=O)OR$^8$; —C(=NR$^{9a}$)H; —C(=NR$^{9a}$)R$^7$; —C(=O)N(R$^{9a}$)R$^{9b}$; C(=S)N(R$^{9a}$)R$^{9b}$; phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$;

$R^2$ is selected from the group consisting of hydrogen, halogen, cyano, azido, nitro, —SCN, SF$_5$, $C_1$-$C_6$-alkyl which may be partially or fully halogenated and/or may be substituted by one or more radicals R$^7$, $C_3$-$C_8$-cycloalkyl which may be partially or fully halogenated and/or may be substituted by one or more radicals R$^7$, $C_2$-$C_6$-alkenyl which may be partially or fully halogenated and/or may be substituted by one or more radicals R$^7$, $C_2$-$C_6$-alkynyl which may be partially or fully halogenated and/or may be substituted by one or more radicals R$^7$, —Si$(R^{14})_2R^{13}$, —OR$^8$, —OS(O)$_n$R$^8$, —SR$^8$, —S(O)$_m$R$^8$, —S(O)$_n$N(R$^{9a}$)R$^{9b}$, —N(R$^{9a}$)R$^{9b}$, N(R$^{9a}$)C(=O)R$^7$, —C(=O)R$^7$, —C(=O)OR$^8$, —C(=S)R$^7$, —C(=S)OR$^8$, —C(=NR$^{9a}$)R$^7$, —C(=O)N(R$^{9a}$)R$^{9n}$, —C(=S)N(R$^{9a}$)R$^{9b}$, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$;

$R^3$ is selected from the group consisting of nitro, —NR$^{9a}$R$^{9b}$, —S(O)$_n$N(R$^{9a}$)R$^{9b}$; —C(=O)N(R$^{9a}$)R$^{9b}$; —C(=S)N(R$^{9a}$)R$^{9b}$; —C(=NR$^{9a}$)—S(O)$_m$R$^8$, —P(O)G$_2$, —PG$_3$;

$R^4$ is selected from the group consisting of hydrogen, cyano, $C_1$-$C_6$-alkyl which may be partially or fully halogenated and/or may be substituted by one or more radicals R$^7$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals R$^7$, $C_3$-$C_8$-cycloalkyl which may be partially or fully halogenated and/or may be substituted by one or more radicals R$^7$, $C_3$-$C_8$-cycloalkyl-$C_1$-$C_4$-alkyl where the cycloalkyl moiety may be partially or fully halogenated and/or may be substituted by one or more radicals R$^7$, $C_2$-$C_6$-alkenyl which may be partially or fully halogenated and/or may be substituted by one or more radicals R$^7$, $C_2$-$C_6$-alkynyl which may be partially or fully halogenated and/or may be substituted by one or more radicals R$^7$, —N(R$^{9a}$)R$^{9b}$; —N(R$^{9a}$)C(=O)R$^7$; —Si$(R^{14})_2R^{13}$; —OR$^8$; —SR$^8$; —S(O)$_m$R$^8$; —S(O)$_n$N(R$^{9a}$)R$^{9b}$; —C(=O)R$^7$; —C(=O)OR$^8$; —C(=O)N(R$^{9a}$)R$^{9b}$; —C(=S)R$^7$; —C(=S)OR$^8$; —C(=S)N(R$^{9a}$)R$^{9b}$; —C(=NR$^{9a}$)—S(O)$_m$R$^8$, phenyl which may be substituted by 1, 2, 3, 4 or 5 radicals R$^{10}$, benzyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$;

or $R^3$ and $R^4$ form together with the nitrogen they are bound to a group of the formula A.1

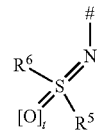

(A.1)

or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$;

provided that $R^3$ and $R^4$ do not form together with the nitrogen atom they are bound a substituted or unsubstituted piperidine, pyrrolidine or morpholine G is selected independently from each other and independently of each occurrence from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylamino, $C_1$-$C_6$-dialkylamino, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

$R^5$ and $R^6$ each independently are $C_1$-$C_{12}$-alkyl which may be partially or fully halogenated and/or may be substituted by one or more radicals R$^7$, $C_3$-$C_8$-cycloalkyl which may be partially or fully halogenated and/or may be substituted by one or more radicals R$^7$, $C_2$-$C_{12}$-alkenyl which may be partially or fully halogenated and/or may be substituted by one or more radicals R$^7$, $C_2$-$C_{12}$-alkynyl which may be partially or fully halogenated and/or may be substituted by one or more radicals R$^7$, —C(=O)R$^7$, —C(=NOR$^8$)R$^7$, —C(=NN(R$^{9a}$)R$^{9b}$)R$^7$, —C(=O)OR$^7$, —C(=O)N(R$^{9a}$)R$^{9B}$, —OC(=O)R$^7$, —OC(=O)OR$^8$, —NR$^{9a}$C(=O)R$^7$, —N[C(=O)R$^7$]$_2$, —NR$^7$C(=O)OR$^8$, —C(=O)N(R$^{9a}$)—N(R$^{9b}$)$_2$, —C(=O)NR$^{9a}$—NR$^{9b}$[C(=O)R$^7$], —NR$^{9a}$—C(=O)N(R$^{9b}$)$_2$, —NR$^{9a}$—NR$^{9b}$C(=O)R$^7$, —NR$^{9a}$—N[C(=O)R$^7$]$_2$, —N[(C=O)R$^7$]—N(R$^{9a}$)$_2$, —NR$^{9a}$—

$NR^{9b}[(C=O)OR^8]$, $-NR^{9a}[(C=O)N(R^{9b})_2]$, $-NR^{9a}[C=NR^{9b}]R^7$, $-NR^{9a}(C=NR^{9b})N(R^{9b})_2$, $-O-N(R^{9a})_2$, $-O-NR^{9a}(C=O)R^7$, $-SO_2NR^{9a}R^{9b}$, $-NR^{9a}SO_2R^8$, $-SO_2OR^8$, $-OSO_2R^8$, $-OR^8$, $-NR^{9a}R^{9b}$, $-SR^8$, $-Si(R^{14})_2R^{13}$, $-PR^{9a}R^{9b}$, $-SOR^8$, $-SO_2R^8$, or $-P(=O)_tG_2$, $-P(=O)_2G_2$;

or $R^5$ and $R^6$ together with the sulfur atom to which they are attached form a saturated, partially unsaturated or unsaturated 3- to 8-membered ring which optionally contains 1 to 4 further heteroatoms selected from oxygen, nitrogen, sulfur, which ring can be fused with one or two saturated, partially unsaturated or unsaturated 5- to 6-membered rings which may contain 1 to 4 heteroatoms selected from oxygen, nitrogen, sulfur, wherein all of the above rings are unsubstituted or substituted by any combination of 1 to 6 groups $R^{18}$;

each $R^7$ is independently selected from the group consisting of cyano, azido, nitro, $-SCN$, $SF_5$, $C_3-C_8$-cycloalkyl, $C_3-C_8$-halocycloalkyl, $-Si(R^{14})_2R^{13}$, $-OR^8$, $-OSO_2R^8$, $-SR^8$, $-S(O)_mR^8$, $-S(O)_nN(R^{9a})R^{9b}$, $-N(R^{9a})R^{9b}$, $-C(=O)N(R^{9a})R^{9b}$, $-C(=S)N(R^{9a})R^{9b}$, $-C(=O)OR^8$, $-C(=O)R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

and, in case $R^7$ is bound to a cycloalkyl group or to a heterocyclic ring, $R^7$ may additionally be selected from the group consisting of $C_1-C_6$-alkyl, $C_1-C_6$-haloalkyl, $C_1-C_6$-alkoxy-$C_1-C_6$-alkyl, $C_2-C_6$-alkenyl, $C_2-C_6$-haloalkenyl, $C_2-C_6$-alkynyl, $C_2-C_6$-haloalkynyl and benzyl which may be substituted by 1, 2, 3, 4 or 5 radicals $R^{10}$; and in groups $-C(=O)R^7$, $-C(=S)R^7$, $-C(=NR^{9a})R^7$ and $-N(R^{9a})C(=O)R^7$, $R^7$ may additionally be selected from hydrogen, halogen, $C_1-C_6$-alkyl, $C_1-C_6$-haloalkyl, $C_1-C_6$-alkoxy-$C_1-C_6$-alkyl, $C_2-C_6$-alkenyl, $C_2-C_6$-haloalkenyl, $C_2-C_6$-alkynyl, $C_2-C_6$-haloalkynyl and benzyl which may be substituted by 1, 2, 3, 4 or 5 radicals $R^{10}$;

or two geminally bound radicals $R^7$ together form a group selected from $=CR^{11}R^{12}$, $=S(O)_mR^8$, $=S(O)_mN(R^{9a})R^{9b}$, $=NR^{9a}$, $=NOR^8$ and $=NNR^{9a}R^{9b}$;

or two radicals $R^7$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^8$ is independently selected from the group consisting of hydrogen, cyano, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulfinyl, $C_1-C_6$-haloalkylsulfinyl, $C_1-C_6$-alkylsulfonyl, $C_1-C_6$-haloalkylsulfonyl, $C_3-C_8$-cycloalkyl, $C_3-C_8$-cycloalkyl-$C_1-C_4$-alkyl, $C_3-C_8$-halocycloalkyl, $C_2-C_6$-alkenyl, $C_2-C_6$-haloalkenyl, $C_2-C_6$-alkynyl, $C_2-C_6$-haloalkynyl, $-Si(R^{14})_2R^{13}$, $-SR^{20}$, $-S(O)_mR^{20}$, $-S(O)_nN(R^{9a})R^{9b}$, $-N(R^{9a})R^{9b}$, $-N=CR^{15}R^{16}$, $-C(=O)R^{17}$, $-C(=O)N(R^{9a})R^{9b}$, $-C(=S)N(R^{9a})R^{9b}$, $-C(=O)OR^{20}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; with the proviso that $R^8$ is not $C_1-C_6$-alkoxy or $C_1-C_6$-haloalkoxy if it is bound to an oxygen atom;

$R^{9a}$, $R^{9b}$ are, independently of each other and independently of each occurrence, selected from the group consisting of hydrogen, cyano, $C_1-C_6$-alkyl which may be partially or fully halogenated and/or may be substituted by one or more radicals $R^{19}$, $C_1-C_6$-alkoxy, $C_1-C_6$-haloalkoxy, $C_1-C_6$-alkylthio, $C_1-C_6$-haloalkylthio, where the alkyl moiety in the four last-mentioned radicals may be substituted by one or more radicals $R^{19}$, $C_3-C_8$-cycloalkyl which may be partially or fully halogenated and/or may be substituted by one or more radicals $R^{19}$, $C_3-C_8$-cycloalkyl-$C_1-C_4$-alkyl where the cycloalkyl moiety may be partially or fully halogenated and/or may be substituted by one or more radicals $R^{19}$, $C_2-C_6$-alkenyl which may be partially or fully halogenated and/or may be substituted by one or more radicals $R^{19}$, $C_2-C_6$-alkynyl which may be partially or fully halogenated and/or may be substituted by one or more radicals $R^{19}$, $-N(R^{21})R^{22}$; $-N(R^{21})C(=O)R^{19}$; $-Si(R^{14})_2R^{13}$; $-OR^{20}$; $-SR^{20}$; $-S(O)_mR^{20}$; $-S(O)_nN(R^{21})R^{22}$; $-C(=O)R^{19}$; $-C(=O)OR^{20}$; $-C(=O)N(R^{21})R^{22}$; $-C(=S)R^{17}$; $-C(=S)OR^{20}$; $-C(=S)N(R^{21})R^{22}$; $-C(=NR^{21})R^{17}-S(O)_mR^{20}$, $-S(O)_nN(R^{21})R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^{9a}$ and $R^{9b}$ together form a group $=CR^{11}R^{12}$;

or $R^{9a}$ and $R^{9b}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$;

each $R^{10}$ is independently selected from the group consisting of halogen, cyano, azido, nitro, $-SCN$, $SF_5$, $C_1-C_{10}$-alkyl which may be partially or fully halogenated and/or may be substituted by one or more radicals $R^{19}$, $C_3-C_8$-cycloalkyl which may be partially or fully halogenated and/or may be substituted by one or more radicals $R^{19}$, $C_2-C_{10}$-alkenyl which may be partially or fully halogenated and/or may be substituted by one or more radicals $R^{19}$, $C_2-C_{10}$-alkynyl which may be partially or fully halogenated and/or may be substituted by one or more radicals $R^{19}$, $-Si(R^{14})_2R^{13}$, $-OR^{20}$, $-OS(O)_nR^{20}$, $-SR^{20}$, $-S(O)_mR^{20}$, $-S(O)_nN(R^{21})R^{22}$, $-N(R^{21})R^{22}$, $C(=O)R^{19}$, $-C(=O)OR^{20}$, $-C(=NR^{21})R^{22}$, $-C(=O)N(R^{21})R^{22}$, $-C(=S)N(R^{21})R^{22}$, phenyl which may be substituted by 1, 2, 3, 4 or 5 radicals independently selected from halogen, cyano, nitro, $C_1-C_6$-alkyl, $C_1-C_6$-haloalkyl, $C_1-C_6$-alkoxy and $C_1-C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;
or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —S($CH_2$)S—, —$CH_2CH_2NR^{21}$—, —$CH_2$CH=N—, —CH=CH—$NR^{21}$—, —OCH=N— and —SCH=N—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —C(=O)$R^{19}$, —C(=O)$OR^{20}$, —C(=$NR^{21}$)$R^{22}$, —C(=O)N($R^{21}$)$R^{22}$, —C(=S)N($R^{21}$)$R^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^2$;

each $R^{19}$ is independently selected from the group consisting of cyano, azido, nitro, —SCN, $SF_5$, $C_3$-$C_8$-cycloalkyl, $C_3$-$C_8$-halocycloalkyl, —Si($R^{14}$)$_2R^{13}$, —$OR^{20}$, —$OSO_2R^{20}$, —$SR^{20}$, —S(O)$_mR^{20}$, —S(O)$_nN$($R^{21}$)$R^{22}$, —N($R^{21}$)$R^{22}$, —C(=O)N($R^{21}$)$R^{22}$, —C(=S)N($R^{21}$)$R^{22}$, —C(=O)$OR^{20}$, —C(=O)$R^{20}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl; and in groups —C(=O)$R^{19}$, $R^{19}$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from =$CR^{11}R^{12}$, =S(O)$_mR^{20}$, =S(O)$_mN$($R^{21}$)$R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3, 4 or 5;
t is 0 or 1;
and the stereoisomers, N-oxides and agriculturally or veterinarily acceptable salts thereof.

Such substituted pyrazole-containing compounds like the compounds according to the present invention have not yet been described, in particular not for combating animal pests. WO 2010/017902 describes insecticides of the formula (I-A)

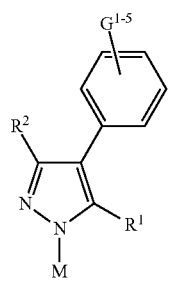

(I-A)

In this formula (I-A), M is e.g. a substituted or unsubstituted 2-pyrimidine or 1-isoquinoline. Further related insecticidal compounds are known from WO 2008/077483, WO 2010/136145, WO 2009/156090, DE 102007003036 and WO 2011/057984, however, these documents do not describe compounds having the characteristic substituents as claimed in the present invention.

Related compounds for use as fungicides are known from WO 98/27084, however, this document does not describe compounds having the characteristic substituents as claimed in the present invention.

1-heteroaryl-5-amino-3H/methyl-4-phenylpyrazoles with antibacterial activity have been described by Aggarwal et al, Bioorganic & Medicinal Chemistry (2006), 14(6), 1785-1791, however, this document does not describe compounds having the characteristic substituents as claimed in the present invention.

The invention relates to the compounds of formula (I), their stereoisomers, N-oxides, tautomers and their salts which are particularly useful for controlling invertebrate pests, in particular for controlling arthropods and nematodes and especially insects. Furthermore, the invention relates to processes for the synthesis of compounds according to the invention and to intermediate compounds for the synthesis of compounds of formula (I).

Moreover, the present invention also relates to and includes the following embodiments:

an agricultural or veterinary composition comprising at least one compound of formula (I) or a stereoisomer or agriculturally or veterinarily acceptable salt thereof, and at least one liquid and/or solid carrier.

a method for combating or controlling invertebrate pests, which method comprises contacting said pest or its food supply, habitat or breeding grounds with a pesticidally effective amount of at least one compound compound of formula (I) or a stereoisomer or agriculturally or veterinarily acceptable salt thereof, or a composition as defined herein.

a method for protecting growing plants from attack or infestation by invertebrate pests, which method comprises contacting a plant, or soil or water in which the plant is growing, with a pesticidally effective amount of at least one compound compound of formula (I) or a stereoisomer or agriculturally or veterinarily acceptable salt thereof, or a composition as defined herein.

a method for the protection of plant propagation material, especially seeds, from soil insects and of the seedlings' roots and shoots from soil and foliar insects comprising contacting the plant propagation material respectively seeds before sowing and/or after pregermination with at least one compound compound of formula (I) or a stereoisomer or agriculturally or veterinarily acceptable salt thereof, or a composition as defined herein.

seed comprising a compound of formula (I) or a stereoisomer or agriculturally or veterinarily acceptable salt thereof, in an amount of from 0.1 g to 10 kg per 100 kg of the plant propagation material.

use of a compound compound of formula (I) or a stereoisomer or agriculturally or veterinarily acceptable salt thereof, or a composition as defined in claim yy for combating or controlling invertebrate pests of the group of insects, arachnids or nematodes.

use of a compound of formula (I) or a stereoisomer or agriculturally or veterinarily acceptable salt thereof, or a composition as defined in claim yy for protecting growing plants from attack or infestation by invertebrate pests.

use of a compound of formula (I) or a stereoisomer or veterinarily acceptable salt thereof or a composition as defined herein for combating or controlling invertebrate parasites in and on animals.

a method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasiticidally effective amount of a compound compound of formula (I) or a stereoisomer or veterinarily acceptable salt thereof or a composition as defined in claim herein.

a compound compound of formula (I) or a stereoisomer or veterinarily acceptable salt thereof for use as a medicament.

a compound compound of formula (I) or a stereoisomer or veterinarily acceptable salt thereof for use in the treatment, control, prevention or protection of animals against infestation or infection by parasites.

Depending on the substitution pattern, the compounds of the formula (I) may have one or more centers of chirality, in which case they are present as mixtures of enantiomers or diastereomers. The invention provides both the pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

The compounds of the formula (I) may be present in the form of their N-oxides. The term "N-oxide" includes any compound of the present invention which has at least one tertiary nitrogen atom that is oxidized to an N-oxide moiety. N-oxides of compounds (I) can in particular be prepared by oxidizing the ring nitrogen atom(s) of the pyridine ring and/or the pyrazole ring with a suitable oxidizing agent, such as peroxo carboxylic acids or other peroxides.

Depending on the substitution pattern, the compounds of the formula (I) may be present in the form of their tautomers. Hence, the invention also relates to the tautomers of the formula (I) and the stereoisomers, salts and N-oxides of said tautomers. For instance, if $R^4$ is H and $R^3$ is —N=N—$R^{9a}$, the compounds of formula (I) may be present in the below tautomeric forms.

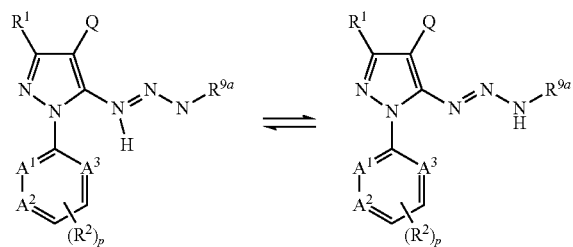

The compounds of the present invention may be amorphous or may exist in one ore more different crystalline states (polymorphs) which may have different macroscopic properties such as stability or show different biological properties such as activities. The present invention includes both amorphous and crystalline compounds of formula (I), their enantiomers or diastereomers, mixtures of different crystalline states of the respective compound of formula (I), its enantiomers or diastereomers, as well as amorphous or crystalline salts thereof. Salts of the compounds of the present invention are preferably agriculturally and veterinarily acceptable salts. They can be formed in a customary method, e.g. by reacting the compound with an acid if the compound of the present invention has a basic functionality or by reacting the compound with a suitable base if the compound of the present invention has an acidic functionality.

Suitable agriculturally acceptable salts are especially the salts of those cations or the acid addition salts of those acids whose cations and anions, respectively, do not have any adverse effect on the pesticidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of the present invention with an acid of the corresponding anion, preferably with hydrochloric acid, hydrobromic acid, sulfuric acid, phosphoric acid or nitric acid.

Veterinarily acceptable salts of the compounds of the present invention encompass the salts of those cations or the acid addition salts which are known and accepted in the art for the formation of salts for veterinary use. Suitable acid addition salts, e.g. formed by compounds of the present invention containing a basic nitrogen atom, e.g. an amino group, include salts with inorganic acids, for example hydrochlorides, sulfates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

In one embodiment, the compounds according to the invention comprise the stereoisomers, N-oxides and agriculturally or veterinarily acceptable salts thereof.

In another embodiment, the compounds according to the invention comprise the stereoisomers, N-oxides, tautomers and agriculturally or veterinarily acceptable salts thereof The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine. A partially or fully halogenated radical is termed below also "halo-radical". For example, partially or fully halogenated alkyl is also termed haloalkyl.

The term "alkyl" as used herein (and in the alkyl moieties of other groups comprising an alkyl group, e.g. alkoxy, alkylcarbonyl, alkylthio, alkylsulfinyl, alkylsulfonyl and alkoxyalkyl) denotes in each case a straight-chain or branched alkyl group having usually from 1 to 12 or 1 to 10 carbon atoms, frequently from 1 to 6 carbon atoms, preferably 1 to 4 carbon atoms and in particular from 1 to 3 carbon atoms. Examples of $C_1$-$C_4$-alkyl are methyl, ethyl, n-propyl, isopropyl, n-butyl, 2-butyl(sec-butyl), isobutyl and tert-butyl. Examples for $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl, 2-propylpentyl, nonyl, decyl, 2-propylheptyl and 3-propylheptyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy, haloalkylthio, haloalkylcarbonyl, haloalkylsulfonyl and haloalkylsulfinyl) denotes in each case a straight-chain or branched alkyl group having usually from 1 to 10 carbon atoms ("$C_1$-$C_{10}$-haloalkyl"), frequently from 1 to 6 carbon atoms ("$C_1$-$C_6$-haloalkyl"), more frequently 1 to 4 carbon atoms ("$C_1$-$C_{10}$-haloalkyl"), wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl. Halomethyl is methyl in which 1, 2 or 3 of the hydrogen atoms are replaced by halogen atoms. Examples are bromomethyl, chloromethyl, dichloromethyl, trichloromethyl, fluoromethyl, difluoromethyl, trifluoromethyl, chlorofluoromethyl, dichlorofluoromethyl, chlorodifluoromethyl and the like. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Examples for $C_1$-$C_2$-haloalkyl are, apart those mentioned for $C_1$-$C_2$-fluoroalkyl, chloromethyl, dichloromethyl, trichloromethyl, bromomethyl, chlorofluoromethyl, dichlorofluoromethyl, chlorodifluoromethyl, 1-chloroethyl, 2-chloroethyl, 2,2,-dichloroethyl, 2,2,2-trichloroethyl, 2-chloro-2-fluoroethyl, 2-chloro-2,2-difluoroethyl, 2,2-dichloro-2-fluoroethyl, 1-bromoethyl, and the like. Examples for $C_1$-$C_4$-haloalkyl are, apart those mentioned for $C_1$-$C_2$-haloalkyl, 1-fluoropropyl, 2-fluoropropyl, 3-fluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms ("$C_3$-$C_{10}$-cycloalkyl"), preferably 3 to 8 carbon atoms ("$C_3$-$C_8$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

The term "cycloalkylene" (or cycloalkanediyl) as used herein in each case denotes an cycloalkyl radical as defined above, wherein one hydrogen atom at any position of the carbon backbone is replaced by one further binding site, thus forming a bivalent moiety.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, preferably 3 to 8 carbon atoms or in particular 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkyl-alkyl" used herein denotes a cycloalkyl group, as defined above, which is bound to the remainder of the molecule via an alkylene group. The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "alkenyl" as used herein denotes in each case a monounsaturated straight-chain or branched hydrocarbon radical having usually 2 to 10 ("$C_2$-$C_{10}$-alkenyl"), preferably 2 to 6 carbon atoms ("$C_2$-$C_6$-alkenyl"), in particular 2 to 4 carbon atoms ("$C_2$-$C_4$-alkenyl"), and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl- 3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "alkenylene" (or alkenediyl) as used herein in each case denotes an alkenyl radical as defined above, wherein one hydrogen atom at any position of the carbon backbone is replaced by one further binding site, thus forming a bivalent moiety.

The term "haloalkenyl" as used herein, which may also be expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 6 ("$C_2$-$C_6$-haloalkenyl") or 2 to 4 ("$C_2$-$C_4$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes unsaturated straight-chain or branched hydrocarbon radicals having usually 2 to 10 ("$C_2$-$C_{10}$-alkynyl"), frequently 2 to 6 ("$C_2$-$C_6$-alkynyl"), preferably 2 to 4 carbon atoms ("$C_2$-$C_4$-alkynyl") and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "alkynylene" (or alkynediyl) as used herein in each case denotes an alkynyl radical as defined above, wherein one hydrogen atom at any position of the carbon backbone is replaced by one further binding site, thus forming a bivalent moiety.

The term "haloalkynyl" as used herein, which is also expressed as "alkynyl which may be substituted by halogen", refers to unsaturated straight-chain or branched hydrocarbon radicals having is usually 3 to 10 carbon atoms ("$C_2$-$C_{10}$-haloalkynyl"), frequently 2 to 6 ("$C_2$-$C_6$-haloalkynyl"), preferably 2 to 4 carbon atoms ("$C_2$-$C_4$-haloalkynyl"), and one or two triple bonds in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 10 carbon atoms ("$C_1$-$C_{10}$-alkoxy"), frequently from 1 to 6 carbon atoms ("$C_1$-$C_6$-alkoxy"), preferably 1 to 4 carbon atoms ("$C_1$-$C_4$-alkoxy"), which is bound to the remainder of the molecule via an oxygen atom. $C_1$-$C_2$-Alkoxy is methoxy or ethoxy. $C_1$-$C_4$-Alkoxy is additionally, for example, n-propoxy, 1-methylethoxy(isopropoxy), butoxy, 1-methylpropoxy(sec-butoxy), 2-methylpropoxy(isobutoxy) or 1,1-dimethylethoxy(tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof. The term "haloalkoxy" as used herein denotes in each case a straight-chain or branched alkoxy group, as defined above, having from 1 to 10 carbon atoms ("$C_1$-$C_{10}$-haloalkoxy"), frequently from 1 to 6 carbon atoms ("$C_1$-$C_6$-haloalkoxy"), preferably 1 to 4 carbon atoms ("$C_1$-$C_4$-haloalkoxy"), more preferably 1 to 3 carbon atoms ("$C_1$-$C_3$-haloalkoxy"), wherein the hydrogen atoms of this group are partially or totally replaced with halogen atoms, in particular fluorine atoms. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "alkoxyalkyl" as used herein denotes in each case alkyl usually comprising 1 to 6 carbon atoms, preferably 1 to 4 carbon atoms, wherein 1 carbon atom carries an alkoxy radical usually comprising 1 to 10, frequently 1 to 6, in particular 1 to 4, carbon atoms as defined above. "$C_1$-$C_6$-Alkoxy-$C_1$-$C_6$-alkyl" is a $C_1$-$C_6$-alkyl group, as defined above, in which one hydrogen atom is replaced by a $C_1$-$C_6$-alkoxy group, as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "haloalkoxy-alkyl" as used herein denotes in each case alkyl as defined above, usually comprising 1 to 6 carbon atoms, preferably 1 to 4 carbon atoms, wherein 1 carbon atom carries an haloalkoxy radical as defined above, usually comprising 1 to 10, frequently 1 to 6, in particular 1 to 4, carbon atoms as defined above. Examples are fluoromethoxymethyl, difluoromethoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethoxymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl or alkyl-S—)" as used herein denotes in each case a straight-chain or branched saturated alkyl group as defined above, usually comprising 1 to 10 carbon atoms ("$C_1$-$C_{10}$-alkylthio"), frequently comprising 1 to 6 carbon atoms ("$C_1$-$C_6$-alkylthio"), preferably 1 to 4 carbon atoms ("$C_1$-$C_4$-alkylthio"), which is attached via a sulfur atom at any position in the alkyl group. $C_1$-$C_2$-Alkylthio is methylthio or ethylthio. $C_1$-$C_4$-Alkylthio is additionally, for example, n-propylthio, 1-methylethylthio(isopropylthio), butylthio, 1-methylpropylthio(sec-butylthio), 2-methylpropylthio(isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "haloalkylthio" as used herein refers to an alkylthio group as defined above wherein the hydrogen atoms are partially or fully substituted by fluorine, chlorine, bromine and/or iodine. $C_1$-$C_2$-Haloalkylthio is, for example, $SCH_2F$, $SCHF_2$, $SCF_3$, $SCH_2Cl$, $SCHC_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The terms "alkylsulfinyl" and "$S(O)_n$-alkyl" (wherein n is 1) are equivalent and, as used herein, denote an alkyl group, as defined above, attached via a sulfinyl [S(O)] group. For example, the term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" refers to a $C_1$-$C_4$-alkyl group, as defined above, attached via a sulfinyl [S(O)] group. The term "$C_1$-$C_6$-alkylsulfinyl" refers to a $C_1$-$C_6$-alkyl group, as defined above, attached via a sulfinyl [S(O)] group. $C_1$-$C_2$-alkylsulfinyl is methylsulfinyl or ethylsulfinyl. $C_1$-$C_4$-alkylsulfinyl is additionally, for example, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl) or 1,1-dimethylethylsulfinyl(tert-butylsulfinyl). $C_1$-$C_6$-alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The terms "alkylsulfonyl" and "$S(O)_n$-alkyl" (wherein n is 2) are equivalent and, as used herein, denote an alkyl group, as defined above, attached via a sulfonyl [$S(O)_2$] group. The term "$C_1$-$C_2$-alkylsulfonyl" refers to a $C_1$-$C_2$-alkyl group, as defined above, attached via a sulfonyl [$S(O)_2$] group. The term "$C_1$-$C_4$-alkylsulfonyl" refers to a $C_1$-$C_4$-alkyl group, as defined above, attached via a sulfonyl [$S(O)_2$] group. The term "$C_1$-$C_6$-alkylsulfonyl" refers to a $C_1$-$C_6$-alkyl group, as defined above, attached via a sulfonyl [$S(O)_2$] group. $C_1$-$C_2$-alkylsulfonyl is methylsulfonyl or ethylsulfonyl. $C_1$-$C_4$-alkylsulfonyl is additionally, for example, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl) or 1,1-dimethylethylsulfonyl(tert-butylsulfonyl). $C_1$-$C_6$-alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "alkylamino" as used herein denotes in each case a group —NHR, wherein R is a straight-chain or branched alkyl group usually having from 1 to 6 carbon atoms ("$C_1$-$C_6$-alkylamino"), preferably 1 to 4 carbon atoms ("$C_1$-$C_4$-alkylamino"). Examples of $C_1$-$C_6$-alkylamino are methylamino, ethylamino, n-propylamino, isopropylamino, n-butylamino, 2-butylamino, iso-butylamino, tert-butylamino, and the like.

The term "dialkylamino" as used herein denotes in each case a group-NRR', wherein R and R', independently of each other, are a straight-chain or branched alkyl group each usually having from 1 to 6 carbon atoms ("di-($C_1$-$C_6$-alkyl)-amino"), preferably 1 to 4 carbon atoms ("di-($C_1$-$C_4$-alkyl)-amino"). Examples of a di-($C_1$-$C_6$-alkyl)-amino group are dimethylamino, diethylamino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The term "alkylaminosulfonyl" as used herein denotes in each case a straight-chain or branched alkylamino group as defined above, which is bound to the remainder of the molecule via a sulfonyl [$S(O)_2$] group. Examples of an alkylaminosulfonyl group are methylaminosulfonyl, ethylaminosulfonyl, n-propylaminosulfonyl, isopropylaminosulfonyl, n-butylaminosulfonyl, 2-butylaminosulfonyl, iso-butylaminosulfonyl, tert-butylaminosulfonyl, and the like.

The term "dialkylaminosulfonyl" as used herein denotes in each case a straight-chain or branched alkylamino group as defined above, which is bound to the remainder of the molecule via a sulfonyl [$S(O)_2$] group. Examples of an dialkylaminosulfonyl group are dimethylaminosulfonyl, diethylaminosulfonyl, dipropylaminosulfonyl, dibutylaminosulfonyl, methyl-ethyl-aminosulfonyl, methyl-propyl-aminosulfonyl, methyl-isopropylaminosulfonyl, methyl-butyl-aminosulfonyl, methyl-isobutyl-aminosulfonyl, ethyl-propyl-aminosulfonyl, ethyl-isopropylaminosulfonyl, ethyl-butyl-aminosulfonyl, ethyl-isobutyl-aminosulfonyl, and the like.

The suffix "-carbonyl" in a group denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl.

The term "het(ero)aryl" as used herein refers to a mono-, bi- or tricyclic heteroaromatic hydrocarbon radical, preferably to a monocyclic heteroaromatic radical, such as pyridyl, pyrimidyl and the like.

The term "3-, 4-, 5-, 6- or 7-membered saturated, partially unsaturated or fully unsaturated heterocyclic ring containing 1, 2 or 3 heteroatoms or heteroatom groups selected from N, O, S, NO, SO and $SO_2$, as ring members" [wherein "fully unsaturated" also includes "aromatic"] as used herein denotes monocyclic radicals, the monocyclic radicals being saturated, partially unsaturated or fully unsaturated (including aromatic). Unsaturated rings contain at least one C—C and/or C—N and/or N—N double bond(s). Fully unsaturated rings contain as many conjugated C—C and/or C—N and/or N—N double bonds as allowed by the ring size. Fully unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4- dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

A 3-, 4-, 5-, 6- or 7-membered fully unsaturated (including aromatic) heterocyclic ring is e.g. a 5- or 6-membered fully unsaturated (including aromatic) heterocyclic ring. Examples are: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl.

When $R^{9a}$ and $R^{9b}$, together with the nitrogen atom to which they are bound form a 3-, 4-, 5-, 6- or 7-membered saturated, partially unsaturated or fully unsaturated heterocyclic ring which may additionally contain 1 or 2 further heteroatoms or heteroatom groups selected from N, O, S, NO, SO and $SO_2$, as ring members, this is an N-bound heterocyclic ring which apart the nitrogen ring atom may additionally contain 1, 2, 3 or 4 further heteroatoms or heteroatom groups selected from N, O, S, NO, SO and $SO_2$, as ring members. Examples are aziridin-1-yl, azetidin-1-yl, pyrrolidine-1-yl, pyrazolidin-1-yl, imidazolin-1-yl, oxazolidin-3-yl, isoxazolidin-3-yl, thiazolidin-1-yl, isothiazolidin-1-yl, triazolidin-1-yl, piperdon-1-yl, piperazine-1-yl, morpholin-4-yl, thiomorpholin-1-yl, 1,1-dioxothiomorpholin-4-yl, pyrrolin-1-yl, pyrrolin-1-yl, imidazolin-1-yl, dihydropyridin-1-yl, tetrahydropyridin-1-yl, pyrrol-1-yl, pyrazo-1-yl, imidazol-1-yl and the like.

Preferences

The remarks made below as to preferred embodiments of the variables (substituents) of the compounds of formulae (I) and (I-I) are valid on their own as well as preferably in combination with each other, as well as in combination with the stereoisomers or salts thereof, and, where applicable, as well as concerning the uses and methods according to the invention and the composition according to the invention.

Preferred compounds according to the invention are compounds of formulae (I) or a stereoisomer or salt thereof, wherein the salt is an agriculturally or veterinarily acceptable salt.

Preferred are compounds of formula (I), wherein
$A^1$ and $A^3$ are N, and
$A^2$ is C—$R^2$.

Further preferred are compounds of formula (I), wherein
Q is phenyl which may be substituted by 1, 2, 3, 4 or 5 radicals $R^{10}$.

Further preferred are compounds of formula (I), wherein the compounds have the general formula (I-I)

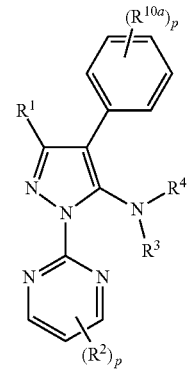

(I-I)

wherein
$R^1$ is selected from the group consisting of halogen; cyano; azido; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$;
each $R^{10a}$ is independently selected from the group as defined for $R^{10}$ in any of the preceding claims;
p is independently from each occurrence 0, 1, 2 or 3;
$R^2$, $R^3$, $R^4$ are as defined above.

Further preferred are compounds of formula (I), wherein
$R^1$ is selected from the group consisting of halogen; $C_1$-$C_6$-alkyl which may be partially or fully halogenated; $C_3$-$C_8$-cycloalkyl which may be partially or fully halogenated; $C_2$-$C_6$-alkenyl which may be partially or fully halogenated; $C_2$-$C_6$-alkynyl which may be partially or fully halogenated;
$R^2$ is selected from the group consisting of hydrogen, halogen, cyano, azido, $C_1$-$C_6$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$.

Further preferred are compounds of formula (I), wherein
$R^1$ is $C_1$-$C_6$-alkyl which may be partially or fully halogenated;
$R^2$ consisting of hydrogen, halogen, $C_1$-$C_6$-alkyl which may be partially or fully halogenated; $C_3$-$C_8$-cycloalkyl which may be partially or fully halogenated.

Especially preferred are compounds of formula (I), wherein
$R^1$ is methyl, trifluoromethyl, difluoromethyl or fluoromethyl;
$R^2$ is selected from the group consisting of hydrogen, halogen, $C_1$-$C_6$-alkyl.

Especially preferred are compounds of formula (I), wherein
$R^1$ is methyl, trifluoromethyl, difluoromethyl or fluoromethyl;
$R^2$ is hydrogen.

Especially preferred are compounds of formula (Ia.2-CF3)

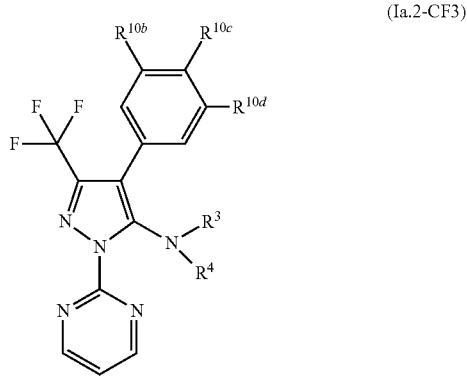

(Ia.2-CF3)

in which $R^3$, $R^4$, $R^{10b}$, $R^{10c}$ and $R^{10d}$ are as defined herein.

Further preferred are compounds of formula (I), wherein
each $R^{10}$ and $R^{10a}$ is independently selected from the group consisting of halogen, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$;

or two radicals $R^{10}$ and/or $R^{10a}$ bound on adjacent atoms together form a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$) O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S) SCH$_2$—, —S(CH$_2$)S—, —CH$_2$CH$_2$NR$^{21}$—, —CH$_2$CH=N—, —CH=CH—NR$^{21}$—, —OCH=N— and —SCH=N—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more CH$_2$ groups of the above groups may be replaced by a C=O group.

Further preferred are compounds of formula (I), wherein
$R^3$ is selected from the group consisting of nitro, —NR$^{9a}$R$^{9b}$; —S(O)$_n$N(R$^{9a}$)R$^{9b}$; —C(=O)N(R$^{9a}$)R$^{9b}$; —C(=S)N(R$^{9a}$)R$^{9b}$; —C(=NR$^{9a}$)—S(O)$_m$R$^8$, —P(O) G$_2$, —PG$_3$, —N=N—R$^{9a}$;

$R^4$ is selected from the group consisting of hydrogen, cyano, C$_1$-C$_6$-alkyl which may be partially or fully halogenated and/or may be substituted by one or more radicals $R^7$, C$_1$-C$_6$-alkoxy, C$_1$-C$_6$-haloalkoxy, C$_1$-C$_6$-alkylthio, C$_1$-C$_6$-haloalkylthio, where the alkyl moiety in the four last-mentioned radicals may be substituted by one or more radicals $R^7$, C$_3$-C$_8$-cycloalkyl which may be partially or fully halogenated and/or may be substituted by one or more radicals $R^7$, C$_3$-C$_8$-cycloalkyl-C$_1$-C$_4$-alkyl where the cycloalkyl moiety may be partially or fully halogenated and/or may be substituted by one or more radicals $R^7$, C$_2$-C$_6$-alkenyl which may be partially or fully halogenated and/or may be substituted by one or more radicals $R^7$, C$_2$-C$_6$-alkynyl which may be partially or fully halogenated and/or may be substituted by one or more radicals $R^7$, —N(R$^{9a}$)R$^{9b}$; —N(R$^{9a}$)C(=O)R$^7$; —Si(R$^{14}$)$_2$R$^{13}$; —OR$^8$; —SR$^8$; —S(O)$_m$R$^8$; —S(O)$_n$N (R$^{9a}$)R$^{9b}$; —C(=O)R$^7$; —C(=O)OR$^8$; —C(=O)N (R$^{9a}$)R$^{9b}$; —C(=S)R$^7$; —C(=S)OR$^8$; —C(=S)N (R$^{9a}$)R$^{9b}$; —C(=NR$^{9a}$)—S(O)$_m$R$^8$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

provided that $R^3$ and $R^4$ do not form together with the nitrogen atom they are bound a substituted or unsubstituted piperidine, pyrrolidine or morpholine.

Further preferred are compounds of formula (I), wherein $R^3$ and $R^4$ form together with the nitrogen they are bound to a group of the formula A.1

(A.1)

in which $R^5$ and $R^6$ are as defined above.

Further preferred are compounds of formula (I), wherein $R^5$ and $R^6$ each independently are C$_1$-C$_{12}$-alkyl which may be partially or fully halogenated and/or substituted by one or more C$_1$-C$_6$-alkoxy groups; or C$_3$-C$_8$-cycloalkyl.

Also preferred are compounds of formula (I), (Ia.2) or (Ia.2-CF3), wherein
$R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$; provided that $R^3$ and $R^4$ do not form together with the nitrogen atom they are bound a substituted or unsubstituted piperidine, pyrrolidine or morpholine.

Further preferred are compounds of formula (I), (Ia.2) or (Ia.2-CF3), wherein $R^3$ and $R^4$ form together with the nitrogen atom they are bound a pyrrol ring.

Also preferred are compounds of formula (I), (Ia.2) or (Ia.2-CF3), wherein
$R^3$ is —P(O)G$_2$, —PG$_3$; wherein G is as defined herein;
$R^4$ is hydrogen.

Also preferred are compounds of formula (I), (Ia.2) or (Ia.2-CF3), wherein
$R^3$ is —N=N—R$^{9a}$, wherein R$^{9a}$ is as defined herein;
$R^4$ is hydrogen;
and their tautomers.

Also preferred are compounds of formula (I), (Ia.2) or (Ia.2-CF3), wherein
$R^4$ is —C=O— $R^7$;
wherein $R^7$ is as defined herein, preferably $C_1$-$C_4$-alkyl, preferably methyl.

Also preferred are compounds of formula (I), (Ia.2) or (Ia.2-CF3), wherein
$R^3$ and $R^4$ are identical.

Also preferred are compounds of formula (I), (Ia.2) or (Ia.2-CF3), wherein
$R^3$ and $R^4$ are identical and are —C(=O)N($R^{9a}$)$R^{9b}$.

Further preferred are compounds of formula (Ia.2), wherein
$R^{10b}$ is methyl, trifluoromethyl, difluoromethyl or fluoromethyl,
$R^{10c}$ is hydrogen and
$R^{10d}$ is chloro.

Examples of preferred compounds are the individual compounds compiled in the tables below. Moreover, the meanings mentioned below for the individual variables in the tables are per se, independently of the combination in which they are mentioned, a particularly preferred embodiment of the substituents in question.

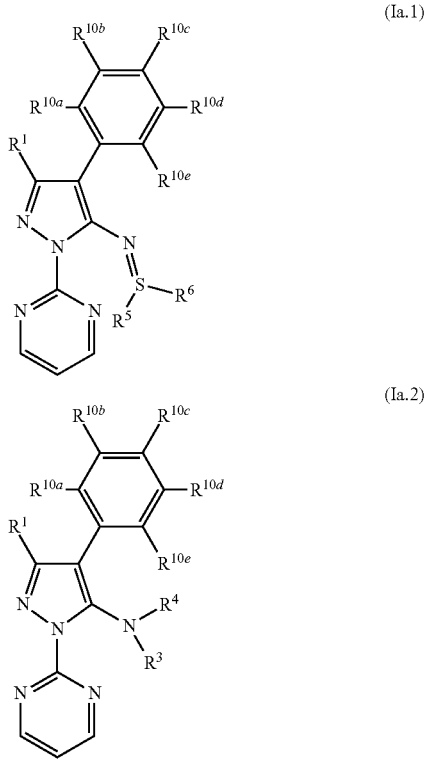

Table 1 Compounds of the formula Ia.1 in which $R^1$ is trifluoromethyl, $R^5$ and $R^6$ are both methyl, and the combination of $R^{10a}$, $R^{10b}$, $R^{10c}$, $R^{10d}$ and $R^{10e}$ for a compound corresponds in each case to one row of Table A Table 2 Compounds of the formula Ia.1 in which $R^1$ is trifluoromethyl, $R^5$ and $R^6$ are both ethyl, and the combination of $R^{10a}$, $R^{10b}$, $R^{10c}$, $R^{10d}$ and $R^{10e}$ for a compound corresponds in each case to one row of Table A Table 3 Compounds of the formula Ia.1 in which $R^1$ is trifluoromethyl, $R^5$ and $R^6$ are both isopropyl, and the combination of $R^{10a}$, $R^{10b}$, $R^{10c}$, $R^{10d}$ and $R^{10e}$ for a compound corresponds in each case to one row of Table A Table 4 Compounds of the formula Ia.1 in which $R^1$ is trifluoromethyl, $R^5$ and $R^6$ are both propyl, and the combination of $R^{10a}$, $R^{10b}$, $R^{10c}$, $R^{10d}$ and $R^{10e}$ for a compound corresponds in each case to one row of Table A Table 5 Compounds of the formula Ia.1 in which $R^1$ is trifluoromethyl, $R^5$ and $R^6$ are both n-butyl, and the combination of $R^{10a}$, $R^{10b}$, $R^{10c}$, $R^{10d}$ and $R^{10e}$ for a compound corresponds in each case to one row of Table A Table 6 Compounds of the formula Ia.1 in which $R^1$ is trifluoromethyl, $R^5$ and $R^6$ are both 2-butyl, and the combination of $R^{10a}$, $R^{10b}$, $R^{10c}$, $R^{10d}$ and $R^{10e}$ for a compound corresponds in each case to one row of Table A Table 7 Compounds of the formula Ia.1 in which $R^1$ is trifluoromethyl, $R^5$ and $R^6$ are both iso-butyl, and the combination of $R^{10a}$, $R^{10b}$, $R^{10c}$, $R^{10d}$ and $R^{10e}$ for a compound corresponds in each case to one row of Table A Table 8 Compounds of the formula Ia.1 in which $R^1$ is trifluoromethyl, $R^5$ and $R^6$ are both pentyl, and the combination of $R^{10a}$, $R^{10b}$, $R^{10c}$, $R^{10d}$ and $R^{10e}$ for a compound corresponds in each case to one row of Table A Table 9 Compounds of the formula Ia.1 in which $R^1$ is trifluoromethyl, $R^5$ and $R^6$ are both hexyl, and the combination of $R^{10a}$, $R^{10b}$, $R^{10c}$, $R^{10d}$ and $R^{10e}$ for a compound corresponds in each case to one row of Table A Table 10 Compounds of the formula Ia.1 in which $R^1$ is trifluoromethyl, $R^5$ and $R^6$ are both 2-ethylhexyl, and the combination of $R^{10a}$, $R^{10b}$, $R^{10c}$, $R^{10d}$ and $R^{10e}$ for a compound corresponds in each case to one row of Table A Table 11 Compounds of the formula Ia.1 in which $R^1$ is trifluoromethyl, $R^5$ and $R^6$ are both 2-hydroxyethyl, and the combination of $R^{10a}$, $R^{10b}$, $R^{10c}$, $R^{10d}$ and $R^{10e}$ for a compound corresponds in each case to one row of Table A Table 12 Compounds of the formula Ia.1 in which $R^1$ is trifluoromethyl, $R^5$ and $R^6$ are both cyclopropyl, and the combination of $R^{10a}$, $R^{10b}$, $R^{10c}$, $R^{10d}$ and $R^{10e}$ for a compound corresponds in each case to one row of Table A Table 13 Compounds of the formula Ia.1 in which $R^1$ is trifluoromethyl, $R^5$ and $R^6$ are both 1-cyclopropylethyl, and the combination of $R^{10a}$, $R^{10b}$, $R^{10c}$, $R^{10d}$ and $R^{10e}$ for a compound corresponds in each case to one row of Table A Table 14 Compounds of the formula Ia.1 in which $R^1$ is trifluoromethyl, $R^5$ and $R^6$ are both 2-cyclopropylethyl, and the combination of $R^{10a}$, $R^{10b}$, $R^{10c}$, $R^{10d}$ and $R^{10e}$ for a compound corresponds in each case to one row of Table A Table 15 Compounds of the formula Ia.1 in which $R^1$ is trifluoromethyl, $R^5$ and $R^6$ are both cyclopropylmethyl, and the combination of $R^{10a}$, $R^{10b}$, $R^{10c}$, $R^{10d}$ and $R^{10e}$ for a compound corresponds in each case to one row of Table A Table 16 Compounds of the formula Ia.1 in which $R^1$ is trifluoromethyl, $R^5$ and $R^6$ form a butylene ring, and the combination of $R^{10a}$, $R^{10b}$, $R^{10c}$, $R^{10d}$ and $R^{10e}$ for a compound corresponds in each case to one row of Table A Table 17 Compounds of the formula Ia.1 in which $R^1$ is trifluoromethyl, $R^5$ and $R^6$ form a pentylene ring, and the combination of $R^{10a}$, $R^{10b}$, $R^{10c}$, $R^{10d}$ and $R^{10e}$ for a compound corresponds in each case to one row of Table A Table 18 Compounds of the formula Ia.2 in which $R^1$ is trifluoromethyl, $R^4$ is hydrogen, $R^3$ is $NH_2$ and the combination of $R^{10a}$, $R^{10b}$, $R^{10c}$, $R^{10d}$ and $R^{10e}$ for a compound corresponds in each case to one row of Table A Table 19 Compounds of the formula Ia.2 in which $R^1$ is trifluoromethyl, $R^4$ is hydrogen, $R^3$ is $NHCH_3$ and the combination of $R^{10a}$, $R^{10b}$, $R^{10c}$, $R^{10d}$ and $R^{10e}$ for a compound corresponds in each case to one row of Table A Table 20 Compounds of the formula Ia.2 in which $R^1$ is trifluoromethyl, $R^4$ is hydrogen, $R^3$ is $NHNHC_6H_5$ and the combination of $R^{10a}$, $R^{10b}$, $R^{10c}$, $R^{10d}$ and $R^{10e}$ for a compound corresponds in each case to one row of Table A Table 21 Compounds of the formula Ia.2 in which $R^1$ is trifluoromethyl, $R^4$ is hydrogen, $R^3$ is NHNHCH$_3$ and the combination of $R^{10a}$, $R^{10b}$, $R^{10c}$, $R^{10d}$ and $R^{10e}$ for a compound corresponds in each case to one row of Table A Table 22 Compounds of the formula Ia.2 in which $R^1$ is trifluoromethyl, $R^4$ is hydrogen, $R^3$ is NHNHCH$_2$CH$_3$ and the combination of $R^{10a}$, $R^{10b}$, $R^{10c}$, $R^{10d}$ and $R^{10e}$ for a compound corresponds in each case to one row of Table A Table 23 Compounds of the formula Ia.2 in which $R^1$ is trifluoromethyl, $R^4$ is hydrogen, $R^3$ is SO$_2$NH$_2$ and the combination of $R^{10a}$, $R^{10b}$, $R^{10c}$, $R^{10d}$ and $R^{10e}$ for a compound corresponds in each case to one row of Table A Table 24 Compounds of the formula Ia.2 in which $R^1$ is trifluoromethyl, $R^4$ is hydrogen, $R^3$ is SO$_2$NHCH$_3$ and the combination of $R^{10a}$, $R^{10b}$, $R^{10c}$, $R^{10d}$ and $R^{10e}$ for a compound corresponds in each case to one row of Table A Table 25 Compounds of the formula Ia.2 in which $R^1$ is trifluoromethyl, $R^4$ is hydrogen, $R^3$ is SO$_2$NHCH$_2$CH$_3$ and the combination of $R^{10a}$, $R^{10b}$, $R^{10c}$, $R^{10d}$ and $R^{10e}$ for a compound corresponds in each case to one row of Table A Table 26 Compounds of the formula Ia.2 in which $R^1$ is trifluoromethyl, $R^4$ is hydrogen, $R^3$ is SO$_2$N(CH$_3$)$_2$ and the combination of $R^{10a}$, $R^{10b}$, $R^{10c}$, $R^{10d}$ and $R^{10e}$ for a compound corresponds in each case to one row of Table A Table 27 Compounds of the formula Ia.2 in which $R^1$ is trifluoromethyl, $R^4$ is hydrogen, $R^3$ is C(=O)NH$_2$ and the combination of $R^{10a}$, $R^{10b}$, $R^{10c}$, $R^{10d}$ and $R^{10e}$ for a compound corresponds in each case to one row of Table A Table 28 Compounds of the formula Ia.2 in which $R^1$ is trifluoromethyl, $R^4$ is hydrogen, $R^3$ is C(=O)NHCH$_3$ and the combination of $R^{10a}$, $R^{10b}$, $R^{10c}$, $R^{10d}$ and $R^{10e}$ for a compound corresponds in each case to one row of Table A Table 29 Compounds of the formula Ia.2 in which $R^1$ is trifluoromethyl, $R^4$ is hydrogen, $R^3$ is C(=O)NHCH$_2$CH$_3$ and the combination of $R^{10a}$, $R^{10b}$, $R^{10c}$, $R^{10d}$ and $R^{10e}$ for a compound corresponds in each case to one row of Table A Table 30 Compounds of the formula Ia.2 in which $R^1$ is trifluoromethyl, $R^4$ is hydrogen, $R^3$ is C(=O)N(CH$_3$)$_2$ and the combination of $R^{10a}$, $R^{10b}$, $R^{10c}$, $R^{10d}$ and $R^{10e}$ for a compound corresponds in each case to one row of Table A Table 31 Compounds of the formula Ia.2 in which $R^1$ is trifluoromethyl, $R^4$ is hydrogen, $R^3$ is C(=S)NH$_2$ and the combination of $R^{10a}$, $R^{10b}$, $R^{10c}$, $R^{10d}$ and $R^{10e}$ for a compound corresponds in each case to one row of Table A Table 32 Compounds of the formula Ia.2 in which $R^1$ is trifluoromethyl, $R^4$ is hydrogen, $R^3$ is C(=S)NHCH$_3$ and the combination of $R^{10a}$, $R^{10b}$, $R^{10c}$, $R^{10d}$ and $R^{10e}$ for a compound corresponds in each case to one row of Table A Table 33 Compounds of the formula Ia.2 in which $R^1$ is trifluoromethyl, $R^4$ is hydrogen, $R^3$ is C(=S)NHCH$_2$CH$_3$ and the combination of $R^{10a}$, $R^{10b}$, $R^{10c}$, $R^{10d}$ and $R^{10e}$ for a compound corresponds in each case to one row of Table A Table 34 Compounds of the formula Ia.2 in which $R^1$ is trifluoromethyl, $R^4$ is hydrogen, $R^3$ is C(=S)N(CH$_3$)$_2$ and the combination of $R^{10a}$, $R^{10b}$, $R^{10c}$, $R^{10d}$ and $R^{10e}$ for a compound corresponds in each case to one row of Table A Table 35 Compounds of the formula Ia.2 in which $R^1$ is trifluoromethyl, $R^4$ is hydrogen, $R^3$ is P(=O)(OCH$_3$)$_2$ and the combination of $R^{10a}$, $R^{10b}$, $R^{10c}$, $R^{10d}$ and $R^{10e}$ for a compound corresponds in each case to one row of Table A Table 36 Compounds of the formula Ia.2 in which $R^1$ is trifluoromethyl, $R^4$ is hydrogen, $R^3$ is P(=O)(OCH$_2$CH$_3$)$_2$ and the combination of $R^{10a}$, $R^{10b}$, $R^{10c}$, $R^{10d}$ and $R^{10e}$ for a compound corresponds in each case to one row of Table A Table 37 Compounds of the formula Ia.2 in which $R^1$ is trifluoromethyl, $R^4$ is hydrogen, $R^3$ is P(=O)(OCH$_2$CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 38 Compounds of the formula Ia.2 in which $R^1$ is trifluoromethyl, $R^4$ is hydrogen, $R^3$ is P(=O)[OCH(CH$_3$)$_2$]$_2$ and the combination of $R^{10a}$, $R^{10b}$, $R^{10c}$, $R^{10d}$ and $R^{10e}$ for a compound corresponds in each case to one row of Table A Table 39 Compounds of the formula Ia.2 in which $R^1$ is trifluoromethyl, $R^4$ is hydrogen, $R^3$ is P(=O)(CH$_3$)$_2$ and the combination of $R^{10a}$, $R^{10b}$, $R^{10c}$, $R^{10d}$ and $R^{10e}$ for a compound corresponds in each case to one row of Table A Table 40 Compounds of the formula Ia.2 in which $R^1$ is trifluoromethyl, $R^4$ is hydrogen, $R^3$ is P(=O)(CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 41 Compounds of the formula Ia.2 in which $R^1$ is trifluoromethyl, $R^4$ is hydrogen, $R^3$ is P(=O)(CH$_2$CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 42 Compounds of the formula Ia.2 in which $R^1$ is trifluoromethyl, $R^4$ is hydrogen, $R^3$ is P(=O)[CH(CH$_3$)$_2$]$_2$ and the combination of $R^{10a}$, $R^{10b}$, $R^{10c}$, $R^{10d}$ and $R^{10e}$ for a compound corresponds in each case to one row of Table A Table 43 Compounds of the formula Ia.2 in which $R^1$ is trifluoromethyl, $R^4$ is methyl, $R^3$ is NH$_2$ and the combination of $R^{10a}$, $R^{10b}$, $R^{10c}$, $R^{10d}$ and $R^{10e}$ for a compound corresponds in each case to one row of Table A Table 44 Compounds of the formula Ia.2 in which $R^1$ is trifluoromethyl, $R^4$ is methyl, $R^3$ is NHCH$_3$ and the combination of $R^{10a}$, $R^{10b}$, $R^{10c}$, $R^{10d}$ and $R^{10e}$ for a compound corresponds in each case to one row of Table A Table 45 Compounds of the formula Ia.2 in which $R^1$ is trifluoromethyl, $R^4$ is methyl, $R^3$ is NHNHC$_6$H$_5$ and the combination of $R^{10a}$, $R^{10b}$, $R^{10c}$, $R^{10d}$ and $R^{10e}$ for a compound corresponds in each case to one row of Table A Table 46 Compounds of the formula Ia.2 in which $R^1$ is trifluoromethyl, $R^4$ is methyl, $R^3$ is NHNHCH$_3$ and the combination of $R^{10a}$, $R^{10b}$, $R^{10c}$, $R^{10d}$ and $R^{10e}$ for a compound corresponds in each case to one row of Table A Table 47 Compounds of the formula Ia.2 in which $R^1$ is trifluoromethyl, $R^4$ is methyl, $R^3$ is NHNHCH$_2$CH$_3$ and the combination of $R^{10a}$, $R^{10b}$, $R^{10c}$, $R^{10d}$ and $R^{10e}$ for a compound corresponds in each case to one row of Table A Table 48 Compounds of the formula Ia.2 in which $R^1$ is trifluoromethyl, $R^4$ is methyl, $R^3$ is SO$_2$NH$_2$ and the combination of $R^{10a}$, $R^{10b}$, $R^{10c}$, $R^{10d}$ and $R^{10e}$ for a compound corresponds in each case to one row of Table A Table 49 Compounds of the formula Ia.2 in which $R^1$ is trifluoromethyl, $R^4$ is methyl, $R^3$ is SO$_2$NHCH$_3$ and the combination of $R^{10a}$, $R^{10b}$, $R^{10c}$, $R^{10d}$ and $R^{10e}$ for a compound corresponds in each case to one row of Table A Table 50 Compounds of the formula Ia.2 in which $R^1$ is trifluoromethyl, $R^4$ is methyl, $R^3$ is SO$_2$NHCH$_2$CH$_3$ and the combination of $R^{10a}$, $R^{10b}$, $R^{10c}$, $R^{10d}$ and $R^{10e}$ for a compound corresponds in each case to one row of Table A Table 51 Compounds of the formula Ia.2 in which $R^1$ is trifluoromethyl, $R^4$ is methyl, $R^3$ is SO$_2$N(CH$_3$)$_2$ and the combination of $R^{10a}$, $R^{10b}$, $R^{10c}$, $R^{10d}$ and $R^{10e}$ for a compound corresponds in each case to one row of Table A Table 52 Compounds of the formula Ia.2 in which $R^1$ is trifluoromethyl, $R^4$ is methyl, $R^3$ is C(=O)NH$_2$ and the combination of $R^{10a}$, $R^{10b}$, $R^{10c}$, $R^{10d}$ and $R^{10e}$ for a compound corresponds in each case to one row of Table A Table 53 Compounds of the formula Ia.2 in which $R^1$ is trifluoromethyl, $R^4$ is methyl, $R^3$ is C(=O)NHCH$_3$ and the combination of $R^{10a}$, $R^{10b}$, $R^{10c}$, $R^{10d}$ and $R^{10e}$ for a compound corresponds in each case to one row of Table A Table 54 Compounds of the formula Ia.2 in which $R^1$ is trifluoromethyl, $R^4$ is methyl, $R^3$ is C(=O)NHCH$_2$CH$_3$ and the combination of $R^{10a}$, $R^{10b}$, $R^{10c}$, $R^{10d}$ and $R^{10e}$ for a compound corresponds in each case to one row of Table A Table 55 Compounds of the formula Ia.2 in which $R^1$ is trifluoromethyl, $R^4$ is methyl, $R^3$ is C(=O)N(CH$_3$)$_2$ and the combination of $R^{10a}$, $R^{10b}$, $R^{10c}$, $R^{10d}$ and $R^{10e}$ for a compound corresponds in each case to one row of Table A Table 56 Compounds of the formula Ia.2 in which $R^1$ is trifluoromethyl, $R^4$ is methyl, $R^3$ is C(=S)NH$_2$ and the combination of $R^{10a}$, $R^{10b}$, $R^{10c}$, $R^{10d}$ and $R^{10e}$ for a compound corresponds in each case to one row of Table A Table 57 Compounds of the formula Ia.2 in which $R^1$ is trifluoromethyl, $R^4$ is methyl, $R^3$ is C(=S)NHCH$_3$ and the combination of $R^{10a}$, $R^{10b}$, $R^{10c}$, $R^{10d}$ and $R^{10e}$ for a compound corresponds in each case to one row of Table A Table 58 Compounds of the formula Ia.2 in which $R^1$ is trifluoromethyl, $R^4$ is methyl, $R^3$ is C(=S)NHCH$_2$CH$_3$ and the combination of $R^{10a}$, $R^{10b}$, $R^{10c}$, $R^{10d}$ and $R^{10e}$ for a compound corresponds in each case to one row of Table A Table 59 Compounds of the formula Ia.2 in which $R^1$ is trifluoromethyl, $R^4$ is methyl, $R^3$ is C(=S)N(CH$_3$)$_2$ and the combination of $R^{10a}$, $R^{10b}$, $R^{10c}$, $R^{10d}$ and $R^{10e}$ for a compound corresponds in each case to one row of Table A Table 60 Compounds of the formula Ia.2 in which $R^1$ is trifluoromethyl, $R^4$ is methyl, $R^3$ is P(=O)(OCH$_3$)$_2$ and the combination of $R^{10a}$, $R^{10b}$, $R^{10c}$, $R^{10d}$ and $R^{10e}$ for a compound corresponds in each case to one row of Table A Table 61 Compounds of the formula Ia.2 in which $R^1$ is trifluoromethyl, $R^4$ is methyl, $R^3$ is P(=O)(OCH$_2$CH$_3$)$_2$ and the combination of $R^{10a}$, $R^{10b}$, $R^{10c}$, $R^{10d}$ and $R^{10e}$ for a compound corresponds in each case to one row of Table A Table 62 Compounds of the formula Ia.2 in which $R^1$ is trifluoromethyl, $R^4$ is methyl, $R^3$ is P(=O)(OCH$_2$CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 63 Compounds of the formula Ia.2 in which $R^1$ is trifluoromethyl, $R^4$ is methyl, $R^3$ is P(=O)[OCH(CH$_3$)$_2$]$_2$ and the combination of $R^{10a}$, $R^{10b}$, $R^{10c}$, $R^{10d}$ and $R^{10e}$ for a compound corresponds in each case to one row of Table A Table 64 Compounds of the formula Ia.2 in which $R^1$ is trifluoromethyl, $R^4$ is methyl, $R^3$ is P(=O)(CH$_3$)$_2$ and the combination of $R^{10a}$, $R^{10b}$, $R^{10c}$, $R^{10d}$ and $R^{10e}$ for a compound corresponds in each case to one row of Table A Table 65 Compounds of the formula Ia.2 in which $R^1$ is trifluoromethyl, $R^4$ is methyl, $R^3$ is P(=O)(CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 66 Compounds of the formula Ia.2 in which $R^1$ is trifluoromethyl, $R^4$ is methyl, $R^3$ is P(=O)(CH$_2$CH$_2$CH$_3$)$_2$ and the combination of $R^{10a}$, $R^{10b}$, $R^{10c}$, $R^{10d}$ and $R^{10e}$ for a compound corresponds in each case to one row of Table A Table 67 Compounds of the formula Ia.2 in which $R^1$ is trifluoromethyl, $R^4$ is methyl, $R^3$ is P(=O)[CH(CH$_3$)$_2$]$_2$ and the combination of $R^{10a}$, $R^{10b}$, $R^{10c}$, $R^{10d}$ and $R^{10e}$ for a compound corresponds in each case to one row of Table A Table 68 Compounds of the formula Ia.2 in which $R^1$ is trifluoroethyl, $R^4$ is ethyl, $R^3$ is NH$_2$ and the combination of $R^{10a}$, $R^{10b}$, $R^{10c}$, $R^{10d}$ and $R^{10e}$ for a compound corresponds in each case to one row of Table A Table 69 Compounds of the formula Ia.2 in which $R^1$ is trifluoromethyl, $R^4$ is ethyl, $R^3$ is NHCH$_3$ and the combination of $R^{10a}$, $R^{10b}$, $R^{10c}$, $R^{10d}$ and $R^{10e}$ for a compound corresponds in each case to one row of Table A Table 70 Compounds of the formula Ia.2 in which $R^1$ is trifluoromethyl, $R^4$ is ethyl, $R^3$ is NHNHC$_6$H$_5$ and the combination of $R^{10a}$, $R^{10b}$, $R^{10c}$, $R^{10d}$ and $R^{10e}$ for a compound corresponds in each case to one row of Table A Table 71 Compounds of the formula Ia.2 in which $R^1$ is trifluoromethyl, $R^4$ is ethyl, $R^3$ is NHNHCH$_3$ and the combination of $R^{10a}$, $R^{10b}$, $R^{10c}$, $R^{10d}$ and $R^{10e}$ for a compound corresponds in each case to one row of Table A Table 72 Compounds of the formula Ia.2 in which $R^1$ is trifluoromethyl, $R^4$ is ethyl, $R^3$ is NHNHCH$_2$CH$_3$ and the combination of $R^{10a}$, $R^{10b}$, $R^{10c}$, $R^{10d}$ and $R^{10e}$ for a compound corresponds in each case to one row of Table A Table 73 Compounds of the formula Ia.2 in which $R^1$ is trifluoromethyl, $R^4$ is ethyl, $R^3$ is SO$_2$NH$_2$ and the combination of $R^{10a}$, $R^{10b}$, $R^{10c}$, $R^{10d}$ and $R^{10e}$ for a compound corresponds in each case to one row of Table A Table 74 Compounds of the formula Ia.2 in which $R^1$ is trifluoromethyl, $R^4$ is ethyl, $R^3$ is SO$_2$NHCH$_3$ and the combination of $R^{10a}$, $R^{10b}$, $R^{10c}$, $R^{10d}$ and $R^{10e}$ for a compound corresponds in each case to one row of Table A Table 75 Compounds of the formula Ia.2 in which $R^1$ is trifluoromethyl, $R^4$ is ethyl, $R^3$ is SO$_2$NHCH$_2$CH$_3$ and the combination of $R^{10a}$, $R^{10b}$, $R^{10c}$, $R^{10d}$ and $R^{10e}$ for a compound corresponds in each case to one row of Table A Table 76 Compounds of the formula Ia.2 in which $R^1$ is trifluoromethyl, $R^4$ is ethyl, $R^3$ is SO$_2$N(CH$_3$)$_2$ and the combination of $R^{10a}$, $R^{10b}$, $R^{10c}$, $R^{10d}$ and $R^{10e}$ for a compound corresponds in each case to one row of Table A Table 77 Compounds of the formula Ia.2 in which $R^1$ is trifluoromethyl, $R^4$ is ethyl, $R^3$ is C(=O)NH$_2$ and the combination of $R^{10a}$, $R^{10b}$, $R^{10c}$, $R^{10d}$ and $R^{10e}$ for a compound corresponds in each case to one row of Table A Table 78 Compounds of the formula Ia.2 in which $R^1$ is trifluoromethyl, $R^4$ is ethyl, $R^3$ is C(=O)NHCH$_3$ and the combination of $R^{10a}$, $R^{10b}$, $R^{10c}$, $R^{10d}$ and $R^{10e}$ for a compound corresponds in each case to one row of Table A Table 79 Compounds of the formula Ia.2 in which $R^1$ is trifluoromethyl, $R^4$ is ethyl, $R^3$ is C(=O)NHCH$_2$CH$_3$ and the combination of $R^{10a}$, $R^{10b}$, $R^{10c}$, $R^{10d}$ and $R^{10e}$ for a compound corresponds in each case to one row of Table A Table 80 Compounds of the formula Ia.2 in which $R^1$ is trifluoromethyl, $R^4$ is ethyl, $R^3$ is C(=O)N(CH$_3$)$_2$ and the combination of $R^{10a}$, $R^{10b}$, $R^{10c}$, $R^{10d}$ and $R^{10e}$ for a compound corresponds in each case to one row of Table A Table 81 Compounds of the formula Ia.2 in which $R^1$ is trifluoromethyl, $R^4$ is ethyl, $R^3$ is C(=S)NH$_2$ and the combination of $R^{10a}$, $R^{10b}$, $R^{10c}$, $R^{10d}$ and $R^{10e}$ for a compound corresponds in each case to one row of Table A Table 82 Compounds of the formula Ia.2 in which $R^1$ is trifluoromethyl, $R^4$ is ethyl, $R^3$ is C(=S)NHCH$_3$ and the combination of $R^{10a}$, $R^{10b}$, $R^{10c}$, $R^{10d}$ and $R^{10e}$ for a compound corresponds in each case to one row of Table A Table 83 Compounds of the formula Ia.2 in which $R^1$ is trifluoromethyl, $R^4$ is ethyl, $R^3$ is C(=S)NHCH$_2$CH$_3$ and the combination of $R^{10a}$, $R^{10b}$, $R^{10c}$, $R^{10d}$ and $R^{10e}$ for a compound corresponds in each case to one row of Table A Table 84 Compounds of the formula Ia.2 in which $R^1$ is trifluoromethyl, $R^4$ is ethyl, $R^3$ is C(=S)N(CH$_3$)$_2$ and the combination of $R^{10a}$, $R^{10b}$, $R^{10c}$, $R^{10d}$ and $R^{10e}$ for a compound corresponds in each case to one row of Table A Table 85 Compounds of the formula Ia.2 in which $R^1$ is trifluoromethyl, $R^4$ is ethyl, $R^3$ is P(=O)(OCH$_3$)$_2$ and the combination of $R^{10a}$, $R^{10b}$, $R^{10c}$, $R^{10d}$ and $R^{10e}$ for a compound corresponds in each case to one row of Table A Table 86 Compounds of the formula Ia.2 in which $R^1$ is trifluoromethyl, $R^4$ is ethyl, $R^3$ is P(=O)(OCH$_2$CH$_3$)$_2$ and the combination of $R^{10a}$, $R^{10b}$, $R^{10c}$, $R^{10d}$ and $R^{10e}$ for a compound corresponds in each case to one row of Table A Table 87 Compounds of the formula Ia.2 in which $R^1$ is trifluoromethyl, $R^4$ is ethyl, $R^3$ is $P(=O)(OCH_2CH_2CH_3)_2$ and the combination of $R^{10a}$, $R^{10b}$, $R^{10c}$, $R^{10d}$ and $R^{10e}$ for a compound corresponds in each case to one row of Table A Table 88 Compounds of the formula Ia.2 in which $R^1$ is trifluoromethyl, $R^4$ is ethyl, $R^3$ is $P(=O)[OCH(CH_3)_2]_2$ and the combination of $R^{10a}$, $R^{10b}$, $R^{10c}$, $R^{10d}$ and $R^{10e}$ for a compound corresponds in each case to one row of Table A Table 89 Compounds of the formula Ia.2 in which $R^1$ is trifluoromethyl, $R^4$ is ethyl, $R^3$ is $P(=O)(CH_3)_2$ and the combination of $R^{10a}$, $R^{10b}$, $R^{10c}$, $R^{10d}$ and $R^{10e}$ for a compound corresponds in each case to one row of Table A Table 90 Compounds of the formula Ia.2 in which $R^1$ is trifluoromethyl, $R^4$ is ethyl, $R^3$ is $P(=O)(CH_2CH_3)_2$ and the combination of $R^{10a}$, $R^{10b}$, $R^{10c}$, $R^{10d}$ and $R^{10e}$ for a compound corresponds in each case to one row of Table A Table 91 Compounds of the formula Ia.2 in which $R^1$ is trifluoromethyl, $R^4$ is ethyl, $R^3$ is $P(=O)(CH_2CH_2CH_3)_2$ and the combination of $R^{10a}$, $R^{10b}$, $R^{10c}$, $R^{10d}$ and $R^{10e}$ for a compound corresponds in each case to one row of Table A Table 92 Compounds of the formula Ia.2 in which $R^1$ is trifluoromethyl, $R^4$ is ethyl, $R^3$ is $P(=O)[CH(CH_3)_2]_2$ and the combination of $R^{10a}$, $R^{10b}$, $R^{10c}$, $R^{10d}$ and $R^{10e}$ for a compound corresponds in each case to one row of Table A Table 93 Compounds of the formula Ia.2 in which $R^1$ is trifluoromethyl, $R^4$ is acetyl, $R^3$ is $NH_2$ and the combination of $R^{10a}$, $R^{10b}$, $R^{10c}$, $R^{10d}$ and $R^{10e}$ for a compound corresponds in each case to one row of Table A Table 94 Compounds of the formula Ia.2 in which $R^1$ is trifluoromethyl, $R^4$ is acetyl, $R^3$ is $NHCH_3$ and the combination of $R^{10a}$, $R^{10b}$, $R^{10c}$, $R^{10d}$ and $R^{10e}$ for a compound corresponds in each case to one row of Table A Table 95 Compounds of the formula Ia.2 in which $R^1$ is trifluoromethyl, $R^4$ is acetyl, $R^3$ is $NHNHC_6H_5$ and the combination of $R^{10a}$, $R^{10b}$, $R^{10c}$, $R^{10d}$ and $R^{10e}$ for a compound corresponds in each case to one row of Table A Table 96 Compounds of the formula Ia.2 in which $R^1$ is trifluoromethyl, $R^4$ is acetyl, $R^3$ is $NHNHCH_3$ and the combination of $R^{10a}$, $R^{10b}$, $R^{10c}$, $R^{10d}$ and $R^{10e}$ for a compound corresponds in each case to one row of Table A Table 97 Compounds of the formula Ia.2 in which $R^1$ is trifluoromethyl, $R^4$ is acetyl, $R^3$ is $NHNHCH_2CH_3$ and the combination of $R^{10a}$, $R^{10b}$, $R^{10c}$, $R^{10d}$ and $R^{10e}$ for a compound corresponds in each case to one row of Table A Table 98 Compounds of the formula Ia.2 in which $R^1$ is trifluoromethyl, $R^4$ is acetyl, $R^3$ is $SO_2NH_2$ and the combination of $R^{10a}$, $R^{10b}$, $R^{10c}$, $R^{10d}$ and $R^{10e}$ for a compound corresponds in each case to one row of Table A Table 99 Compounds of the formula Ia.2 in which $R^1$ is trifluoromethyl, $R^4$ is acetyl, $R^3$ is $SO_2NHCH_3$ and the combination of $R^{10a}$, $R^{10b}$, $R^{10c}$, $R^{10d}$ and $R^{10e}$ for a compound corresponds in each case to one row of Table A Table 100 Compounds of the formula Ia.2 in which $R^1$ is trifluoromethyl, $R^4$ is acetyl, $R^3$ is $SO_2NHCH_2CH_3$ and the combination of $R^{10a}$, $R^{10b}$, $R^{10c}$, $R^{10d}$ and $R^{10e}$ for a compound corresponds in each case to one row of Table A Table 101 Compounds of the formula Ia.2 in which $R^1$ is trifluoromethyl, $R^4$ is acetyl, $R^3$ is $SO_2N(CH_3)_2$ and the combination of $R^{10a}$, $R^{10b}$, $R^{10c}$, $R^{10d}$ and $R^{10e}$ for a compound corresponds in each case to one row of Table A Table 102 Compounds of the formula Ia.2 in which $R^1$ is trifluoromethyl, $R^4$ is acetyl, $R^3$ is $C(=O)NH_2$ and the combination of $R^{10a}$, $R^{10b}$, $R^{10c}$, $R^{10d}$ and $R^{10e}$ for a compound corresponds in each case to one row of Table A Table 103 Compounds of the formula Ia.2 in which $R^1$ is trifluoromethyl, $R^4$ is acetyl, $R^3$ is $C(=O)NHCH_3$ and the combination of $R^{10a}$, $R^{10b}$, $R^{10c}$, $R^{10d}$ and $R^{10e}$ for a compound corresponds in each case to one row of Table A Table 104 Compounds of the formula Ia.2 in which $R^1$ is trifluoromethyl, $R^4$ is acetyl, $R^3$ is $C(=O)NHCH_2CH_3$ and the combination of $R^{10a}$, $R^{10b}$, $R^{10c}$, $R^{10d}$ and $R^{10e}$ for a compound corresponds in each case to one row of Table A Table 105 Compounds of the formula Ia.2 in which $R^1$ is trifluoromethyl, $R^4$ is acetyl, $R^3$ is $C(=O)N(CH_3)_2$ and the combination of $R^{10a}$, $R^{10b}$, $R^{10c}$, $R^{10d}$ and $R^{10e}$ for a compound corresponds in each case to one row of Table A Table 106 Compounds of the formula Ia.2 in which $R^1$ is trifluoromethyl, $R^4$ is acetyl, $R^3$ is $C(=S)NH_2$ and the combination of $R^{10a}$, $R^{10b}$, $R^{10c}$, $R^{10d}$ and $R^{10e}$ for a compound corresponds in each case to one row of Table A Table 107 Compounds of the formula Ia.2 in which $R^1$ is trifluoromethyl, $R^4$ is acetyl, $R^3$ is $C(=S)NHCH_3$ and the combination of $R^{10a}$, $R^{10b}$, $R^{10c}$, $R^{10d}$ and $R^{10e}$ for a compound corresponds in each case to one row of Table A Table 108 Compounds of the formula Ia.2 in which $R^1$ is trifluoromethyl, $R^4$ is acetyl, $R^3$ is $C(=S)NHCH_2CH_3$ and the combination of $R^{10a}$, $R^{10b}$, $R^{10c}$, $R^{10d}$ and $R^{10e}$ for a compound corresponds in each case to one row of Table A Table 109 Compounds of the formula Ia.2 in which $R^1$ is trifluoromethyl, $R^4$ is acetyl, $R^3$ is $C(=S)N(CH_3)_2$ and the combination of $R^{10a}$, $R^{10b}$, $R^{10c}$, $R^{10d}$ and $R^{10e}$ for a compound corresponds in each case to one row of Table A Table 110 Compounds of the formula Ia.2 in which $R^1$ is trifluoromethyl, $R^4$ is acetyl, $R^3$ is $P(=O)(OCH_3)_2$ and the combination of $R^{10a}$, $R^{10b}$, $R^{10c}$, $R^{10d}$ and $R^{10e}$ for a compound corresponds in each case to one row of Table A Table 111 Compounds of the formula Ia.2 in which $R^1$ is trifluoromethyl, $R^4$ is acetyl, $R^3$ is $P(=O)(OCH_2CH_3)_2$ and the combination of $R^{10a}$, $R^{10b}$, $R^{10c}$, $R^{10d}$ and $R^{10e}$ for a compound corresponds in each case to one row of Table A Table 112 Compounds of the formula Ia.2 in which $R^1$ is trifluoromethyl, $R^4$ is acetyl, $R^3$ is $P(=O)(OCH_2CH_2CH_3)_2$ and the combination of $R^{10a}$, $R^{10b}$, $R^{10c}$, $R^{10d}$ and $R^{10e}$ for a compound corresponds in each case to one row of Table A Table 113 Compounds of the formula Ia.2 in which $R^1$ is trifluoromethyl, $R^4$ is acetyl, $R^3$ is $P(=O)[OCH(CH_3)_2]_2$ and the combination of $R^{10a}$, $R^{10b}$, $R^{10c}$, $R^{10d}$ and $R^{10e}$ for a compound corresponds in each case to one row of Table A Table 114 Compounds of the formula Ia.2 in which $R^1$ is trifluoromethyl, $R^4$ is acetyl, $R^3$ is $P(=O)(CH_3)_2$ and the combination of $R^{10a}$, $R^{10b}$, $R^{10c}$, $R^{10d}$ and $R^{10e}$ for a compound corresponds in each case to one row of Table A Table 115 Compounds of the formula Ia.2 in which $R^1$ is trifluoromethyl, $R^4$ is acetyl, $R^3$ is $P(=O)(CH_2CH_3)_2$ and the combination of $R^{10a}$, $R^{10b}$, $R^{10c}$, $R^{10d}$ and $R^{10e}$ for a compound corresponds in each case to one row of Table A Table 116 Compounds of the formula Ia.2 in which $R^1$ is trifluoromethyl, $R^4$ is acetyl, $R^3$ is $P(=O)(CH_2CH_2CH_3)_2$ and the combination of $R^{10a}$, $R^{10b}$, $R^{10c}$, $R^{10d}$ and $R^{10e}$ for a compound corresponds in each case to one row of Table A Table 117 Compounds of the formula Ia.2 in which $R^1$ is trifluoromethyl, $R^4$ is acetyl, $R^3$ is $P(=O)[CH(CH_3)_2]_2$ and the combination of $R^{10a}$, $R^{10b}$, $R^{10c}$, $R^{10d}$ and $R^{10e}$ for a compound corresponds in each case to one row of Table A

TABLE A

| No. | $R^{10a}$ | $R^{10b}$ | $R^{10c}$ | $R^{10d}$ | $R^{10e}$ |
|---|---|---|---|---|---|
| A-1 | H | H | H | H | H |
| A-2 | CH$_3$ | H | H | H | H |
| A-3 | Cl | H | H | H | H |
| A-4 | Br | H | H | H | H |
| A-5 | I | H | H | H | H |
| A-6 | CF$_3$ | H | H | H | H |
| A-7 | CH$_2$CF$_3$ | H | H | H | H |
| A-8 | CH$_2$CH$_3$ | H | H | H | H |
| A-9 | OCH$_3$ | H | H | H | H |
| A-10 | OCF$_3$ | H | H | H | H |
| A-11 | H | CH$_3$ | H | H | H |
| A-12 | H | Cl | H | H | H |
| A-13 | H | Br | H | H | H |
| A-14 | H | I | H | H | H |
| A-15 | H | CF$_3$ | H | H | H |
| A-16 | H | CH$_2$CF$_3$ | H | H | H |
| A-17 | H | CH$_2$CH$_3$ | H | H | H |
| A-18 | H | OCH$_3$ | H | H | H |
| A-19 | H | OCF$_3$ | H | H | H |
| A-20 | H | H | CH$_3$ | H | H |
| A-21 | H | H | Cl | H | H |
| A-22 | H | H | Br | H | H |
| A-23 | H | H | I | H | H |
| A-24 | H | H | CF$_3$ | H | H |
| A-25 | H | H | CH$_2$CF$_3$ | H | H |
| A-26 | H | H | CH$_2$CH$_3$ | H | H |
| A-27 | H | H | OCH$_3$ | H | H |
| A-28 | H | H | OCF$_3$ | H | H |
| A-29 | CH$_3$ | CH$_3$ | H | H | H |
| A-30 | CH$_3$ | Cl | H | H | H |
| A-31 | CH$_3$ | Br | H | H | H |
| A-32 | CH$_3$ | I | H | H | H |
| A-33 | CH$_3$ | CF$_3$ | H | H | H |
| A-34 | CH$_3$ | CH$_2$CF$_3$ | H | H | H |
| A-35 | CH$_3$ | CH$_2$CH$_3$ | H | H | H |
| A-36 | CH$_3$ | OCH$_3$ | H | H | H |
| A-37 | CH$_3$ | OCF$_3$ | H | H | H |
| A-38 | CH$_3$ | H | CH$_3$ | H | H |
| A-39 | CH$_3$ | H | Cl | H | H |
| A-40 | CH$_3$ | H | Br | H | H |
| A-41 | CH$_3$ | H | I | H | H |
| A-42 | CH$_3$ | H | CF$_3$ | H | H |
| A-43 | CH$_3$ | H | CH$_2$CF$_3$ | H | H |
| A-44 | CH$_3$ | H | CH$_2$CH$_3$ | H | H |
| A-45 | CH$_3$ | H | OCH$_3$ | H | H |
| A-46 | CH$_3$ | H | OCF$_3$ | H | H |
| A-47 | CH$_3$ | H | H | CH$_3$ | H |
| A-48 | CH$_3$ | H | H | Cl | H |
| A-49 | CH$_3$ | H | H | Br | H |
| A-50 | CH$_3$ | H | H | I | H |
| A-51 | CH$_3$ | H | H | CF$_3$ | H |
| A-52 | CH$_3$ | H | H | CH$_2$CF$_3$ | H |
| A-53 | CH$_3$ | H | H | CH$_2$CH$_3$ | H |
| A-54 | CH$_3$ | H | H | OCH$_3$ | H |
| A-55 | CH$_3$ | H | H | OCF$_3$ | H |
| A-56 | CH$_3$ | H | H | H | CH$_3$ |
| A-57 | CH$_3$ | H | H | H | Cl |
| A-58 | CH$_3$ | H | H | H | Br |
| A-59 | CH$_3$ | H | H | H | I |
| A-60 | CH$_3$ | H | H | H | CF$_3$ |
| A-61 | CH$_3$ | H | H | H | CH$_2$CF$_3$ |
| A-62 | CH$_3$ | H | H | H | CH$_2$CH$_3$ |
| A-63 | CH$_3$ | H | H | H | OCH$_3$ |
| A-64 | CH$_3$ | H | H | H | OCF$_3$ |
| A-65 | Cl | CH$_3$ | H | H | H |
| A-66 | Cl | Cl | H | H | H |
| A-67 | Cl | Br | H | H | H |
| A-68 | Cl | I | H | H | H |
| A-69 | Cl | CF$_3$ | H | H | H |
| A-70 | Cl | CH$_2$CF$_3$ | H | H | H |
| A-71 | Cl | CH$_2$CH$_3$ | H | H | H |
| A-72 | Cl | OCH$_3$ | H | H | H |
| A-73 | Cl | OCF$_3$ | H | H | H |
| A-74 | Cl | H | CH$_3$ | H | H |
| A-75 | Cl | H | Cl | H | H |
| A-76 | Cl | H | Br | H | H |
| A-77 | Cl | H | I | H | H |
| A-78 | Cl | H | CF$_3$ | H | H |
| A-79 | Cl | H | CH$_2$CF$_3$ | H | H |
| A-80 | Cl | H | CH$_2$CH$_3$ | H | H |
| A-81 | Cl | H | OCH$_3$ | H | H |
| A-82 | Cl | H | OCF$_3$ | H | H |
| A-83 | Cl | H | H | CH$_3$ | H |
| A-84 | Cl | H | H | Cl | H |
| A-85 | Cl | H | H | Br | H |
| A-86 | Cl | H | H | I | H |
| A-87 | Cl | H | H | CF$_3$ | H |
| A-88 | Cl | H | H | CH$_2$CF$_3$ | H |
| A-89 | Cl | H | H | CH$_2$CH$_3$ | H |
| A-90 | Cl | H | H | OCH$_3$ | H |
| A-91 | Cl | H | H | OCF$_3$ | H |
| A-92 | Cl | H | H | H | CH$_3$ |
| A-93 | Cl | H | H | H | Cl |
| A-94 | Cl | H | H | H | Br |
| A-95 | Cl | H | H | H | I |
| A-96 | Cl | H | H | H | CF$_3$ |
| A-97 | Cl | H | H | H | CH$_2$CF$_3$ |
| A-98 | Cl | H | H | H | CH$_2$CH$_3$ |
| A-99 | Cl | H | H | H | OCH$_3$ |
| A-100 | Cl | H | H | H | OCF$_3$ |
| A-101 | Br | CH$_3$ | H | H | H |
| A-102 | Br | Cl | H | H | H |
| A-103 | Br | Br | H | H | H |
| A-104 | Br | I | H | H | H |
| A-105 | Br | CF$_3$ | H | H | H |
| A-106 | Br | CH$_2$CF$_3$ | H | H | H |
| A-107 | Br | CH$_2$CH$_3$ | H | H | H |
| A-108 | Br | OCH$_3$ | H | H | H |
| A-109 | Br | OCF$_3$ | H | H | H |
| A-110 | Br | H | CH$_3$ | H | H |
| A-111 | Br | H | Cl | H | H |
| A-112 | Br | H | Br | H | H |
| A-113 | Br | H | I | H | H |
| A-114 | Br | H | CF$_3$ | H | H |
| A-115 | Br | H | CH$_2$CF$_3$ | H | H |
| A-116 | Br | H | CH$_2$CH$_3$ | H | H |
| A-117 | Br | H | OCH$_3$ | H | H |
| A-118 | Br | H | OCF$_3$ | H | H |
| A-119 | Br | H | H | CH$_3$ | H |
| A-120 | Br | H | H | Cl | H |
| A-121 | Br | H | H | Br | H |
| A-122 | Br | H | H | I | H |
| A-123 | Br | H | H | CF$_3$ | H |
| A-124 | Br | H | H | CH$_2$CF$_3$ | H |
| A-125 | Br | H | H | CH$_2$CH$_3$ | H |
| A-126 | Br | H | H | OCH$_3$ | H |
| A-127 | Br | H | H | OCF$_3$ | H |
| A-128 | Br | H | H | H | CH$_3$ |
| A-129 | Br | H | H | H | Cl |
| A-130 | Br | H | H | H | Br |
| A-131 | Br | H | H | H | I |
| A-132 | Br | H | H | H | CF$_3$ |
| A-133 | Br | H | H | H | CH$_2$CF$_3$ |
| A-134 | Br | H | H | H | CH$_2$CH$_3$ |
| A-135 | Br | H | H | H | OCH$_3$ |
| A-136 | Br | H | H | H | OCF$_3$ |
| A-137 | I | CH$_3$ | H | H | H |
| A-138 | I | Cl | H | H | H |
| A-139 | I | Br | H | H | H |
| A-140 | I | I | H | H | H |
| A-141 | I | CF$_3$ | H | H | H |
| A-142 | I | CH$_2$CF$_3$ | H | H | H |
| A-143 | I | CH$_2$CH$_3$ | H | H | H |
| A-144 | I | OCH$_3$ | H | H | H |
| A-145 | I | OCF$_3$ | H | H | H |
| A-146 | I | H | CH$_3$ | H | H |
| A-147 | I | H | Cl | H | H |
| A-148 | I | H | Br | H | H |
| A-149 | I | H | I | H | H |
| A-150 | I | H | CF$_3$ | H | H |
| A-151 | I | H | CH$_2$CF$_3$ | H | H |
| A-152 | I | H | CH$_2$CH$_3$ | H | H |
| A-153 | I | H | OCH$_3$ | H | H |
| A-154 | I | H | OCF$_3$ | H | H |
| A-155 | I | H | H | CH$_3$ | H |
| A-156 | I | H | H | Cl | H |

TABLE A-continued

| No. | $R^{10a}$ | $R^{10b}$ | $R^{10c}$ | $R^{10d}$ | $R^{10e}$ |
|---|---|---|---|---|---|
| A-157 | I | H | H | Br | H |
| A-158 | I | H | H | I | H |
| A-159 | I | H | H | CF$_3$ | H |
| A-160 | I | H | H | CH$_2$CF$_3$ | H |
| A-161 | I | H | H | CH$_2$CH$_3$ | H |
| A-162 | I | H | H | OCH$_3$ | H |
| A-163 | I | H | H | OCF$_3$ | H |
| A-164 | I | H | H | H | CH$_3$ |
| A-165 | I | H | H | H | Cl |
| A-166 | I | H | H | H | Br |
| A-167 | I | H | H | H | I |
| A-168 | I | H | H | H | CF$_3$ |
| A-169 | I | H | H | H | CH$_2$CF$_3$ |
| A-170 | I | H | H | H | CH$_2$CH$_3$ |
| A-171 | I | H | H | H | OCH$_3$ |
| A-172 | I | H | H | H | OCF$_3$ |
| A-173 | CF$_3$ | CH$_3$ | H | H | H |
| A-174 | CF$_3$ | Cl | H | H | H |
| A-175 | CF$_3$ | Br | H | H | H |
| A-176 | CF$_3$ | I | H | H | H |
| A-177 | CF$_3$ | CF$_3$ | H | H | H |
| A-178 | CF$_3$ | CH$_2$CF$_3$ | H | H | H |
| A-179 | CF$_3$ | CH$_2$CH$_3$ | H | H | H |
| A-180 | CF$_3$ | OCH$_3$ | H | H | H |
| A-181 | CF$_3$ | OCF$_3$ | H | H | H |
| A-182 | CF$_3$ | H | CH$_3$ | H | H |
| A-183 | CF$_3$ | H | Cl | H | H |
| A-184 | CF$_3$ | H | Br | H | H |
| A-185 | CF$_3$ | H | I | H | H |
| A-186 | CF$_3$ | H | CF$_3$ | H | H |
| A-187 | CF$_3$ | H | CH$_2$CF$_3$ | H | H |
| A-188 | CF$_3$ | H | CH$_2$CH$_3$ | H | H |
| A-189 | CF$_3$ | H | OCH$_3$ | H | H |
| A-190 | CF$_3$ | H | OCF$_3$ | H | H |
| A-191 | CF$_3$ | H | H | CH$_3$ | H |
| A-192 | CF$_3$ | H | H | Cl | H |
| A-193 | CF$_3$ | H | H | Br | H |
| A-194 | CF$_3$ | H | H | I | H |
| A-195 | CF$_3$ | H | H | CF$_3$ | H |
| A-196 | CF$_3$ | H | H | CH$_2$CF$_3$ | H |
| A-197 | CF$_3$ | H | H | CH$_2$CH$_3$ | H |
| A-198 | CF$_3$ | H | H | OCH$_3$ | H |
| A-199 | CF$_3$ | H | H | OCF$_3$ | H |
| A-200 | CF$_3$ | H | H | H | CH$_3$ |
| A-201 | CF$_3$ | H | H | H | Cl |
| A-202 | CF$_3$ | H | H | H | Br |
| A-203 | CF$_3$ | H | H | H | I |
| A-204 | CF$_3$ | H | H | H | CF$_3$ |
| A-205 | CF$_3$ | H | H | H | CH$_2$CF$_3$ |
| A-206 | CF$_3$ | H | H | H | CH$_2$CH$_3$ |
| A-207 | CF$_3$ | H | H | H | OCH$_3$ |
| A-208 | CF$_3$ | H | H | H | OCF$_3$ |
| A-209 | CH$_2$CF$_3$ | CH$_3$ | H | H | H |
| A-210 | CH$_2$CF$_3$ | Cl | H | H | H |
| A-211 | CH$_2$CF$_3$ | Br | H | H | H |
| A-212 | CH$_2$CF$_3$ | I | H | H | H |
| A-213 | CH$_2$CF$_3$ | CF$_3$ | H | H | H |
| A-214 | CH$_2$CF$_3$ | CH$_2$CF$_3$ | H | H | H |
| A-215 | CH$_2$CF$_3$ | CH$_2$CH$_3$ | H | H | H |
| A-216 | CH$_2$CF$_3$ | OCH$_3$ | H | H | H |
| A-217 | CH$_2$CF$_3$ | OCF$_3$ | H | H | H |
| A-218 | CH$_2$CF$_3$ | H | CH$_3$ | H | H |
| A-219 | CH$_2$CF$_3$ | H | Cl | H | H |
| A-220 | CH$_2$CF$_3$ | H | Br | H | H |
| A-221 | CH$_2$CF$_3$ | H | I | H | H |
| A-222 | CH$_2$CF$_3$ | H | CF$_3$ | H | H |
| A-223 | CH$_2$CF$_3$ | H | CH$_2$CF$_3$ | H | H |
| A-224 | CH$_2$CF$_3$ | H | CH$_2$CH$_3$ | H | H |
| A-225 | CH$_2$CF$_3$ | H | OCH$_3$ | H | H |
| A-226 | CH$_2$CF$_3$ | H | OCF$_3$ | H | H |
| A-227 | CH$_2$CF$_3$ | H | H | CH$_3$ | H |
| A-228 | CH$_2$CF$_3$ | H | H | Cl | H |
| A-229 | CH$_2$CF$_3$ | H | H | Br | H |
| A-230 | CH$_2$CF$_3$ | H | H | I | H |
| A-231 | CH$_2$CF$_3$ | H | H | CF$_3$ | H |
| A-232 | CH$_2$CF$_3$ | H | H | CH$_2$CF$_3$ | H |
| A-233 | CH$_2$CF$_3$ | H | H | CH$_2$CH$_3$ | H |
| A-234 | CH$_2$CF$_3$ | H | H | OCH$_3$ | H |
| A-235 | CH$_2$CF$_3$ | H | H | OCF$_3$ | H |
| A-236 | CH$_2$CF$_3$ | H | H | H | CH$_3$ |
| A-237 | CH$_2$CF$_3$ | H | H | H | Cl |
| A-238 | CH$_2$CF$_3$ | H | H | H | Br |
| A-239 | CH$_2$CF$_3$ | H | H | H | I |
| A-240 | CH$_2$CF$_3$ | H | H | H | CF$_3$ |
| A-241 | CH$_2$CF$_3$ | H | H | H | CH$_2$CF$_3$ |
| A-242 | CH$_2$CF$_3$ | H | H | H | CH$_2$CH$_3$ |
| A-243 | CH$_2$CF$_3$ | H | H | H | OCH$_3$ |
| A-244 | CH$_2$CF$_3$ | H | H | H | OCF$_3$ |
| A-245 | CH$_2$CH$_3$ | CH$_3$ | H | H | H |
| A-246 | CH$_2$CH$_3$ | Cl | H | H | H |
| A-247 | CH$_2$CH$_3$ | Br | H | H | H |
| A-248 | CH$_2$CH$_3$ | I | H | H | H |
| A-249 | CH$_2$CH$_3$ | CF$_3$ | H | H | H |
| A-250 | CH$_2$CH$_3$ | CH$_2$CF$_3$ | H | H | H |
| A-251 | CH$_2$CH$_3$ | CH$_2$CH$_3$ | H | H | H |
| A-252 | CH$_2$CH$_3$ | OCH$_3$ | H | H | H |
| A-253 | CH$_2$CH$_3$ | OCF$_3$ | H | H | H |
| A-254 | CH$_2$CH$_3$ | H | CH$_3$ | H | H |
| A-255 | CH$_2$CH$_3$ | H | Cl | H | H |
| A-256 | CH$_2$CH$_3$ | H | Br | H | H |
| A-257 | CH$_2$CH$_3$ | H | I | H | H |
| A-258 | CH$_2$CH$_3$ | H | CF$_3$ | H | H |
| A-259 | CH$_2$CH$_3$ | H | CH$_2$CF$_3$ | H | H |
| A-260 | CH$_2$CH$_3$ | H | CH$_2$CH$_3$ | H | H |
| A-261 | CH$_2$CH$_3$ | H | OCH$_3$ | H | H |
| A-262 | CH$_2$CH$_3$ | H | OCF$_3$ | H | H |
| A-263 | CH$_2$CH$_3$ | H | H | CH$_3$ | H |
| A-264 | CH$_2$CH$_3$ | H | H | Cl | H |
| A-265 | CH$_2$CH$_3$ | H | H | Br | H |
| A-266 | CH$_2$CH$_3$ | H | H | I | H |
| A-267 | CH$_2$CH$_3$ | H | H | CF$_3$ | H |
| A-268 | CH$_2$CH$_3$ | H | H | CH$_2$CF$_3$ | H |
| A-269 | CH$_2$CH$_3$ | H | H | CH$_2$CH$_3$ | H |
| A-270 | CH$_2$CH$_3$ | H | H | OCH$_3$ | H |
| A-271 | CH$_2$CH$_3$ | H | H | OCF$_3$ | H |
| A-272 | CH$_2$CH$_3$ | H | H | H | CH$_3$ |
| A-273 | CH$_2$CH$_3$ | H | H | H | Cl |
| A-274 | CH$_2$CH$_3$ | H | H | H | Br |
| A-275 | CH$_2$CH$_3$ | H | H | H | I |
| A-276 | CH$_2$CH$_3$ | H | H | H | CF$_3$ |
| A-277 | CH$_2$CH$_3$ | H | H | H | CH$_2$CF$_3$ |
| A-278 | CH$_2$CH$_3$ | H | H | H | CH$_2$CH$_3$ |
| A-279 | CH$_2$CH$_3$ | H | H | H | OCH$_3$ |
| A-280 | CH$_2$CH$_3$ | H | H | H | OCF$_3$ |
| A-281 | OCH$_3$ | CH$_3$ | H | H | H |
| A-282 | OCH$_3$ | Cl | H | H | H |
| A-283 | OCH$_3$ | Br | H | H | H |
| A-284 | OCH$_3$ | I | H | H | H |
| A-285 | OCH$_3$ | CF$_3$ | H | H | H |
| A-286 | OCH$_3$ | CH$_2$CF$_3$ | H | H | H |
| A-287 | OCH$_3$ | CH$_2$CH$_3$ | H | H | H |
| A-288 | OCH$_3$ | OCH$_3$ | H | H | H |
| A-289 | OCH$_3$ | OCF$_3$ | H | H | H |
| A-290 | OCH$_3$ | H | CH$_3$ | H | H |
| A-291 | OCH$_3$ | H | Cl | H | H |
| A-292 | OCH$_3$ | H | Br | H | H |
| A-293 | OCH$_3$ | H | I | H | H |
| A-294 | OCH$_3$ | H | CF$_3$ | H | H |
| A-295 | OCH$_3$ | H | CH$_2$CF$_3$ | H | H |
| A-296 | OCH$_3$ | H | CH$_2$CH$_3$ | H | H |
| A-297 | OCH$_3$ | H | OCH$_3$ | H | H |
| A-298 | OCH$_3$ | H | OCF$_3$ | H | H |
| A-299 | OCH$_3$ | H | H | CH$_3$ | H |
| A-300 | OCH$_3$ | H | H | Cl | H |
| A-301 | OCH$_3$ | H | H | Br | H |
| A-302 | OCH$_3$ | H | H | I | H |
| A-303 | OCH$_3$ | H | H | CF$_3$ | H |
| A-304 | OCH$_3$ | H | H | CH$_2$CF$_3$ | H |
| A-305 | OCH$_3$ | H | H | CH$_2$CH$_3$ | H |
| A-306 | OCH$_3$ | H | H | OCH$_3$ | H |
| A-307 | OCH$_3$ | H | H | OCF$_3$ | H |
| A-308 | OCH$_3$ | H | H | H | CH$_3$ |
| A-309 | OCH$_3$ | H | H | H | Cl |
| A-310 | OCH$_3$ | H | H | H | Br |
| A-311 | OCH$_3$ | H | H | H | I |
| A-312 | OCH$_3$ | H | H | H | CF$_3$ |

TABLE A-continued

| No. | $R^{10a}$ | $R^{10b}$ | $R^{10c}$ | $R^{10d}$ | $R^{10e}$ |
|---|---|---|---|---|---|
| A-313 | OCH$_3$ | H | H | H | CH$_2$CF$_3$ |
| A-314 | OCH$_3$ | H | H | H | CH$_2$CH$_3$ |
| A-315 | OCH$_3$ | H | H | H | OCH$_3$ |
| A-316 | OCH$_3$ | H | H | H | OCF$_3$ |
| A-317 | OCF$_3$ | CH$_3$ | H | H | H |
| A-318 | OCF$_3$ | Cl | H | H | H |
| A-319 | OCF$_3$ | Br | H | H | H |
| A-320 | OCF$_3$ | I | H | H | H |
| A-321 | OCF$_3$ | CF$_3$ | H | H | H |
| A-322 | OCF$_3$ | CH$_2$CF$_3$ | H | H | H |
| A-323 | OCF$_3$ | CH$_2$CH$_3$ | H | H | H |
| A-324 | OCF$_3$ | OCH$_3$ | H | H | H |
| A-325 | OCF$_3$ | OCF$_3$ | H | H | H |
| A-326 | OCF$_3$ | H | CH$_3$ | H | H |
| A-327 | OCF$_3$ | H | Cl | H | H |
| A-328 | OCF$_3$ | H | Br | H | H |
| A-329 | OCF$_3$ | H | I | H | H |
| A-330 | OCF$_3$ | H | CF$_3$ | H | H |
| A-331 | OCF$_3$ | H | CH$_2$CF$_3$ | H | H |
| A-332 | OCF$_3$ | H | CH$_2$CH$_3$ | H | H |
| A-333 | OCF$_3$ | H | OCH$_3$ | H | H |
| A-334 | OCF$_3$ | H | OCF$_3$ | H | H |
| A-335 | OCF$_3$ | H | H | CH$_3$ | H |
| A-336 | OCF$_3$ | H | H | Cl | H |
| A-337 | OCF$_3$ | H | H | Br | H |
| A-338 | OCF$_3$ | H | H | I | H |
| A-339 | OCF$_3$ | H | H | CF$_3$ | H |
| A-340 | OCF$_3$ | H | H | CH$_2$CF$_3$ | H |
| A-341 | OCF$_3$ | H | H | CH$_2$CH$_3$ | H |
| A-342 | OCF$_3$ | H | H | OCH$_3$ | H |
| A-343 | OCF$_3$ | H | H | OCF$_3$ | H |
| A-344 | OCF$_3$ | H | H | H | CH$_3$ |
| A-345 | OCF$_3$ | H | H | H | Cl |
| A-346 | OCF$_3$ | H | H | H | Br |
| A-347 | OCF$_3$ | H | H | H | I |
| A-348 | OCF$_3$ | H | H | H | CF$_3$ |
| A-349 | OCF$_3$ | H | H | H | CH$_2$CF$_3$ |
| A-350 | OCF$_3$ | H | H | H | CH$_2$CH$_3$ |
| A-351 | OCF$_3$ | H | H | H | OCH$_3$ |
| A-352 | OCF$_3$ | H | H | H | OCF$_3$ |
| A-353 | H | CH$_3$ | CH$_3$ | H | H |
| A-354 | H | CH$_3$ | Cl | H | H |
| A-355 | H | CH$_3$ | Br | H | H |
| A-356 | H | CH$_3$ | I | H | H |
| A-357 | H | CH$_3$ | CF$_3$ | H | H |
| A-358 | H | CH$_3$ | CH$_2$CF$_3$ | H | H |
| A-359 | H | CH$_3$ | CH$_2$CH$_3$ | H | H |
| A-360 | H | CH$_3$ | OCH$_3$ | H | H |
| A-361 | H | CH$_3$ | OCF$_3$ | H | H |
| A-362 | H | CH$_3$ | H | CH$_3$ | H |
| A-363 | H | CH$_3$ | H | Cl | H |
| A-364 | H | CH$_3$ | H | Br | H |
| A-365 | H | CH$_3$ | H | I | H |
| A-366 | H | CH$_3$ | H | CF$_3$ | H |
| A-367 | H | CH$_3$ | H | CH$_2$CF$_3$ | H |
| A-368 | H | CH$_3$ | H | CH$_2$CH$_3$ | H |
| A-369 | H | CH$_3$ | H | OCH$_3$ | H |
| A-370 | H | CH$_3$ | H | OCF$_3$ | H |
| A-371 | H | Cl | CH$_3$ | H | H |
| A-372 | H | Cl | Cl | H | H |
| A-373 | H | Cl | Br | H | H |
| A-374 | H | Cl | I | H | H |
| A-375 | H | Cl | CF$_3$ | H | H |
| A-376 | H | Cl | CH$_2$CF$_3$ | H | H |
| A-377 | H | Cl | CH$_2$CH$_3$ | H | H |
| A-378 | H | Cl | OCH$_3$ | H | H |
| A-379 | H | Cl | OCF$_3$ | H | H |
| A-380 | H | Cl | H | CH$_3$ | H |
| A-381 | H | Cl | H | Cl | H |
| A-382 | H | Cl | H | Br | H |
| A-383 | H | Cl | H | I | H |
| A-384 | H | Cl | H | CF$_3$ | H |
| A-385 | H | Cl | H | CH$_2$CF$_3$ | H |
| A-386 | H | Cl | H | CH$_2$CH$_3$ | H |
| A-387 | H | Cl | H | OCH$_3$ | H |
| A-388 | H | Cl | H | OCF$_3$ | H |
| A-389 | H | Br | CH$_3$ | H | H |
| A-390 | H | Br | Cl | H | H |
| A-391 | H | Br | Br | H | H |
| A-392 | H | Br | I | H | H |
| A-393 | H | Br | CF$_3$ | H | H |
| A-394 | H | Br | CH$_2$CF$_3$ | H | H |
| A-395 | H | Br | CH$_2$CH$_3$ | H | H |
| A-396 | H | Br | OCH$_3$ | H | H |
| A-397 | H | Br | OCF$_3$ | H | H |
| A-398 | H | Br | H | CH$_3$ | H |
| A-399 | H | Br | H | Cl | H |
| A-400 | H | Br | H | Br | H |
| A-401 | H | Br | H | I | H |
| A-402 | H | Br | H | CF$_3$ | H |
| A-403 | H | Br | H | CH$_2$CF$_3$ | H |
| A-404 | H | Br | H | CH$_2$CH$_3$ | H |
| A-405 | H | Br | H | OCH$_3$ | H |
| A-406 | H | Br | H | OCF$_3$ | H |
| A-407 | H | I | CH$_3$ | H | H |
| A-408 | H | I | Cl | H | H |
| A-409 | H | I | Br | H | H |
| A-410 | H | I | I | H | H |
| A-411 | H | I | CF$_3$ | H | H |
| A-412 | H | I | CH$_2$CF$_3$ | H | H |
| A-413 | H | I | CH$_2$CH$_3$ | H | H |
| A-414 | H | I | OCH$_3$ | H | H |
| A-415 | H | I | OCF$_3$ | H | H |
| A-416 | H | I | H | CH$_3$ | H |
| A-417 | H | I | H | Cl | H |
| A-418 | H | I | H | Br | H |
| A-419 | H | I | H | I | H |
| A-420 | H | I | H | CF$_3$ | H |
| A-421 | H | I | H | CH$_2$CF$_3$ | H |
| A-422 | H | I | H | CH$_2$CH$_3$ | H |
| A-423 | H | I | H | OCH$_3$ | H |
| A-424 | H | I | H | OCF$_3$ | H |
| A-425 | H | CF$_3$ | CH$_3$ | H | H |
| A-426 | H | CF$_3$ | Cl | H | H |
| A-427 | H | CF$_3$ | Br | H | H |
| A-428 | H | CF$_3$ | I | H | H |
| A-429 | H | CF$_3$ | CF$_3$ | H | H |
| A-430 | H | CF$_3$ | CH$_2$CF$_3$ | H | H |
| A-431 | H | CF$_3$ | CH$_2$CH$_3$ | H | H |
| A-432 | H | CF$_3$ | OCH$_3$ | H | H |
| A-433 | H | CF$_3$ | OCF$_3$ | H | H |
| A-434 | H | CF$_3$ | H | CH$_3$ | H |
| A-435 | H | CF$_3$ | H | Cl | H |
| A-436 | H | CF$_3$ | H | Br | H |
| A-437 | H | CF$_3$ | H | I | H |
| A-438 | H | CF$_3$ | H | CF$_3$ | H |
| A-439 | H | CF$_3$ | H | CH$_2$CF$_3$ | H |
| A-440 | H | CF$_3$ | H | CH$_2$CH$_3$ | H |
| A-441 | H | CF$_3$ | H | OCH$_3$ | H |
| A-442 | H | CF$_3$ | H | OCF$_3$ | H |
| A-443 | H | CH$_2$CF$_3$ | CH$_3$ | H | H |
| A-444 | H | CH$_2$CF$_3$ | Cl | H | H |
| A-445 | H | CH$_2$CF$_3$ | Br | H | H |
| A-446 | H | CH$_2$CF$_3$ | I | H | H |
| A-447 | H | CH$_2$CF$_3$ | CF$_3$ | H | H |
| A-448 | H | CH$_2$CF$_3$ | CH$_2$CF$_3$ | H | H |
| A-449 | H | CH$_2$CF$_3$ | CH$_2$CH$_3$ | H | H |
| A-450 | H | CH$_2$CF$_3$ | OCH$_3$ | H | H |
| A-451 | H | CH$_2$CF$_3$ | OCF$_3$ | H | H |
| A-452 | H | CH$_2$CF$_3$ | H | CH$_3$ | H |
| A-453 | H | CH$_2$CF$_3$ | H | Cl | H |
| A-454 | H | CH$_2$CF$_3$ | H | Br | H |
| A-455 | H | CH$_2$CF$_3$ | H | I | H |
| A-456 | H | CH$_2$CF$_3$ | H | CF$_3$ | H |
| A-457 | H | CH$_2$CF$_3$ | H | CH$_2$CF$_3$ | H |
| A-458 | H | CH$_2$CF$_3$ | H | CH$_2$CH$_3$ | H |
| A-459 | H | CH$_2$CF$_3$ | H | OCH$_3$ | H |
| A-460 | H | CH$_2$CF$_3$ | H | OCF$_3$ | H |
| A-461 | H | CH$_2$CH$_3$ | CH$_3$ | H | H |
| A-462 | H | CH$_2$CH$_3$ | Cl | H | H |
| A-463 | H | CH$_2$CH$_3$ | Br | H | H |
| A-464 | H | CH$_2$CH$_3$ | I | H | H |
| A-465 | H | CH$_2$CH$_3$ | CF$_3$ | H | H |
| A-466 | H | CH$_2$CH$_3$ | CH$_2$CF$_3$ | H | H |
| A-467 | H | CH$_2$CH$_3$ | CH$_2$CH$_3$ | H | H |
| A-468 | H | CH$_2$CH$_3$ | OCH$_3$ | H | H |

TABLE A-continued

| No. | $R^{10a}$ | $R^{10b}$ | $R^{10c}$ | $R^{10d}$ | $R^{10e}$ |
|---|---|---|---|---|---|
| A-469 | H | $CH_2CH_3$ | $OCF_3$ | H | H |
| A-470 | H | $CH_2CH_3$ | H | $CH_3$ | H |
| A-471 | H | $CH_2CH_3$ | H | Cl | H |
| A-472 | H | $CH_2CH_3$ | H | Br | H |
| A-473 | H | $CH_2CH_3$ | H | I | H |
| A-474 | H | $CH_2CH_3$ | H | $CF_3$ | H |
| A-475 | H | $CH_2CH_3$ | H | $CH_2CF_3$ | H |
| A-476 | H | $CH_2CH_3$ | H | $CH_2CH_3$ | H |
| A-477 | H | $CH_2CH_3$ | H | $OCH_3$ | H |
| A-478 | H | $CH_2CH_3$ | H | $OCF_3$ | H |
| A-479 | H | $OCH_3$ | $CH_3$ | H | H |
| A-480 | H | $OCH_3$ | Cl | H | H |
| A-481 | H | $OCH_3$ | Br | H | H |
| A-482 | H | $OCH_3$ | I | H | H |
| A-483 | H | $OCH_3$ | $CF_3$ | H | H |
| A-484 | H | $OCH_3$ | $CH_2CF_3$ | H | H |
| A-485 | H | $OCH_3$ | $CH_2CH_3$ | H | H |
| A-486 | H | $OCH_3$ | $OCH_3$ | H | H |
| A-487 | H | $OCH_3$ | $OCF_3$ | H | H |
| A-488 | H | $OCH_3$ | H | $CH_3$ | H |
| A-489 | H | $OCH_3$ | H | Cl | H |
| A-490 | H | $OCH_3$ | H | Br | H |
| A-491 | H | $OCH_3$ | H | I | H |
| A-492 | H | $OCH_3$ | H | $CF_3$ | H |
| A-493 | H | $OCH_3$ | H | $CH_2CF_3$ | H |
| A-494 | H | $OCH_3$ | H | $CH_2CH_3$ | H |
| A-495 | H | $OCH_3$ | H | $OCH_3$ | H |
| A-496 | H | $OCH_3$ | H | $OCF_3$ | H |
| A-497 | H | $OCF_3$ | $CH_3$ | H | H |
| A-498 | H | $OCF_3$ | Cl | H | H |
| A-499 | H | $OCF_3$ | Br | H | H |
| A-500 | H | $OCF_3$ | I | H | H |
| A-501 | H | $OCF_3$ | $CF_3$ | H | H |
| A-502 | H | $OCF_3$ | $CH_2CF_3$ | H | H |
| A-503 | H | $OCF_3$ | $CH_2CH_3$ | H | H |
| A-504 | H | $OCF_3$ | $OCH_3$ | H | H |
| A-505 | H | $OCF_3$ | $OCF_3$ | H | H |
| A-506 | H | $OCF_3$ | H | $CH_3$ | H |
| A-507 | H | $OCF_3$ | H | Cl | H |
| A-508 | H | $OCF_3$ | H | Br | H |
| A-509 | H | $OCF_3$ | H | I | H |
| A-510 | H | $OCF_3$ | H | $CF_3$ | H |
| A-511 | H | $OCF_3$ | H | $CH_2CF_3$ | H |
| A-512 | H | $OCF_3$ | H | $CH_2CH_3$ | H |
| A-513 | H | $OCF_3$ | H | $OCH_3$ | H |
| A-514 | H | $OCF_3$ | H | $OCF_3$ | H |
| A-515 | H | $OCF_3$ | H | H | H |
| A-516 | H | $OCF_3$ | H | H | H |
| A-517 | H | $OCF_3$ | H | H | H |
| A-518 | H | $OCF_3$ | H | H | H |
| A-519 | H | $OCF_3$ | H | H | H |
| A-520 | H | $OCF_3$ | H | H | H |
| A-521 | H | $OCF_3$ | H | H | H |
| A-522 | H | $OCF_3$ | H | H | H |
| A-523 | H | $OCF_3$ | H | H | H |
| A-524 | H | $OCF_3$ | H | H | H |
| A-525 | H | $OCF_3$ | H | H | H |
| A-526 | H | $OCF_3$ | H | H | H |
| A-527 | H | $OCF_3$ | H | H | H |
| A-528 | H | $OCF_3$ | H | H | H |
| A-529 | H | $OCF_3$ | H | H | H |
| A-530 | H | $OCF_3$ | H | H | H |
| A-531 | H | $OCF_3$ | H | H | H |
| A-532 | H | $OCF_3$ | H | H | H |
| A-533 | H | $CH_3$ | $CH_3$ | $CH_3$ | H |
| A-534 | H | $CH_3$ | $CH_3$ | Cl | H |
| A-535 | H | $CH_3$ | $CH_3$ | Br | H |
| A-536 | H | $CH_3$ | $CH_3$ | I | H |
| A-537 | H | $CH_3$ | $CH_3$ | $CF_3$ | H |
| A-538 | H | $CH_3$ | $CH_3$ | $CH_2CF_3$ | H |
| A-539 | H | $CH_3$ | $CH_3$ | $CH_2CH_3$ | H |
| A-540 | H | $CH_3$ | $CH_3$ | $OCH_3$ | H |
| A-541 | H | $CH_3$ | $CH_3$ | $OCF_3$ | H |
| A-542 | H | $CH_3$ | Cl | $CH_3$ | H |
| A-543 | H | Cl | Cl | Cl | H |
| A-544 | H | Br | Cl | Br | H |
| A-545 | H | I | Cl | I | H |
| A-546 | H | $CF_3$ | Cl | $CF_3$ | H |
| A-547 | H | $CH_2CF_3$ | Cl | $CH_2CF_3$ | H |
| A-548 | H | $CH_2CH_3$ | Cl | $CH_2CH_3$ | H |
| A-549 | H | $OCH_3$ | Cl | $OCH_3$ | H |
| A-550 | H | $OCF_3$ | Cl | $OCF_3$ | H |
| A-551 | H | $CH_3$ | Br | $CH_3$ | H |
| A-552 | H | Cl | Br | Cl | H |
| A-553 | H | Br | Br | Br | H |
| A-554 | H | I | Br | I | H |
| A-555 | H | $CF_3$ | Br | $CF_3$ | H |
| A-556 | H | $CH_2CF_3$ | Br | $CH_2CF_3$ | H |
| A-557 | H | $CH_2CH_3$ | Br | $CH_2CH_3$ | H |
| A-558 | H | $OCH_3$ | Br | $OCH_3$ | H |
| A-559 | H | $OCF_3$ | Br | $OCF_3$ | H |
| A-560 | H | $CH_3$ | I | $CH_3$ | H |
| A-561 | H | Cl | I | Cl | H |
| A-562 | H | Br | I | Br | H |
| A-563 | H | I | I | I | H |
| A-564 | H | $CF_3$ | I | $CF_3$ | H |
| A-565 | H | $CH_2CF_3$ | I | $CH_2CF_3$ | H |
| A-566 | H | $CH_2CH_3$ | I | $CH_2CH_3$ | H |
| A-567 | H | $OCH_3$ | I | $OCH_3$ | H |
| A-568 | H | $OCF_3$ | I | $OCF_3$ | H |
| A-569 | H | $CH_3$ | $CF_3$ | $CH_3$ | H |
| A-570 | H | Cl | $CF_3$ | Cl | H |
| A-571 | H | Br | $CF_3$ | Br | H |
| A-572 | H | I | $CF_3$ | I | H |
| A-573 | H | $CF_3$ | $CF_3$ | $CF_3$ | H |
| A-574 | H | $CH_2CF_3$ | $CF_3$ | $CH_2CF_3$ | H |
| A-575 | H | $CH_2CH_3$ | $CF_3$ | $CH_2CH_3$ | H |
| A-576 | H | $OCH_3$ | $CF_3$ | $OCH_3$ | H |
| A-577 | H | $OCF_3$ | $CF_3$ | $OCF_3$ | H |
| A-578 | H | $CH_3$ | $CF_3$ | $CH_3$ | H |
| A-579 | H | Cl | $CH_2CF_3$ | Cl | H |
| A-580 | H | Br | $CH_2CF_3$ | Br | H |
| A-581 | H | I | $CH_2CF_3$ | I | H |
| A-582 | H | $CF_3$ | $CH_2CF_3$ | $CF_3$ | H |
| A-583 | H | $CH_2CF_3$ | $CH_2CF_3$ | $CH_2CF_3$ | H |
| A-584 | H | $CH_2CH_3$ | $CH_2CF_3$ | $CH_2CH_3$ | H |
| A-585 | H | $OCH_3$ | $CH_2CF_3$ | $OCH_3$ | H |
| A-586 | H | $OCF_3$ | $CH_2CF_3$ | $OCF_3$ | H |
| A-587 | H | $CH_3$ | $CH_2CF_3$ | $CH_3$ | H |
| A-588 | H | Cl | $OCH_3$ | Cl | H |
| A-589 | H | Br | $OCH_3$ | Br | H |
| A-590 | H | I | $OCH_3$ | I | H |
| A-591 | H | $CF_3$ | $OCH_3$ | $CF_3$ | H |
| A-592 | H | $CH_2CF_3$ | $OCH_3$ | $CH_2CF_3$ | H |
| A-593 | H | $CH_2CH_3$ | $OCH_3$ | $CH_2CH_3$ | H |
| A-594 | H | $OCH_3$ | $OCH_3$ | $OCH_3$ | H |
| A-595 | H | $OCF_3$ | $OCH_3$ | $OCF_3$ | H |
| A-596 | H | $CH_3$ | $OCH_3$ | $CH_3$ | H |
| A-597 | H | Cl | $OCF_3$ | Cl | H |
| A-598 | H | Br | $OCF_3$ | Br | H |
| A-599 | H | I | $OCF_3$ | I | H |
| A-600 | H | $CF_3$ | $OCF_3$ | $CF_3$ | H |
| A-601 | H | $CH_2CF_3$ | $OCF_3$ | $CH_2CF_3$ | H |
| A-602 | H | $CH_2CH_3$ | $OCF_3$ | $CH_2CH_3$ | H |
| A-603 | H | $OCH_3$ | $OCF_3$ | $OCH_3$ | H |
| A-604 | H | $OCF_3$ | $OCF_3$ | $OCF_3$ | H |
| A-605 | H | —$OCH_2O$— | | H | H |
| A-606 | H | —$OCH_2O$— | | $CH_3$ | H |
| A-607 | H | —$OCH_2O$— | | Cl | H |
| A-608 | H | —$OCH_2O$— | | Br | H |
| A-609 | H | —$OCH_2O$— | | I | H |
| A-610 | H | —$OCH_2O$— | | $CF_3$ | H |
| A-611 | H | —$OCH_2O$— | | $CH_2CF_3$ | H |
| A-612 | H | —$OCH_2O$— | | $CH_2CH_3$ | H |
| A-613 | H | —$OCH_2O$— | | $OCH_3$ | H |
| A-614 | H | —$OCH_2O$— | | $OCF_3$ | H |
| A-615 | $CH_3$ | —$OCH_2O$— | | H | H |
| A-616 | Cl | —$OCH_2O$— | | H | H |
| A-617 | Br | —$OCH_2O$— | | H | H |
| A-618 | I | —$OCH_2O$— | | H | H |
| A-619 | $CF_3$ | —$OCH_2O$— | | H | H |
| A-620 | $CH_2CF_3$ | —$OCH_2O$— | | H | H |
| A-621 | $CH_2CH_3$ | —$OCH_2O$— | | H | H |
| A-622 | $OCH_3$ | —$OCH_2O$— | | H | H |
| A-623 | $OCF_3$ | —$OCH_2O$— | | H | H |
| A-624 | H | —$OCH_2O$— | | H | $CH_3$ |

TABLE A-continued

| No. | $R^{10a}$ | $R^{10b}$ | $R^{10c}$ | $R^{10d}$ | $R^{10e}$ |
|---|---|---|---|---|---|
| A-625 | H | | —OCH$_2$O— | H | Cl |
| A-626 | H | | —OCH$_2$O— | H | Br |
| A-627 | H | | —OCH$_2$O— | H | I |
| A-628 | H | | —OCH$_2$O— | H | CF$_3$ |
| A-629 | H | | —OCH$_2$O— | H | CH$_2$CF$_3$ |
| A-630 | H | | —OCH$_2$O— | H | CH$_2$CH$_3$ |
| A-631 | H | | —OCH$_2$O— | H | OCH$_3$ |
| A-632 | H | | —OCH$_2$O— | H | OCF$_3$ |

Preparation Methods

The compounds of the formula (I) according to the present invention can be prepared by standard methods of organic chemistry, e.g. by the preparation methods and preparation schemes as described below and in the synthesis descriptions of the working examples. The substituents, variables and indices in the following schemes and methods correspond to the definitions given for formula (I) above, if not otherwise specified. Room temperature means a temperature range between about 20 and 25° C.

Compounds of the formula (I-1) can be prepared as shown in the Scheme 1 below. Compounds of formula (I-1) are compounds of formula (I) wherein $R^3$ and $R^4$ form together with the nitrogen they are bound to a group of the formula A.1, in which t is 0.

Scheme 1

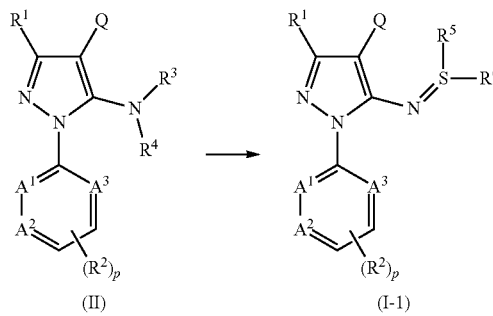

Compounds of formula (II) are reacted with dialkyl sulfides under activation with chlorine to give compounds of formula (I-1). A representative procedure has been described in WO 98/21178. Alternatively, compounds of formula (I-1) can be prepared from pyrazole amines of formula (II) by reaction of an activated dialkyl sulfoxide, as for example described by Mace, et al, Tetrahedron (2011), 67, 7575-7580.

Compounds of formula I-1 with t=1 can be prepared by oxidation reaction of the corresponding sulfimine, as for example described by Veale et al, Tetrahedron Letters (1978), (6), 503-506.

Compounds of formula (II) are known from WO 2010/017902 and can be prepared by one of the published methods therein.

Compounds of the formula (I-2) to (I-4) can be prepared as shown in the Scheme 2 below.

Scheme 2

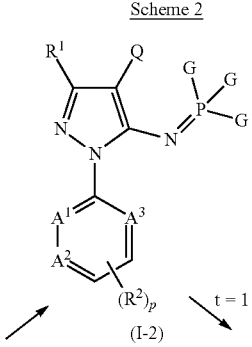

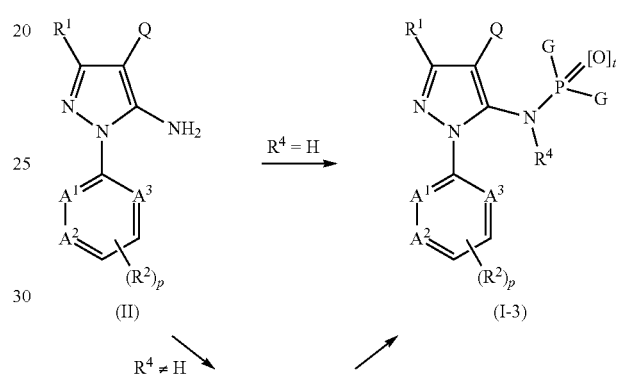

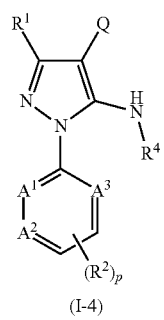

Compounds of formula (I-3), in which $R^4$ is hydrogen, can be prepared directly from compounds of formula (II) by reaction with a halogen phosphate, as for example described in WO 2005/082916. Compounds of formula (I-3), in which $R^4$ is not hydrogen, can be prepared from compounds of formula (I-4) by the same means, after introducing $R^4$. In the latter case, compounds of formula (I-4) can be prepared by alkylation reaction of compounds of formula (II), as for example described by Yang et al, Journal of Agricultural and Food Chemistry (2011), 59, 12534-12542.

Alternatively, compounds of formula (I-3) can be prepared from compounds of formula (I-2) with t=1 by cleavage of one G-residue, as for example described in DE 3545347. Compounds of formula (I-2) can be prepared from compounds of formula (II) as for example described by Alajarin et al, European Journal of Organic Chemistry (2011), (10), 1896-1913.

Compounds of formula (I-5) can be prepared as shown in the Scheme 3 below.

Scheme 3

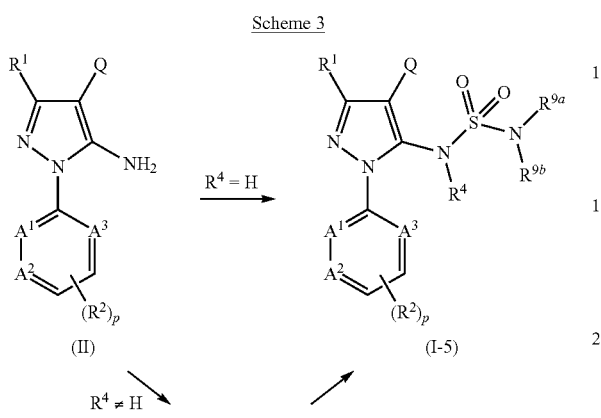

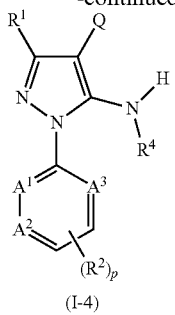

(I-4)

Compounds of formula (I-5), in which $R^4$ is hydrogen, can be prepared from compounds of formula (II) by reaction with a sulfamoyl chloride, as for example described by Wamhoff et al, Synthesis (1985), 190-194. Compounds of formula (I-5), in which $R^4$ is not hydrogen, can be prepared from compounds of formula (I-4), which in turn can be prepared as described above in Scheme 2.

Compounds of formula (I-6) and (I-7) can be prepared as shown in the Scheme 4 below.

Scheme 4

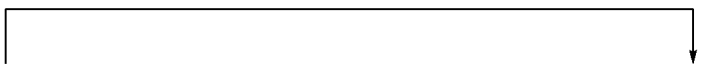

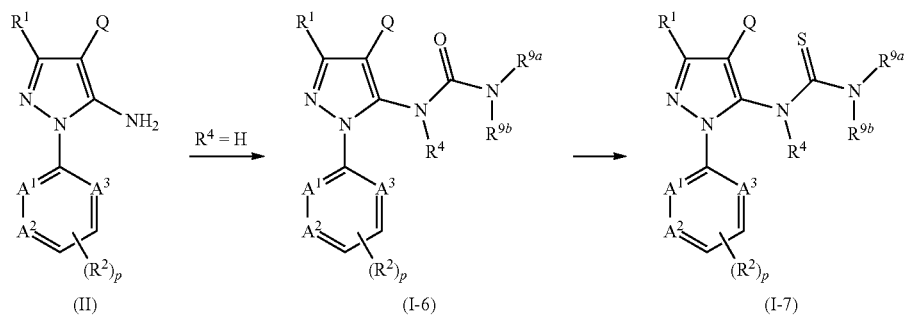

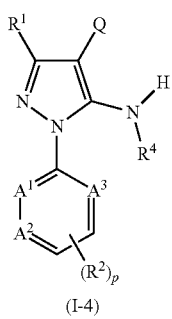

(I-4)

Compounds of formula (I-6), in which $R^4$ is hydrogen, can be prepared from compounds of formula (II) by reaction with an isocyanate, as for example described by Moffett et al, Bioorganic & Medicinal Chemistry Letters (2011), 21, 7155-7165. Compounds of formula (I-6), in which $R^4$ is not hydrogen, can be prepared from compounds of formula (I-4), which in turn can be prepared as described above in Scheme 2.

Compounds of formula (I-7) can be prepared from compounds of formula (I-6) by thionylation with for example Lawesson's reagent, as for instance described by Zhang et al, Bioorganic & Medicinal Chemistry (2007), 15, 6556-6564.

Alternatively, compounds of formula (I-7) can be prepared from compounds of formula (II) by reaction with an isothiocyanate, as for example described by Saito et al, Bioorganic & Medicinal Chemistry (2011), 19, 5955-5966.

Compounds of formula (I-8) and (I-9) can be prepared as shown in the Scheme 5 below.

Scheme 5

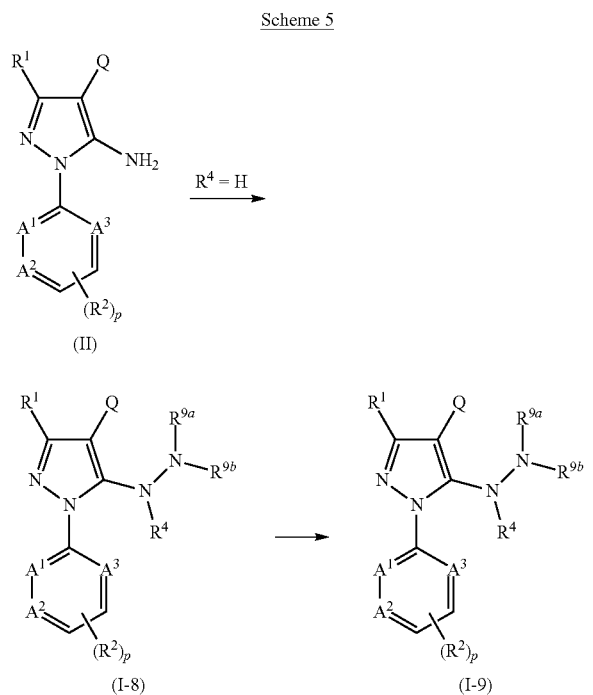

(I-8)    (I-9)

Compounds of formula (I-8), in which $R^4$ is hydrogen, can be prepared from compounds of formula (II) by diazotation and reduction, as for example described by Baheti et al, Journal of Heterocyclic Chemistry (2003), 40, 547-551. Alternatively, the above prepared diazonium ion may also be reacted with an amine to obtain azides of formula (I-8), as for example described by Ege et al, Chemische Berichte (1987), 120, 1375-95.

Compounds of formula (I-9), in which $R^4$ is not hydrogen, may be prepared by alkylation reaction, as described in the previous examples above.

Alternatively, compounds of formula II may be first subjected to alkylation, leading to compounds of formula (I-4) as described above, and then converted to compounds of formula (I-9), thus changing the order of reaction steps.

Compounds of formula (I-10) can be prepared as shown in the Scheme 6 below.

Scheme 6

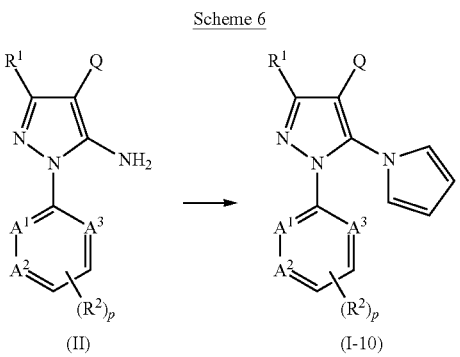

(II)    (I-10)

Compounds of formula (I-10) can be prepared from compounds of formula (II) by reaction with 2,5-dimethoxytetrahydrofuran, as for example described by Massa et al, Journal of Heterocyclic Chemistry (1984), 21, 1877-1880.

Other rings, which may be formed by $R^3$ and $R^4$ together with the nitrogen atom to which they are bound, can be synthesized starting from the amino function in compound of formula (II), by customary methods of synthesis for heterocycles, which is known to the person skilled in the art.

Compounds of formula I with $R^3$ equaling nitro can be prepared as for example described by Brocklehurst et al, Organic Process Research & Development (2011), 15(6), 1447-1453. Compounds of formula I with $R^3$ equaling —C(=NR$^{9a}$)—S(O)$_m$R$^8$ can be prepared as for example described by Chanda et al, Tetrahedron (2011), 67(34), 6214-6220.

As a rule, the compounds of formula (I), especially (I-1), (I-2), (I-3), (I-4), (I-5), (I-6), (I-7), (I-8), (I-9), (I-10), including their stereoisomers, N-oxides, tautomers and salts, and their precursors in the synthesis process, especially (II), can be prepared by the methods described above or by customary modifications of the synthesis routes described. If individual compounds can not be prepared via the above-described routes, they can be prepared by derivatization of other compounds (I) or the respective precursor. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration with an appropriate solvent.

Pests

The compounds of the formula I, and their stereoisomers, N-oxides, tautomers and salts, are in particular suitable for efficiently controlling arthropodal pests such as arachnids, myriapedes and insects as well as nematodes. The compounds of the formula I are especially suitable for efficiently combating the following pests:

Insects from the order of the lepidopterans (Lepidoptera), for example Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria melonella, Grapholitha funebrana, Grapholitha molesta, Heliothis armigera, Heliothis virescens, Heliothis zea, Hellula undalis, Hibernia defoliaria, Hyphantria cunea, Hyponomeuta malineus, Keiferia lycopersicea, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiea, Peridroma saucia, Phalera bucephala, Phthorimaea operculella, Phyiocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

beetles (Coleoptera), for example *Agrilus sinuatus, Agriotes lineatus, Agriotes obscurus, Amphimaus solstitialis, Anisandrus dispar, Anthonomus grandis, Anthonomus pomorum, Aphthona euphoridae, Athous haemorrhoidalls, Atomaria linearis, Blastophagus piniperda, Bllitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica* 12-*punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemllineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyobius pyr, Phyotreta chrysocephala, Phyophaga* sp., *Phyopertha horticola, Phyotreta nemorum, Phyotreta striolata, Popilla japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborn, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atllanticus, Cochliomyla hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyla platura, Hypoderma llineata, Leptoconops torrens, Liriomyza sativae, Liriomyza trifoli Lucllia caprina, Lucllia cuprina, Lucilia sericata, Lycoria pectoralls, Mansonia titilllanus, Mayetiola destructor, Musca autumnalis, Musca domestica, Muscina stabulans, Oestrus ovis, Opomyza florum, Oscinella frit, Pegomya hysocyami Phorbia antiqua, Phorbia brassicae, Phorbia coarctata, Phlebotomus argentipes, Psorophora columbiae, Psila rosae, Psorophora discolor, Prosimullum mixtum, Rhagoletis cerasl Rhagoletis pomonea, Sarcophaga haemorrhoidalls, Sarcophaga* spp., *Simullium vittatum, Stomoxys calcitrans, Tabanus bovinus, Tabanus atratus, Tabanus lineola,* and *Tabanus similis, Tipula oleracea,* and *Tipula paludosa,* thrips (Thysanoptera), e.g. *Dichromothrips corbetti, Dichromothrips* ssp., *Frankliniella fusca, Frankliniella occidentalis, Frankiniella tritici Scirtothrips citri Thrips oryzae, Thrips palmi* and *Thrips tabaci,* termites (Isoptera), e.g. *Calotermes flavicolis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus,* cockroaches (Blattaria-Blattodea), e.g. *Battella germanica, Battella asahinae, Periplaneta americana, Periplaneta japonica, Periplaneta brunnea, Periplaneta fuligginosa, Periplaneta australasiae,* and *Blatta orientalis,* bugs, aphids, leafhoppers, whiteflies, scale insects, cicadas (Hemiptera), e.g. *Acrosternum hillare, Blissus leucopterus, Cyrtopeltis notatus, Dysdercus cingulatus, Dysdercus intermedius, Eurygaster integriceps, Euschistus impictiventris, Leptoglossus phyopus, Lygus lineolaris, Lygus pratensis, Nezara viridula, Piesma quadrata, Solubea insularis, Thyanta perdlitor, Acyrthosiphon onobrychis, Adelges laricis, Aphidula nasturti, Aphis fabae, Aphis forbes, Aphis pom Aphis gossypil Aphis grossulariae, Aphis schneiderl Aphis spiraecola, Aphis sambucl Acyrthosiphon pisum, Aulacorthum solan Bemisia argentifoli Brachycaudus cardu Brachycaudus helichrysi Brachycaudus persicae, Brachycaudus prunicola, Brevicoryne brassicae, Capitophorus horn, Cerosipha gossypi, Chaetosiphon fragaefolii, Cryptomyzus ribis, Dreyfusia nordmannlanae, Dreyfusia piceae, Dysaphis radicola, Dysaulacorthum pseudosolani, Dysaphis plantaginea, Dysaphis pyr, Empoasca fabae, Hyalopterus prun, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasl Myzus varians, Nasonovia ribis-nigr Nilaparvata lugens, Pemphigus bursarius, Perkinsiella saccharicida, Phorodon humul Psylla malli Psylla pirl Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolil Cimex llectularius, Cimex hemipterus, Reduvius senllis, Triatoma* spp., *and Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryotalpa gryotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angullifera, Captamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersonl Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnin, Dermanyssus gallinae, Psoroptes ovis, Rhipicephalus sanguineus, Rhipicephalus appendiculatus, Rhipicephalus evertsi, Sarcoptes scabiei* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawa, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephallides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of the present invention, including their salts, N-oxides and stereoisomers are also suitable for controlling nematodes, especially plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species, *Heterodera avenae, Heterodera glycines, Heterodera schachti, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the present invention, including their salts, N-oxides, tautomers and stereoisomers are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor sillvarum, Hyalomma truncatum, Ixodes ricinus, Ixodes rubicundus, Ornithodorus moubata, Otobius megnini Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Compounds of the formula I are particularly useful for controlling insects, preferably sucking or piercing insects such as insects from the genera Thysanoptera, Diptera and Hemiptera, and chewing-biting pests such as insects from the genera of Lepidoptera, in particular the following species:

Thysanoptera: *Frankliniella fusca, Frankliniella occidentalis, Frankliniella tritici Scirtothrips citri, Thrips oryzae, Thrips palmi* and *Thrips tabaci,*

Diptera, e.g. *Aedes aegypti Aedes albopictus, Aedes vexans, Anastrepha ludens, Anopheles maculipennis, Anopheles crucians, Anopheles albimanus, Anopheles gambiae, Anopheles freeborni Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argenties, Psorophora columbiae, Psila rosae, Psorophora discolor, Prosimulium mixtum, Rhagoletis ceras, Rhagoletis pomonella, Sarcophaga haemorrhoidalis, Sarcophaga* spp., *Simulium vittatum, Stomoxys calcitrans,*

*Tabanus bovinus, Tabanus atratus, Tabanus lineola*, and *Tabanus similis, Tipula oleracea*, and *Tipula paludosa;*

Hemiptera, in particular aphids: *Acyrthosiphon onobrychis, Adelges laricis, Aphidula nasturti, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solan Brachycaudus cardui, Brachycaudus helichrysi Brachycaudus persicae, Brachycaudus prunicola, Brevicoryne brassicae, Capitophorus horni, Cerosipha gossypi, Chaetosiphon fragaefolii, Cryptomyzus ribis, Dreyfusia nordmannianae, Dreyfusia piceae, Dysaphis radicola, Dysaulacorthum pseudosolan, Dysaphis plantaginea, Dysaphis pyr, Empoasca fabae, Hyalopterus prun, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigr Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii.*

Lepidoptera, in particular: *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Compounds of the formula I are particularly useful for controlling insects of the orders Hemiptera and Thysanoptera.

Formulations

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling invertebrate pests on cultivated plants or in the protection of materials and which does not result in a substantial damage to the treated plants or material. Such an amount can vary in a broad range and is dependent on various factors, such as the invertebrate (e.g. insect) species to be controlled, the treated cultivated plant or material, the climatic conditions and the specific compound I used.

The compounds I, their stereoisomers, N-oxides, tautomers and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
 i) Water-soluble concentrates (SL, LS)
 10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible concentrates (DC)
 5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable concentrates (EC)
 15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
 5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)
 In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)
 50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)
 50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)
 In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

iv) Microemulsion (ME)
 5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)
 An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable powders (DP, DS)

1-10 wt % of a compound I according to the invention are ground finely and mixed intimately with up to 100 wt % solid carrier, e.g. finely divided kaolin.

x) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xi) Ultra-low volume liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds I and/or active substances from the groups A) to O), may be mixed by the user in a spray tank and further auxiliaries and additives may be added, if appropriate.

In a further embodiment, either individual components of the composition according to the invention or partially premixed components, e.g. components comprising compounds I and/or active substances from the groups A) to O), can be applied jointly (e.g. after tank mix) or consecutively.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

Therefore, the present invention also relates to a mixture or composition comprising at least one compound of formula (I), or a stereoisomer or agriculturally or veterinarily acceptable salt thereof, and at least one further pesticide.

The following categorized list M of pesticides represents insecticidal mixture partners, which are, whenever possible, classified according to the Insecticide Resistance Action Committee (IRAC), and together with which the compounds according to the present invention may be used. The combined use of the compounds of the present invention with the following pesticides may result in potential synergistic effects. The following examples of insecticidal mixing partners are provided with the intention to illustrate the possible combinations, but not to impose any limitation to the obtainable mixtures:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb, or M.7C pyriproxyfen;

M.8 miscellaneous non-specific (multi-site) inhibitors, for example

M.8A alkyl halides as methyl bromide and other alkyl halides, or

M.8B chloropicrin, or

M.8C sulfuryl fluoride, or

M.8D borax, or

M.8E tartar emetic;

M.9 Selective homopteran feeding blockers, for example

M.9B pymetrozine, or

M.9C flonicamid;

M.10 Mite growth inhibitors, for example

M.10A clofentezine, hexythiazox and diflovidazin, or

M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis*, *bacillus sphaericus*, *bacillus thuringiensis* subsp. *aizawai*, *bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or

M.20B acequinocyl, or

M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or

M.22B metaflumizone;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.26 Ryanodine receptor-modulators from the class of diamides, as for example flubendiamide, chlorantraniliprole (Rynaxypyr®), cyantraniliprole (Cyazypyr®), or the phthalamide compounds M.26.1: (R)-3-Chlor-N1-{2-methyl-4-[1,2,2,2-tetrafluor-1-(trifluormethyl)ethyl]phenyl}-N2-(1-methyl-2-methyl-sulfonylethyl)phthalamid and M.26.2: (S)-3-Chlor-N1-{2-methyl-4-[1,2,2,2-tetrafluor-1-(trifluormethyl)ethyl]phenyl}-N2-(1-methyl-2-methyl-sulfonylethyl)phthalamid, or the compound M.26.3: 3-bromo-N-{2-bromo-4-chloro-6-[(1-cyclopropyl-ethyl)carbamoyl]phenyl}-1-(3-chlorpyridin-2-yl)-1H-pyrazole-5-carboxamide (proposed ISO name: cyclaniliprole), or the compound M.26.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.26.5a) to M.26.5h):

M.26.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.26.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.26.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.26.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.26.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.26.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.26.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.26.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide.

M.X insecticidal active compounds of unknown or uncertain mode of action, as for example azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, or the compound M.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound M.X.2: cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester, or the compound M.X.3: 11-(4-chloro-2,6-dimethylphenyl)-12-hydroxy-1,4-dioxa-9-azadispiro[4.2.4.2]-tetradec-11-en-10-one, or the compound M.X.4: 3-(4'-fluoro-2,4-dimethylbiphenyl-3-yl)-4-hydroxy-8-oxa-1-azaspiro[4.5]dec-3-en-2-one, or the compound M.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582).

The commercially available compounds of the group M listed above may be found in The Pesticide Manual, 15th Edition, C. D. S. Tomlin, British Crop Protection Council (2011) among other publications.

The phthalamides M.26.1 and M.26.2 are both known from WO 2007/101540. The anthranilamide M.26.3 has been described in WO2005/077934. The hydrazide compound M.26.4 has been described in WO 2007/043677. The anthranilamides M.26.5a) to M.26.5h) can be prepared as described in WO 2007/006670, WO2013/024009 and WO2013/024010. The quinoline derivative flometoquin is shown in WO2006/013896. The aminofuranone compounds flupyradifurone is known from WO 2007/115644. The sulfoximine compound sulfoxaflor is known from WO2007/149134. The isoxazoline compound M.X.1 has been described in WO2005/085216. The pyripyropene derivative M.X.2 has been described in WO 2006/129714. The spiroketal-substituted cyclic ketoenol derivative M.X.3 is known from WO2006/089633 and the biphenyl-substituted spirocyclic ketoenol derivative M.X.4 from WO2008/067911. Finally triazoylphenylsulfide like M.X.5 have been described in WO2006/043635 and biological control agents on basis of *bacillus firmus* in WO2009/124707.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxy-imino-N methyl-acetamide;

oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4-carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl) pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoroquinazolin-4-yl)-{2-[2-fluoro-4-(4-trifluoromethylpyridin-2-yloxy)-phenyl]-ethyl}-amine; tecnazen; ametoctradin; silthiofam; nitrophenyl derivates: binapacryl, dinobuton, dinocap, fluazinam, ferimzone, nitrthal-isopropyl, and including organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[rel-(2S,3R)-3-(2-chloro-phenyl)-2-(2,4-difluorophenyl)-oxiranylmethyl]-5-thiocyanato-1H-[1,2,4]triazole, 2-[rel-(2S;3R-3-(2-chlorophenyl)-2-(2,4-difluorophenyl)-oxiranylmethyl]-2H-[1,2,4]triazole-3-thiol; imidazoles: imazalil, pefurazoate, oxpoconazole, prochloraz, triflumizole; pyrimidines, pyridines and piperazines: fenarimol, nuarimol, pyrifenox, triforine, 1-[rel-(2S,3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol;

F.II-2) Delta14-reductase inhibitors (Amines, e.g. morpholines, piperidines) morpholines: aldimorph, dodemorph, dodemorph-acetate, fenpropimorph, tridemorph; piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase), hydroxy(2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)-[1,2,4]triazolo[1,5a]pyrimidine;

F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone, pyriofenone;

F.V) Inhibitors of amino acid and protein synthesis

F.V-1) Methionine synthesis inhibitors (anilino-pyrimidines) anilino-pyrimidines: cyprodinil, mepanipyrim, nitrapyrin, pyrimethanil;

F.V-2) Protein synthesis inhibitors (anilino-pyrimidines)

antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)

dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos;

dithiolanes: isoprothiolane;

F.VII-2) Lipid peroxidation: aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandipropamid, pyrimorph; valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acids: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarb-hydrochlorid, F.VII-5) fatty acid amide hydrolase inhibitors: 1-[4-[4-[5-(2,6-difluorophenyl)-4,5-dihydro-3-isoxazolyl]-2-thiazolyl]-1-piperid inyl]-2-[5-methyl-3-(trifluoromethyl)-1H-pyrazol-1-yl]ethanone;

F.VIII) Inhibitors with Multi Site Action

F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7 (2H,6H)-tetraone;

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium; phosphonates: fosetyl, fosetyl-aluminum, phosphorous acid and its salts;

F.XI) Unknown mode of action:bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide.

F.XI) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents

*Ampelomyces quisqualis* (e.g. AQ 10® from Intrachem Bio GmbH & Co. KG, Germany), *Aspergillus flavus* (e.g. AFLA-GUARD® from Syngenta, CH), *Aureobasidium pullulans* (e.g. BOTECTOR® from bio-ferm GmbH, Germany), Bacilluspumilus (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIO-CURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. Endothia parasitica from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. afroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ).

The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP A 141 317; EP-A 152 031; EP-A 226 917; EP A 243 970; EP A 256 503; EP-A 428 941; EP-A 532 022; EP-A 1 028 125; EP-A 1 035 122; EP A 1 201 648; EP A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

Applications

Due to their excellent activity, the compounds of the present invention may be used for controlling invertebrate pests.

The animal pest (also referred to as "invertebrate pest"), i.e. the insects, arachnids and nematodes, the plant, soil or water in which the plant is growing can be contacted with the present compounds of formula I or composition(s) comprising them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habitat, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I. Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, the genetic material of which has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5): 1225-35., Curr Opin Chem Biol. 2006 October; 10(5): 487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment of seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight. Seed Treatment formulations may additionally also comprise binders and optionally colorants. Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the stereoisomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals.

Another object of the invention is further to provide pesticides for animals that may be used in lower doses than existing pesticides. And another object of the invention is to provide pesticides for animals, which provide a long residual control of the parasites.

The invention also relates to compositions comprising a parasitically effective amount of compounds of formula I or the stereoisomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the stereoisomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the stereoisomers or veterinarily acceptable salts thereof or a composition comprising it.

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the stereoisomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the stereoisomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the stereoisomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and Nosopsyllus fasciatus, cockroaches (Blattaria-Blattodea), e.g. *Battella germanica, Battella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Luciila sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vitul, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Omithodorus hermsi, Omithodorus turicata* and parasitic mites (Mesostigmata), e.g. *Omithonyssus bacotiand Dermanyssus gallinae,*

Actinedida (Prostigmata) und Acaridida (Astigmata) e.g. *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Ca/oglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *and Laminosioptes* spp, Bugs (Heteropterida): *Cimex lectularius, Cimex hemipterus, Reduvius senils, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necatoramericanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles. Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary. Solutions for use on the skin are trickled on, spread on, rubbed in, sprinkled on or sprayed on. Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight. Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

EXAMPLES

The present invention is now illustrated in further details by the following examples, without imposing any limitation thereto.

The compounds can be characterized e.g. by coupled High Performance Liquid Chromatography/mass spectrometry (HPLC/MS), by $^1$H-NMR and/or by their melting points.

The following analytical procedures were employed:

Method A: Analytical HPLC column: RP-18 column Chromolith Speed ROD from Merck KgaA (Germany). Elution: acetonitrile+0.1% trifluoroacetic acid (TFA)/water+0.1% trifluoroacetic acid (TFA) in a ratio of from 5:95 to 95:5 in 5 minutes at 40° C.

Method B: Analytical UPLC column: Phenomenex Kinetex 1.7 µm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

MS-method: ESI positive.

$^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: h for hour(s), min for minute(s) and room temperature for 20-25° C.

A. Synthesis Examples

3-Chloro-4-hydroxy-5-methoxy-benzaldehyde

To a solution of 50.0 g (330 mmol) of vanillin in 250 mL of glacial acetic acid was added chlorine gas through a glass tubing over 60 minutes (with a slow gas flow) at 25° C. White solid product was collected by filtration, washed with 300 mL of hexane, and dried in vacuum to give the title compound (36.0 g; 58%).

Characterization by $^1$H-NMR (400 MHz, CDCl$_3$): δ[delta]=9.51 (s, 1H), 7.52 (s, 1H), 7.36 (s, 1H), 4.01 (s, 3H).

3-Chloro-4,5-dihydroxy-benzaldehyde

To a suspension of 3-chloro-4-hydroxy-5-methoxy-benzaldehyde (36.0 g, 193 mmol) in dichloromethane (1000 mL) was added BBr$_3$ (97.0 g, 387 mmol) dropwise at −40° C. under N$_2$. After addition, the mixture was stirred at this temperature for 5 h and then was poured into ice water. The precipitated solid was filtered and washed with petroleum ether. The solid was dried under reduced pressure to afford the title compound (30.0 g; 91%), which was directly used in the next step.

Characterization by $^1$H-NMR (400 MHz, DMSO): δ[delta]=10.41 (s, 1H), 9.70 (s, 1H), 7.44 (s, 1H), 7.23 (s, 1H).

7-Chloro-1,3-benzodioxole-5-carbaldehyde

To a solution of 3-chloro-4,5-dihydroxy-benzaldehyde (8.0 g, 46 mmol) and BrClCH$_2$ (89 g, 0.70 mol) in dry DMF (300 mL) was added Cs$_2$CO$_3$ (228 g, 0.700 mol). The mixture was stirred at 60° C. overnight and was then poured into water. The resulting mixture was extracted with ethyl acetate. The combined extracts were washed with brine, dried over Na$_2$SO$_4$ and concentrated under reduced pressure to afford the title compound (35.0 g; 100%).

Characterization by $^1$H-NMR (400 MHz, CDCl$_3$): δ[delta]=9.80 (s, 1H), 7.44 (s, 1H), 7.27 (s, 1H), 6.19 (s, 2H).

(7-Chloro-1,3-benzodioxol-5-yl)methanol

To a solution of 7-chloro-1,3-benzodioxole-5-carbaldehyde (35.0 g, 0.19 mol) in THF (300 mL) was added NaBH$_4$ (14.5 g, 0.38 mol) in portions at 0° C. The mixture was stirred at this temperature for 30 min and then poured into aqueous NH$_4$Cl solution. The organic layer was separated, and the aqueous phase was extracted with EtOAc (3×150 mL). The combined extracts were dried over Na$_2$SO$_4$ and evaporated under reduced pressure to afford the title compound (34.5 g; 98%), which was directly used in the next step.

4-Chloro-6-(chloromethyl)-1,3-benzodioxole

A mixture of (7-chloro-1,3-benzodioxol-5-yl)methanol (34.5 g, 0.185 mol) and SOCl$_2$ (5.0 mL, 67 mmol) in dichloromethane (200 mL) was stirred at room temperature for 1 h and was then poured into ice water. The organic layer was separated and the aqueous phase was extracted with dichloromethane (3×150 mL). The combined extracts were washed with water and aqueous NaHCO$_3$ solution, dried over Na$_2$SO$_4$ and evaporated under reduced pressure to afford the title compound (30.0 g; 80%), which was directly used in the next step.

Characterization by $^1$H-NMR (400 MHz, CDCl$_3$): δ[delta]=7.25 (s, 1H), 6.87 (s, 1H), 6.77 (s, 1H), 6.05 (s, 2H), 4.47 (s, 2H).

2-(7-Chloro-1,3-benzodioxol-5-yl)acetonitrile

A mixture of 4-chloro-6-(chloromethyl)-1,3-benzodioxole (30.0 g, 0.147 mol) and NaCN (7.94 g, 0.162 mol) in DMSO (80 mL) was stirred at 40° C. for 1 h and was then poured into water. The mixture was extracted with EtOAc (3×130 mL). The combined organic layers were washed with water and brine, dried over Na$_2$SO$_4$ and evaporated under reduced pressure to afford the title compound (14.2 g; 50%).

Characterization by $^1$H-NMR (400 MHz, CDCl$_3$): [delta]=6.83 (s, 1H), 6.73 (s, 1H), 6.06 (s, 2H), 3.66 (s, 2H).

2-(7-Chloro-1,3-benzodioxol-5-yl)-4,4,4-trifluoro-3-oxo-butanenitrile

Under reflux, 1.7 g of sodium (72.8 mmol) was dissolved in 50 ml of ethanol. At 50° C., a solution of 14.2 g (72.8 mmol) of 2-(7-chloro-1,3-benzodioxol-5-yl)acetonitrile and 10.3 g (72.8 mmol) of ethyl trifluoroacetate in 50 ml of ethanol was added dropwise, and the reaction mixture was then stirred under reflux for 12 hours. After cooling, the reaction mixture was concentrated on a rotary evaporator, dissolved in ethyl acetate and washed twice with 100 ml of 1N hydrochloric acid and once with water. The organic phase was separated off, dried over sodium sulphate, filtered and concentrated to give the title compound (23.9 g; 100%) and used for the next step directly.

3-Chloro-2-(7-chloro-1,3-benzodioxol-5-yl)-4,4,4-trifluoro-but-2-enenitrile 2-(7-chloro-1,3-benzodioxol-5-yl)-4,4,4-trifluoro-3-oxo-butanenitrile (23.9 g, 82 mmol) was treated with $POCl_3$ (62.0 g, 0.41 mol) and then triethylamine (11.4 mL, 82 mmol) was added. The reaction mixture was heated for 3 h at 80-100° C. and then carefully poured into warm water. The product was then extracted ethyl acetate, washed with water and brine, dried, filtered and concentrated to give the title compound (20.2 g; 80%) and used for the next step directly.

4-(7-Chloro-1,3-benzodioxol-5-yl)-2-pyrimidin-2-yl-5-(trifluoromethyl)pyrazol-3-amine 3-chloro-2-(7-chloro-1,3-benzodioxol-5-yl)-4,4,4-trifluoro-but-2-enenitrile (20.2 g, 65.4 mmol) was dissolved in ethanol (200 mL) and treated with pyrimidin-2-yl-hydrazine (7.20 g, 65.4 mmol) and triethylamine (6.60 g, 65.4 mmol). The reaction mixture was heated to reflux for 10 h. The solvent was removed in vacuo, to the residue was added water, extracted with EtOAc, then the organic layer was combined, washed with water and brine, dried, filtered and concentrated to give crude product. The crude product was washed with DCM to give the title compound (11.0 g; 44%).

Characterization by $^1$H-NMR (400 MHz, DMSO): δ[delta]=8.94 (d, 2H, J=4.8 Hz), 7.55 (m, 1H), 6.99 (s, 2H), 6.86 (s, 2H), 6.20 (s, 2H).

MS (M+H$^+$): 384

Preparation of Diethyl Sulfoxide

To a solution of $H_3BO_3$ (0.31 g, 5 mmol) in $H_2O_2$ (6.8 g, 60 mmol) was added dropwise diethyl sulfide (4.5 g, 50 mmol) at room temperature. The solution was stirred for 20 min at this temperature. The solution was extracted with DCM, organic layers were combined, washed with brine, dried, filtered and concentrated to give the desired title compound (3.0 g; 57%).

Characterization by $^1$H-NMR (400 MHz, CDCl$_3$): δ[delta]=2.66-2.73 (m, 4H), 1.33 (t, 6H, J=2.8 Hz).

Example S.1

[4-(7-Chloro-1,3-benzodioxol-5-yl)-2-pyrimidin-2-yl-5-(trifluoromethyl)pyrazol-3-yl]imino-diethyl-$\lambda^4$-sulfane (Compound I.1-1)

To a solution of diethyl sulfoxide (0.47 g, 4.4 mmo) in dichloromethane at −60° C. under argon was added drop-wise trifluoroacetic anhydride (0.93 g, 4.4 mmol). The solution was stirred for 20 min at this temperature. Then the 4-(7-chloro-1,3-benzodioxol-5-yl)-2-pyrimidin-2-yl-5-(trifluoromethyl)pyrazol-3-amine (0.76 g, 2 mmol) was added and the solution stirred at −60 C for 1 h. The reaction was diluted with aqueous ammonia; the organic layer was separated and further washed with water and then dried and concentrated. The residue was re-crystallized with a mixture of ethyl acetate and petrole ether to give the title compound (270 mg; 29%).

Characterization by $^1$H-NMR (400 MHz, CDCl$_3$): δ[delta]=8.84 (d, 2H, J=4.8 Hz), 7.28 (s, 1H), 6.96 (s, 1H), 6.83 (s, 1H), 6.08 (s, 2H), 2.62-2.65 (m, 4H), 1.12 (t, 6H, J=14.8 Hz).

MS (M+H$^+$): 471.9

Preparation of Diisopropyl Sulfoxide

To a stirred mixture of diisopropyl sulfide (3.54 g, 30 mmol), $Ac_2O$ (3.4 g, 33 mmol) and silica gel (6 g) in DCM (150 ml) was added dropwise $H_2O_2$ (30%). After addition, the mixture was stirred at this temperature for 3 h. The precipitated solid was filtered and the filtrate was washed with saturated aqueous $NaSHO_3$, $NaHCO_3$ and brine. The organic layers was separated, dried and concentrated to afford the title compound (3.0 g; 75%).

Characterization by $^1$H-NMR (400 MHz, CDCl$_3$): δ[delta]=2.71-2.78 (m, 2H), 1.25 (dd, 12H, J=23.2 Hz).

Example S.2

[4-(7-Chloro-1,3-benzodioxol-5-yl)-2-pyrimidin-2-yl-5-(trifluoromethyl)pyrazol-3-yl]imino-diisopropyl-$\lambda^4$-sulfane (Compound I.1-2)

To a solution of diisopropyl sulfoxide (0.75 g, 5.6 mmo) in dichloromethane at −60° C. under argon was added dropwise trifluoroacetic anhydride (1.18 g, 5.6 mmol). The solution was stirred for 20 min at this temperature. Then the 4-(7-chloro-1,3-benzodioxol-5-yl)-2-pyrimidin-2-yl-5-(trifluoromethyl)pyrazol-3-amine (0.97 g, 2.5 mmol) was added and the solution stirred at −60° C. for 1 h. The reaction was diluted with aqueous ammonia; the organic layer separated and further washed with water and then dried and concentrated. The residue was re-crystallized with a mixture of ethyl acetate and petrole ether to give the title compound (80 mg; 8%).

Characterization by $^1$H-NMR (400 MHz, CDCl$_3$): δ[delta]=8.86 (d, 2H, J=4.8 Hz), 7.28 (s, 1H), 6.91 (s, 1H), 6.79 (s, 1H), 6.11 (s, 2H), 2.91 (s, 2H), 1.17 (t, 6H, J=14.8 Hz).

MS (M+H$^+$): 500

Example S.3

2-[4-(7-Chloro-1,3-benzodioxol-5-yl)-5-(thiolan-1-ylideneamino)-3-(trifluoromethyl)pyrazol-1-yl]pyrimidine (Compound I.1-3)

To a solution of 2.2 equivalents of tetrahydro-thiophene 1-oxide (0.23 g, 2.2 mmo) in dichloromethane at −60° C. under argon was added dropwise trifluoroacetic anhydride (0.46 g, 2.2 mmol). The solution was stirred for 20 min at this temperature. Then the 4-(7-chloro-1,3-benzodioxol-5-yl)-2-pyrimidin-2-yl-5-(trifluoromethyl)pyrazol-3-amine (0.383 g, 1.00 mmol) was added and the solution stirred at −60° C. for 1 h. The reaction was diluted with aqueous ammonia; the organic layer separated and further washed with water and then dried and concentrated.

The residue was re-crystallized with a mixture of ethyl acetate and petrole ether to give the title compound (190 mg; 41%).

Characterization by $^1$H-NMR (400 MHz, CDCl$_3$): δ[delta]=8.76 (d, 2H, J=4.8 Hz), 7.19 (s, 1H), 6.91 (s, 1H), 6.79 (s, 1H), 6.02 (s, 2H), 2.88-2.94 (m, 2H), 2.68-2.75 (m, 2H), 2.25-2.29 (m, 2H), 1.75-1.81 (m, 2H).

MS (M+H$^+$): 470

By the methods described above, in examples S.1 to S.3, the compounds I.1-4 to I-1-6 as described in the following table have been prepared in an analogous manner:

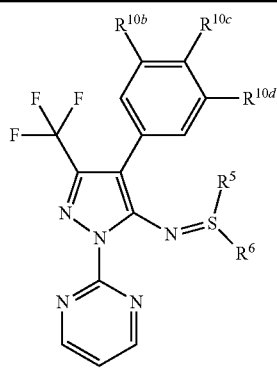

| Comp. | R$^5$ | R$^6$ | R$^{10b}$ | R$^{10c}$ | R$^{10d}$ | $^1$H-NMR (400 MHz, CDCl$_3$): δ[delta] |
|---|---|---|---|---|---|---|
| I.1-4 | CH$_2$CH$_3$ | CH$_2$CH$_3$ | CF$_3$ | H | Cl | 8.84 (d, 2H, 4.8 Hz), 7.68 (d, 2H, 5.2 Hz), 7.56 (s, 1H), 7.28-7.31 (m, 1H), 2.65-2.68 (m, 4H), 1.09 (t, 6H, 14.8 Hz). |
| I.1-5 | CH(CH$_3$)$_2$ | CH(CH$_3$)$_2$ | CF$_3$ | H | Cl | 8.84 (d, 2H, 4.8 Hz), 7.56-7.62 (m, 2H), 7.27-7.30 (m, 1H), 2.82-2.90 (m, 2H), 1.10-1.13 (m, 12H). |
| I.1-6 | —CH$_2$CH$_2$CH$_2$CH$_2$— | | CF$_3$ | H | Cl | 8.86 (d, 2H, 4.8 Hz), 7.73 (d, 2H, 14 Hz), 7.56 (s, 1H), 7.31-7.34 (m, 1H), 3.00-3.07 (m, 2H), 2.83-2.88 (m, 2H), 2.38-2.43 (m, 2H), 1.89-1.93 (m, 2H). |

Example S.7

2-[4-[3-chloro-5-(trifluoromethyl)phenyl]-5-pyrrol-1-yl-3-(trifluoromethyl)pyrazol-1-yl]pyrimidine (Compound I.1-7)

A mixture of 4-(7-chloro-1,3-benzodioxol-5-yl)-2-pyrimidin-2-yl-5-(trifluoromethyl)pyrazol-3-amine (0.383 g, 1.00 mmol) and 2,5-dimethoxytetrahydrofuran (0.145 g, 1.10 mmol) in acetic acid was stirred under reflux for 1 hour. After cooling, the precipitate was filtered off and recrystallized from ethanol to give the title compound (0.262 g, 57%).

Characterization by $^1$H-NMR (400 MHz, CDCl$_3$): δ[delta]=8.82 (d, 2H, J=4.8 Hz), 7.61 (s, 1H), 7.40 (m, 2H), 7.30 (m, 1H), 6.67 (s, 2H), 6.28 (s, 2H).

MS (M+H$^+$): 458

Example S.8

4-[3-chloro-5-(trifluoromethyl)phenyl]-N-diethoxy-phosphoryl-2-pyrimidin-2-yl-5-(trifluoromethyl) pyrazol-3-amine (Compound I.1-8)

To a mixture of 4-(7-chloro-1,3-benzodioxol-5-yl)-2-pyrimidin-2-yl-5-(trifluoromethyl)pyrazol-3-amine (0.766 g, 2.00 mmol) and NaH (0.054 g, 2.20 mmol) in tetrahydrofuran at 0° C. is added diethyl chlorophosphate (0.414 g, 2.40 mmol). The mixture is allowed to reach room temperature (20-25° C.) and further stirred for 12 hours. The reaction was diluted with water and extracted with ethyl acetate; the organic layer separated and further washed with water and then dried and concentrated. The residue was re-crystallized with a mixture of ethyl acetate and petrole ether to give the title compound (125 mg; 12%).

Characterization by $^1$H-NMR (400 MHz, CDCl$_3$): δ[delta]=9.21 (m, 1H), 8.91 (m, 1H), 7.67 (s, 1H), 7.62 (s, 1H), 7.58 (s, 1H), 7.40 (m, 1H), 3.70 (m, 4H), 1.0 (m, 6H).

MS (M+H$^+$): 544

Example S.9

1-[4-[3-chloro-5-(trifluoromethyl)phenyl]-2-pyrimidin-2-yl-5-(trifluoromethyl)pyrazol-3-yl]-3-ethyl-1-(ethylcarbamoyl)urea (Compound I.1-9)

To a mixture of 4-(7-chloro-1,3-benzodioxol-5-yl)-2-pyrimidin-2-yl-5-(trifluoromethyl)pyrazol-3-amine (0.200 g, 0.50 mmol) and NaH (0.015 g, 0.64 mmol) in tetrahydrofurane is added ethylisocyanate (0.078 g, 1.10 mmol). The mixture is refluxed for 4 hours. The reaction was cooled to room temperature (20-25° C.), diluted with water and extracted with ethyl acetate; the organic layer separated and further washed with water and then dried and concentrated. The residue was re-crystallized with a mixture of ethyl acetate and petrole ether to give the title compound (46 mg; 16%).

Characterization by $^1$H-NMR (400 MHz, CDCl$_3$): δ[delta]=8.65 (m, 2H), 7.60 (s, 1H), 7.55 (s, 1H), 7.12 (m, 1H), 7.00 (m, 1H), 4.09 (m, 2H), 3.45 (m, 2H), 1.30 (m, 3H), 1.05 (m, 3H).

MS (M+H$^+$): 550

Example S.10

N-[(E)-[4-[3-chloro-5-(trifluoromethyl)phenyl]-2-pyrimidin-2-yl-5-(trifluoromethyl)pyrazol-3-yl]azo] aniline (Compound I.1-10)

To a stirred suspension of 4-(7-chloro-1,3-benzodioxol-5-yl)-2-pyrimidin-2-yl-5-(trifluoromethyl)pyrazol-3-amine (0.6 g, 1.47 mmol) in water at 0° C. is added a solution of tetrafluoroboric acid (0.18 g, 2.00 mmol) in water followed by slow addition of a solution of sodium nitrite (0.13, 1.80 mmol) in water. The reaction mixture was allowed to reach room temperature (20-25° C.) and stirred for 2 hours. The precipitate was filtered and suspended in ethanol at 0° C. A solution of aniline (0.15 g, 1.60 mmol) and sodium acetate (0.20 g, 2.50 mmol) in EtOH was added dropwise and the mixture was allowed to stir at room temperature (20-25° C.) for 2 hours. The reaction mixture was concentrated, then the mixture was dissolved in ethyl acetate and washed with water. The organic phase was dried and the residue re-crystallized with a mixture of ethyl acetate and petrol ether to give the title compound (165 mg; 22%).

Characterization by ¹H-NMR (400 MHz, CDCl₃): δ[delta]=8.95 (m, 2H), 7.65 (m, 3H), 7.45 (m, 1H), 7.20 (m, 4H), 6.90 (m, 2H).

MS (M+H⁺): 512

B. Biological Examples

The activity of the compounds of formula I of the present invention could be demonstrated and evaluated in biological tests described in the following.

If not otherwise specified the test solutions are prepared as follow:

The active compound is dissolved at the desired concentration in a mixture of 1:1 (vol:vol) distilled water:acetone. The test solution is prepared at the day of use and in general at concentrations of ppm (wt/vol).

B.1 Cowpea Aphid (*aphis craccivora*)

Potted cowpea plants colonized with approximately 100-150 aphids of various stages were sprayed after the pest population has been recorded. Population reduction was assessed after 24, 72, and 120 hours.

In this test, the compounds I.1-1, I.1-2, I.1-3, I.1-4, I.1-5, I.1-6, I.1-7 and I.1-10 respectively, at 300 ppm showed a mortality of at least 75% in comparison with untreated controls.

B.2 Diamond Back Moth (*plutella xylostella*)

The active compound is dissolved at the desired concentration in a mixture of 1:1 (vol/vol) distilled water:acetone. Surfactant (Alkamuls® EL 620) is added at a rate of 0.1% (vol/vol). The test solution is prepared at the day of use.

Leaves of cabbage were dipped in test solution and air-dried. Treated leaves were placed in petri dishes lined with moist filter paper and inoculated with ten 3rd instar larvae. Mortality was recorded 72 hours after treatment. Feeding damages were also recorded using a scale of 0-100%.

In this test, the compounds I.1-1, I.1-2, I.1-3, I.1-4, I.1-5, I.1-6, I.1-7, I.1-8, and I.1-10 respectively, at 300 ppm showed a mortality of at least 75% in comparison with untreated controls.

B.3 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, the compounds I.1-1, I.1-2, I.1-3, I.1-4, I.1-5, I.1-6, I.1-8 and I.1-10 respectively, at 2500 ppm showed a mortality of at least 75% in comparison with untreated controls.

B.4 Orchid Thrips (*dichromothrips corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant.

Thrips potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult thrips. The petri dishes are then covered with lids. All test arenas are held under continuous light and a temperature of about 28° C. for duration of the assay. After 4 days, the numbers of live thrips are counted on each flower, and along inner walls of each petri dish. The level of thrips mortality is extrapolated from pre-treatment thrips numbers.

In this test, the compounds I.1-1, I.1-2, I.1-3, I.1-4, I.1-5, I.1-6, I.1-7 and I.1-8 respectively, at 300 ppm showed a mortality of at least 75% in comparison with untreated controls.

B.5 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants. In this test, the compounds I.1-1, I.1-2, I.1-3, I.1-5 and I.1-7 respectively, at 500 ppm showed a mortality of at least 75% in comparison with untreated controls.

B.6 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the 1ˢᵗ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds I.1-1, I.1-2, I.1-3, I.1-4, I.1-5, I.1-6, I.1-7 and I.1-10 respectively, at 300 ppm showed a mortality of at least 75% in comparison with untreated controls.

B.7 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds I.1-1, I.1-2, I.1-3, I.1-4, I.1-5, I.1-6 and I.1-10 respectively, at 2500 ppm showed a mortality of at least 75% in comparison with untreated controls.

B.8 Tobacco Budworm (*Heliothis virescens*) I

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds I.1-1, I.1-2, I.1-3, I.1-4, I.1-5, I.1-6, I.1-7, and I.1-10 respectively, at 2500 ppm showed a mortality of at least 75% in comparison with untreated controls.

B.9 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, the compounds I.1-1, I.1-2, I.1-3, I.1-4, I.1-5, I.1-6 and I.1-10 respectively, at 2500 ppm showed a mortality of at least 75% in comparison with untreated controls.

B.10 Green Peach Aphid (*Myzus persicae*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, the compound I.1-5 and I.1-10 at 300 ppm showed a mortality of at least 75% in comparison with untreated controls.

B.11 Red Spider Mite (*Tetranychus kanzawai*)

The active compound is dissolved at the desired concentration in a mixture of 1:1 (vol:vol) distilled water:acetone. Add surfactant (Alkamuls® EL 620) at the rate of 0.1% (vol/vol). The test solution is prepared at the day of use.

Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassava leaf section with known mite population. Treated plants were placed inside a holding room at about 25-27° C. and about 50-60% relative humidity.

Percent mortality was assessed 72 hours after treatment.

In this test, the compounds I.1-1, I.1-3, I.1-4, I.1-5 and I.1-6 respectively, at 300 ppm showed a mortality of at least 75% in comparison with untreated controls.

B.12 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds I.1-1, I.1-2, I.1-3, I.1-4, I.1-5, I.1-6 and I.1-7 respectively, at 300 ppm showed a mortality of at least 75% in comparison with untreated controls.

B13. Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds I.1-1, I.1-2, I.1-3, I.1-4, I.1-5, I.1-6 and I.1-9 respectively, at 500 ppm showed a mortality of at least 75% in comparison with untreated controls.

B.14 Colorado Potato Beetle (*Leptinotarsa decemlineata*)

The active compounds are formulated in cyclohexanone as a 10,000 ppm solution supplied in tubes. The tubes are inserted into an automated electrostatic sprayer equipped with an atomizing nozzle and they serve as stock solutions for which lower dilutions were made in 50% acetone:50% water (v/v). A nonionic surfactant (Kinetic®) is included in the solution at a volume of 0.01% (v/v).

Eggplants are grown 2 plants to a pot and are selected for treatment at the 1st true leaf stage. Test solutions are sprayed onto the foliage by an automated electrostatic plant sprayer equipped with an atomizing spray nozzle. The plants are dried in the sprayer fume hood and then removed from the sprayer. The treated foliage is then cut and removed from the pot and placed in a Petri dish lined with moistened filter pa-per. Five beetle larvae are introduced into each Petri dish and the dish is covered by a Petri dish lid. Petri dishes are maintained in a growth room at about 25° C. and about 20-40% relative humidity for 4 days, avoiding direct exposure to fluorescent light (24 hour photoperiod) to prevent trapping of heat inside the dishes. Mortality and reduced feeding are assessed 4 days after treatment, compared to untreated control plants.

In this test, the compound I.1-5, at 300 ppm, showed a mortality of at least 75% in comparison with untreated controls.

We claim:
1. A compound of formula (I)

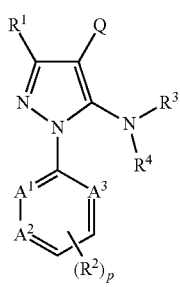

(I)

wherein
$A^1$ is N,
$A^2$ is $C-R^2$,
$A^3$ is N,
Q is selected from phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
$R^1$ is selected from the group consisting of halogen; cyano; azido; nitro; —SCN; $SF_5$; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$; —Si$(R^{14})_2R^{13}$; —$OR^8$; —OS(O)$_n R^8$; —$SR^8$; —S(O)$_m R^8$; —S(O)$_n$N($R^{9a}$)$R^{9b}$; —N($R^{9a}$)$R^{9b}$; —N($R^{9a}$)C(=O)$R^7$; C(=O)$R^7$; —C(=O)$OR^8$; —C(=N$R^{9a}$)H; —C(=N$R^{9a}$)$R^7$; —C(=O)N($R^{9a}$)$R^{9b}$; C(=S)N($R^{9a}$)$R^{9b}$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
$R^2$ is selected from the group consisting of hydrogen, halogen, cyano, azido, nitro, —SCN, $SF_5$, $C_1$-$C_6$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —Si$(R^{14})_2R^{13}$, —$OR^8$, OS(O)$_n R^8$, —$SR^8$, —S(O)$_m R^8$, —S(O)$_n$N($R^{9a}$)$R^{9b}$, —N($R^{9a}$)$R^{9b}$, N($R^{9a}$)C(=O)$R^7$, —C(=O)$R^7$, —C(=O)$OR^8$, —C(=S)$R^7$, —C(=S)$OR^8$, —C(=N$R^{9a}$)$R^7$, —C(=O)N($R^{9a}$)$R^{9n}$, —C(=S)N($R^{9a}$)$R^{9b}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
$R^3$ is selected from the group consisting of nitro, —N$R^{9a}R^{9b}$; —S(O)$_n$N($R^{9a}$)$R^{9b}$; —C(=O)N($R^{9a}$)$R^{9b}$; —C(=S)N($R^{9a}$)$R^{9b}$; —C(=N$R^{9a}$)—S(O)$_m R^8$, —P(O)$G_2$, —PG$_3$, —N=N—$R^{9a}$;
$R^4$ is selected from the group consisting of hydrogen, cyano, $C_1$-$C_6$-alkyl which may be partially or fully halogenated and/or may be substituted by one or more radicals $R^7$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^7$, $C_3$-$C_8$-cycloalkyl which may be partially or fully halogenated and/or may be substituted by one or more radicals $R^7$, $C_3$-$C_8$-cycloalkyl-$C_1$-$C_4$-alkyl where the cycloalkyl moiety may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —N($R^{9a}$)$R^{9b}$; —N($R^{9a}$)C(=O)$R^7$; —Si$(R^{14})_2R^{13}$; —$OR^8$; —$SR^8$; —S(O)$_m R^8$; —S(O)$_n$N($R^{9a}$)$R^{9b}$; —C(=O)$R^7$; —C(=O)$OR^8$; —C(=O)N($R^{9a}$)$R^{9b}$; —C(=S)$R^7$; —C(=S)$OR^8$; —C(=S)N($R^{9a}$)$R^{9b}$; C(=N$R^{9a}$)—S(O)$_m R^8$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
or $R^3$ and $R^4$ form together with the nitrogen they are bound to a group of the formula A.1

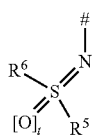

(A.1)

or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

provided that $R^3$ and $R^4$ do not form together with the nitrogen atom they are bound a substituted or unsubstituted piperidine, pyrrolidine or morpholine;

G is selected independently from each other and independently of each occurrence from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylamino, $C_1$-$C_6$-dialkylamino, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

$R^5$ and $R^6$ each independently are $C_1$-$C_{12}$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_{12}$-alkenyl which may be partially or fully halogenated and/or may be substituted by one or more radicals $R^7$, $C_2$-$C_{12}$-alkynyl which may be partially or fully halogenated and/or may be substituted by one or more radicals $R^7$, —C(=O)$R^7$, —C(=NO$R^8$)$R^7$, —C(=NN($R^{9a}$)$R^{9b}$)$R^7$, —C(=O)O$R^7$, —C(=O)N($R^{9a}$)$R^{9B}$, —OC(=O)$R^7$, —OC(=O)O$R^8$, —N$R^{9a}$C(=O)$R^7$, —N[C(=O)$R^7$]$_2$, —N$R^7$C(=O)O$R^8$, —C(=O)N($R^{9a}$)—N($R^{9b}$)$_2$, —C(=O)N$R^{9a}$—N$R^{9b}$[C(=O)$R^7$], —N$R^{9a}$—C(=O)N($R^{9b}$)$_2$, —N$R^{9a}$—N$R^{9b}$C(=O)$R^7$, —N$R^{9a}$—N[C(=O)$R^7$]$_2$, —N[(C=O)$R^7$]—N($R^{9a}$)$_2$, —N$R^{9a}$N$R^{9b}$[(C=O)$R^8$], —N$R^{9a}$[(C=O)N($R^{9b}$)$_2$], —N$R^{9a}$[C=N$R^{9b}$]$R^7$, —N$R^{9a}$(C=N$R^{9b}$)N($R^{9b}$)$_2$, —O—N($R^{9a}$)$_2$, —O—N$R^{9a}$(C=O)$R^7$, —SO$_2$N$R^{9a}$$R^{9b}$, —N$R^{9a}$SO$_2$$R^8$, —SO$_2$O$R^8$, —OSO$_2$$R^8$, —O$R^8$, —N$R^{9a}$$R^{9b}$, —S$R^8$, —Si($R^{14}$)$_2$$R^{13}$, —P$R^{9a}$$R^{9b}$, —SO$R^8$, —SO$_2$$R^8$, or —P(=O)$_t$G$_2$, —P(=O)$_2$G$_2$;

or $R^5$ and $R^6$ together with the sulfur atom to which they are attached form a saturated, partially unsaturated or unsaturated 3- to 8-membered ring which optionally contains 1 to 4 further heteroatoms selected from the group consisting of oxygen, nitrogen, and sulfur, which ring can be fused with one or two saturated, partially unsaturated or unsaturated 5- to 6-membered rings which may contain 1 to 4 heteroatoms selected from the group consisting of oxygen, nitrogen, and sulfur, wherein all of the above rings are unsubstituted or substituted by any combination of 1 to 6 groups $R^{18}$;

each $R^7$ is independently selected from the group consisting of cyano, azido, nitro, —SCN, SF$_5$, $C_1$-$C_4$-alkyl, $C_3$-$C_8$-cycloalkyl, $C_3$-$C_8$-halocycloalkyl, —Si($R^{14}$)$_2$$R^{13}$, —O$R^8$, —OSO$_2$$R^8$, —S$R^8$, —S(O)$_m$$R^8$, —S(O)$_n$N($R^{9a}$)$R^{9b}$, —N($R^{9a}$)$R^{9b}$, —C(=O)N($R^{9a}$)$R^{9b}$, —C(=S)N($R^{9a}$)$R^{9b}$, —C(=O)O$R^8$, —C(=O)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

and, in case $R^7$ is bound to a cycloalkyl group or to a heterocyclic ring, $R^7$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$; and in groups —C(=O)$R^7$, —C(=S)$R^7$, —C(=N$R^{9a}$)$R^7$ and —N($R^{9a}$)C(=O)$R^7$, $R^7$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^7$ together form a group selected from the group consisting of =C$R^{11}$$R^{12}$, =S(O)$_m$$R^8$, =S(O)$_m$N($R^{9a}$)$R^{9b}$, =N$R^{9a}$, =NO$R^8$ and =NN$R^{9a}$$R^{9b}$;

or two radicals $R^7$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^8$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2$$R^{13}$, —S$R^{20}$, —S(O)$_m$$R^{20}$, —S(O)$_n$N($R^{9a}$)$R^{9b}$, —N($R^{9a}$)$R^{9b}$, —N=C$R^{15}$$R^{16}$, —C(=O)$R^{17}$, —C(=O)N($R^{9a}$)$R^{9b}$, —C(=S)N($R^{9a}$)$R^{9b}$, —C(=O)O$R^{20}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^8$ is not $C_1$-$C_6$-alkoxy or $C_1$-$C_6$-haloalkoxy if it is bound to an oxygen atom;

$R^{9a}$, $R^{9b}$ are, independently of each other and independently of each occurrence, selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —N($R^{21}$)$R^{22}$; —N($R^{21}$)C(=O)$R^{19}$; —Si($R^{14}$)$_2R^{13}$; —O$R^{20}$; —S$R^{20}$; —S(O)$_mR^{20}$, —S(O)$_n$N($R^{21}$)$R^{22}$; —C(=O)$R^{19}$; —C(=O)O$R^{20}$; —C(=O)N($R^{21}$)$R^{22}$; —C(=S)$R^{17}$; C(=S)O$R^{20}$, —C(=S)N($R^{21}$)$R^{22}$; —C(=N$R^{21}$)$R^{17}$—S(O)$_mR^{20}$, —S(O)$_n$N($R^{21}$)$R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or $R^{9a}$ and $R^{9b}$ together form a group =C$R^{11}R^{12}$;

or $R^{9a}$ and $R^{9b}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals $R^{10}$;

each $R^{10}$ is independently selected from the group consisting of halogen, cyano, azido, nitro, —SCN, SF$_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —Si($R^{14}$)$_2R^{13}$, —O$R^{20}$, —OS(O)$_nR^{20}$, —S$R^{20}$, —S(O)$_mR^{20}$, —S(O)$_n$N($R^{21}$)$R^{22}$, —N($R^{21}$)$R^{22}$, C(=O)$R^{19}$, —C(=O)O$R^{20}$, —C(=N$R^{21}$)$R^{22}$; —C(=S)N($R^{21}$)$R^{22}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from the group consisting of N, O, S, NO, SO and SO$_2$, as ring members, which may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$N$R^{21}$—, —CH$_2$CH=N—, —CH=CH—N$R^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more CH$_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —C(=O)$R^{19}$, —C(=O)O$R^{20}$, —C(=N$R^{21}$)$R^{22}$, —C(=O)N($R^{21}$)$R^{22}$, —C(=S)N($R^{21}$)$R^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^2$;

each $R^{19}$ is independently selected from the group consisting of cyano, azido, nitro, —SCN, SF$_5$, $C_3$-$C_8$-cycloalkyl, $C_3$-$C_8$-halocycloalkyl, —Si($R^{14}$)$_2R^{13}$, —O$R^{20}$, —OSO$_2R^{20}$, —S$R^{20}$, —S(O)$_mR^{20}$, —S(O)$_n$N($R^{21}$)$R^{22}$, —N($R^{21}$)$R^{22}$, —C(=O)N($R^{21}$)$R^{22}$, —C(=S)N($R^{21}$)$R^{22}$, —C(=O)O$R^{20}$, —C(=O)$R^{20}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl;

and in groups —C(=O)$R^{19}$, $R^{19}$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from the group consisting of =C$R^{11}R^{12}$, =S(O)$_m R^{20}$, =S(O)$_m$N($R^{21}$)$R^{22}$, =N$R^{21}$, =NO$R^{20}$ and =NN$R^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and SO$_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals selected from the group consisting of halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3, 4 or 5;
t is 0 or 1;
or a stereoisomer, N-oxide, tautomer or agriculturally or veterinarily acceptable salt thereof.

2. The compound of claim 1, wherein
Q is phenyl which may be substituted by 1, 2, 3, 4 or 5 radicals $R^{10}$.

3. The compound of claim 1, wherein
the compounds have the general formula (I-I)

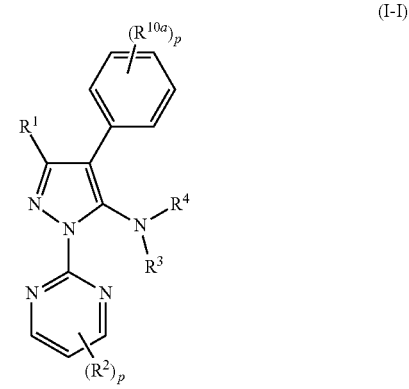

(I-I)

wherein
$R^1$ is selected from the group consisting of halogen; cyano; azido; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$;
each $R^{10a}$ is independently selected from the group as defined for $R^{10}$ in any of the preceding claims;
p is independently from each occurrence 0, 1, 2 or 3.

4. The compound of claim 1, wherein
$R^1$ is selected from the group consisting of halogen; $C_1$-$C_6$-alkyl which may be partially or fully halogenated; $C_3$-$C_8$-cycloalkyl which may be partially or fully halogenated; $C_2$-$C_6$-alkenyl which may be partially or fully halogenated; $C_2$-$C_6$-alkynyl which may be partially or fully halogenated;

$R^2$ is selected from the group consisting of hydrogen, halogen, cyano, azido; $C_1$-$C_6$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$.

5. The compound of claim 1, wherein
$R^1$ is $C_1$-$C_6$-alkyl which may be partially or fully halogenated;
$R^2$ is selected from the group consisting of hydrogen, halogen, $C_1$-$C_6$-alkyl which may be partially or fully halogenated; $C_3$-$C_8$-cycloalkyl which may be partially or fully halogenated.

6. The compound of claim 5, wherein
$R^1$ is methyl, trifluoromethyl, difluoromethyl or fluoromethyl;
$R^2$ is selected from the group consisting of hydrogen, halogen, $C_1$-$C_6$-alkyl.

7. The compound of claim 1, wherein
each $R^{10}$ and $R^{10a}$ is independently selected from the group consisting of halogen, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$;
or two radicals $R^{10}$ and/or $R^{10a}$ bound on adjacent atoms together form a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —S($CH_2$)S—, —$CH_2CH_2NR^{21}$—, —$CH_2CH$=N—, —CH=CH—$NR^{21}$—, —OCH=N— and —SCH=N—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group.

8. The compound of claim 1, wherein
$R^3$ is selected from the group consisting of nitro, —$NR^{9a}R^{9b}$; —S(O)$_m$N($R^{9a}$)$R^{9b}$; —C(=O)N($R^{9a}$)$R^{9b}$; —C(=S)N($R^{9a}$)$R^{9b}$; —C(=$NR^{9a}$)—S(O)$_m$$R^8$, —P(O)$G_2$, —P$G_3$, —N=N—$R^{9a}$;
$R^4$ is selected from the group consisting of hydrogen, cyano, $C_1$-$C_6$-alkyl which may be partially or fully halogenated and/or may be substituted by one or more radicals $R^7$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^7$, $C_3$-$C_8$-cycloalkyl which may be partially or fully halogenated and/or may be substituted by one or more radicals $R^7$, $C_3$-$C_8$-cycloalkyl-$C_1$-$C_4$-alkyl where the cycloalkyl moiety may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —N($R^{9a}$)$R^{9b}$; —N($R^{9a}$)C(=O)$R^7$; —Si($R^{14}$)$_2$$R^{13}$; —$OR^8$; —$SR^8$; —S(O)$_m$$R^8$; —S(O)$_n$N($R^{9a}$)$R^{9b}$; —C(=O)$R^7$; —C(=O)$OR^8$; —C(=O)N($R^{9a}$)$R^{9b}$; —C(=S)$R^7$; —C(=S)$OR^8$; —C(=S)N($R^{9a}$)$R^{9b}$; —C(=$NR^{9a}$)—S(O)$_m$$R^8$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;
provided that $R^3$ and $R^4$ do not form together with the nitrogen atom they are bound a substituted or unsubstituted piperidine, pyrrolidine or morpholine.

9. The compound of claim 1, wherein
$R^3$ and $R^4$ form together with the nitrogen they are bound to a group of the formula A.1

(A.1)

in which $R^5$ and $R^6$ are as defined in any of the preceding claims 1 to 7.

10. The compound of claim 9, wherein
$R^5$ and $R^6$ each independently are $C_1$-$C_{12}$-alkyl which may be partially or fully halogenated and/or substituted by one or more $C_1$-$C_6$-alkoxy groups; or $C_3$-$C_8$-cycloalkyl which may be partially or fully halogenated.

11. An agricultural or veterinary composition comprising at least one compound as defined in claim 1 and at least one liquid and/or solid carrier.

12. A mixture or composition comprising at least one compound as defined in claim 1 and at least one further pesticide.

13. A method for combating or controlling invertebrate pests, which method comprises contacting said pest or its food supply, habitat or breeding grounds with a pesticidally effective amount of at least one compound as defined in claim 1.

14. A method for protecting growing plants from attack or infestation by invertebrate pests, which method comprises contacting a plant, or soil or water in which the plant is growing, with a pesticidally effective amount of at least one compound as defined in claim 1.

15. A method for the protection of seeds from soil insects and of the seedlings' roots and shoots from soil and foliar insects comprising contacting the seeds before sowing and/or after pregermination with at least one compound as defined in claim 1.

16. Seed treated with a compound as defined in claim 1 in an amount of from 0.1 g to 10 kg per 100 kg of the plant propagation material.

17. A method for treating a non-human animal infested or infected by parasites or for protecting a non-human animal against infestation or infection by parasites which comprises orally, topically or parenterally administering or applying to the non-human animal a parasiticidally effective amount of a compound as defined in claim 1.

18. The method of claim 14, wherein, in the compound of formula (I), Q is phenyl which may be substituted by 1, 2, 3, 4 or 5 radicals $R^{10}$.

19. The method of claim 14, wherein the compound of formula (I) has the general formula (I-I)

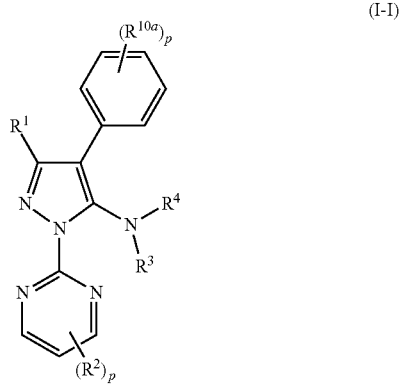

wherein
$R^1$ is selected from the group consisting of halogen; cyano; azido; $C_1$-$C_6$-alkyl which may be partially or fully halogenated and/or may be substituted by one or more radicals $R^7$; $C_3$-$C_8$-cycloalkyl which may be partially or fully halogenated and/or may be substituted by one or more radicals $R^7$; $C_2$-$C_6$-alkenyl which may be partially or fully halogenated and/or may be substituted by one or more radicals $R^7$; $C_2$-$C_6$-alkynyl which may be partially or fully halogenated and/or may be substituted by one or more radicals $R^7$;

each $R^{10a}$ is independently selected from the group as defined for $R^{10}$;

p is independently from each occurrence 0, 1, 2 or 3.

20. The method of claim 14, wherein, in the compound of formula (I),
$R^1$ is selected from the group consisting of halogen; $C_1$-$C_6$-alkyl which may be partially or fully halogenated; $C_3$-$C_8$-cycloalkyl which may be partially or fully halogenated; $C_2$-$C_6$-alkenyl which may be partially or fully halogenated; $C_2$-$C_6$-alkynyl which may be partially or fully halogenated;
$R^2$ is selected from the group consisting of hydrogen, halogen, cyano, azido; $C_1$-$C_6$-alkyl which may be partially or fully halogenated and/or may be substituted by one or more radicals $R^7$, $C_3$-$C_8$-cycloalkyl which may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$.

21. The method of claim 14, wherein, in the compound of formula (I),
$R^1$ is $C_1$-$C_6$-alkyl which may be partially or fully halogenated;
$R^2$ is selected from the group consisting of hydrogen, halogen, $C_1$-$C_6$-alkyl which may be partially or fully halogenated; $C_3$-$C_8$-cycloalkyl which may be partially or fully halogenated.

22. The method of claim 21, wherein, in the compound of formula (I),
$R^1$ is methyl, trifluoromethyl, difluoromethyl or fluoromethyl;
$R^2$ is selected from the group consisting of hydrogen, halogen, $C_1$-$C_6$-alkyl.

23. The method of claim 14, wherein, in the compound of formula (I),
each $R^{10}$ and $R^{10a}$ is independently selected from the group consisting of halogen, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$;
or two radicals $R^{10}$ and/or $R^{10a}$ bound on adjacent atoms together form a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^{21}$—, —CH$_2$CH=N—, —CH=CH—NR$^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more CH$_2$ groups of the above groups may be replaced by a C=O group.

24. The method of claim 14, wherein, in the compound of formula (I),
$R^3$ is selected from the group consisting of nitro, —NR$^{9a}$R$^{9b}$; —S(O)$_m$N(R$^{9a}$)R$^{9b}$; —C(=O)N(R$^{9a}$)R$^{9b}$; —C(=S)N(R$^{9a}$)R$^{9b}$; —C(=NR$^{9a}$)—S(O)$_m$R$^8$, —P(O)G$_2$, —PG$_3$, —N=N—R$^{9a}$;
$R^4$ is selected from the group consisting of hydrogen, cyano, $C_1$-$C_6$-alkyl which may be partially or fully halogenated and/or may be substituted by one or more radicals $R^7$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^7$, $C_3$-$C_8$-cycloalkyl which may be partially or fully halogenated and/or may be substituted by one or more radicals $R^7$, $C_3$-$C_8$-cycloalkyl-$C_1$-$C_4$-alkyl where the cycloalkyl moiety may be partially or fully halogenated and/or may be substituted by one or more radicals $R^7$, $C_2$-$C_6$-alkenyl which may be partially or fully halogenated and/or may be substituted by one or more radicals $R^7$, $C_2$-$C_6$-alkynyl which may be partially or fully halogenated and/or may be substituted by one or more radicals $R^7$, —N($R^{9a}$)$R^{9b}$; —N($R^{9a}$)C(=O)$R^7$; —Si($R^{14}$)$_2R^{13}$; —O$R^8$; —S$R^8$; —S(O)$_mR^8$; —S(O)$_n$N($R^{9a}$)$R^{9b}$; —C(=O)$R^7$; —C(=O)O$R^8$; —C(=O)N($R^{9a}$)$R^{9b}$; —C(=S)$R^7$; —C(=S)O$R^8$, —C(=S)N($R^{9a}$)$R^{9b}$; —C(=N$R^{9a}$)—S(O)$_mR^8$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^3$ and $R^4$ form together with the nitrogen atom they are bound a 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

provided that $R^3$ and $R^4$ do not form together with the nitrogen atom they are bound a substituted or unsubstituted piperidine, pyrrolidine or morpholine.

25. The method of claim 14, wherein, in the compound of formula (I),
$R^3$ and $R^4$ form together with the nitrogen they are bound to a group of the formula A.1

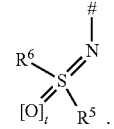

(A.1)

26. The method of claim 14, wherein, in the compound of formula (I), wherein
$R^5$ and $R^6$ each independently are $C_1$-$C_{12}$-alkyl which may be partially or fully halogenated and/or substituted by one or more $C_1$-$C_6$-alkoxy groups; or $C_3$-$C_8$-cycloalkyl which may be partially or fully halogenated.

* * * * *